United States Patent [19]

Carson et al.

[11] Patent Number: 5,025,036
[45] Date of Patent: Jun. 18, 1991

[54] CATECHOL CARBOXYLIC ACIDS

[75] Inventors: Matthew Carson, Nutley; Ru-Jen L. Han, Princeton Junction; Ronald A. LeMahieu, North Caldwell, all of N.J.

[73] Assignee: Hoffmann-La Roche Inc., Nutley, N.J.

[21] Appl. No.: 347,109

[22] Filed: May 3, 1989

Related U.S. Application Data

[63] Continuation-in-part of Ser. No. 234,239, Aug. 19, 1988, abandoned, which is a continuation-in-part of Ser. No. 223,470, Jul. 22, 1988, abandoned, which is a continuation-in-part of Ser. No. 103,789, Oct. 1, 1987, abandoned.

[51] Int. Cl.$^5$ .............................. A61K 31/19
[52] U.S. Cl. .................. 514/568; 514/533; 514/534; 514/539; 514/544; 514/546; 514/567; 514/646; 514/647; 514/679; 514/685; 514/716; 514/721; 560/46; 560/53; 560/64; 560/65; 560/66; 560/70; 560/74; 560/108; 560/138; 560/141; 562/453; 562/463; 562/473; 562/474; 562/476; 564/307; 564/422; 564/443; 568/306; 568/325; 568/329; 568/331; 568/586; 568/644; 568/645
[58] Field of Search ............... 562/463, 473, 474, 476, 562/453; 560/53, 46, 65, 64, 66, 74, 70, 108, 141, 138; 568/329, 306, 325, 331, 586, 644, 645; 514/533, 534, 539, 544, 546, 567, 568, 685, 646, 647, 721, 679, 716; 564/307, 441, 422, 443

[56] References Cited

U.S. PATENT DOCUMENTS 3,987,108 10/1976 Karrer ................................. 568/644
4,067,892 1/1978 Thorne ............................... 568/331

OTHER PUBLICATIONS

Derwent Abst. of Jap. Pat. 61-106,531A.
Derwent Abst. of Jap. Pat. 61-118,346A.
Derwent Abst. of Jap. Pat. 60-260,532A.
Derewnt Abst. of Jap. Pat. 61-106,545A.

Primary Examiner—Michael L. Shippen
Attorney, Agent, or Firm—George M. Gould; Bernard S. Leon; William G. Isgro

[57] ABSTRACT

The invention relates to catechol carboxylic acid derivatives of the formula

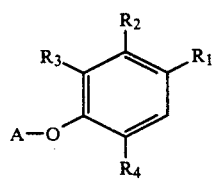

wherein,
$R_1$ is

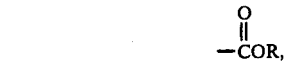

acetyl, hydrogen, hydroxy or alkanoyloxy,
$R_2$ is

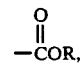

hydroxy, hydrogen or alkanoyloxy, wherein R is hydrogen, lower alkyl or $-(CH_2)_n-N-$(lower alkyl)$_2$,
$R_3$ is hydrogen, lower alkyl or amino,
$R_4$ is hydrogen, lower alkyl, halogen or amino
A is

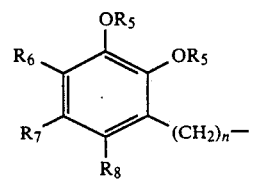

wherein, $R_5$ is hydrogen or acyl, $R_6$ is hydrogen, halogen, lower alkyl, aryl or cycloalkyl, and $R_7$ and $R_8$, independently, are hydrogen, lower alkyl or halogen, or
A is

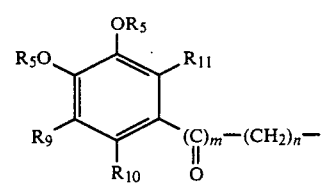

wherein, $R_5$ is hydrogen or acyl, $R_9$ is hydrogen, lower alkyl, $R_{10}$ is hydrogen, lower alkyl or halogen, $R_{11}$ is hydrogen, lower alkyl, cycloalkyl or halogen, m is 0 or 1, n is an integer of 2-10, provided, that no more than one of $R_1$ or $R_2$ can be hydroxy, alkanoyloxy or

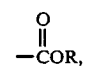

and when R is hydrogen, salts thereof with pharmaceutically acceptable bases or when R is $-(CH_2)_n-N-($lower alkyl)$_2$, salts thereof with pharmaceutically acceptable acids.

The compounds of formula I are useful as agents for the treatment of inflammatory diseases such as arthritis, inflammatory bowel disease such as colitis, cardiovascular diseases such as myocardial ischemia, skin diseases such as psoriasis by topical administration, and bronchopulmonary diseases such as asthma.

59 Claims, No Drawings

CATECHOL CARBOXYLIC ACIDS

CROSS-REFERENCE TO RELATED APPLICATION

This application is a continuation-in-part of U.S. application Ser. No. 234,239, filed Aug. 19, 1988, now abandoned which in turn is a continuation-in-part of U.S. application Ser. No. 223,470, filed Jul. 22, 1988, now abandoned which in turn is a continuation-in-part of U.S. application Ser. No. 103,789, filed Oct. 1, 1987, now abandoned.

BRIEF DESCRIPTION OF THE INVENTION

The invention relates to catechol carboxylic acid derivatives of the formula

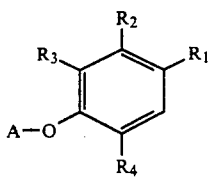
I wherein
$R_1$ is

hydrogen, acetyl, hydroxy or alkanoyloxy,
$R_2$ is

hydroxy, hydrogen or alkanoyloxy, wherein R is hydrogen, lower alkyl or $-(CH_2)_n N$ (lower alkyl)$_2$,
$R_3$ is hydrogen, lower alkyl or amino,
$R_4$ is hydrogen, lower alkyl, halogen or amino,
A is

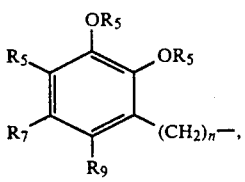
A' wherein $R_5$ is hydrogen or acyl, $R_6$ is hydrogen, halogen, lower alkyl, aryl or cycloalkyl, and $R_7$ and $R_8$, independently, are hydrogen, lower alkyl or halogen, and n is an integer of 2–10, or
A is

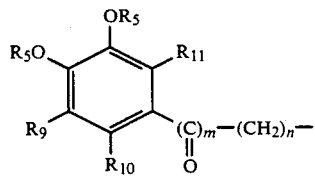
A″ wherein $R_5$ is hydrogen or acyl, $R_9$ is hydrogen or lower alkyl, $R_{10}$ is hydrogen, lower alkyl or halogen, $R_{11}$ is hydrogen, lower alkyl, cycloalkyl or halogen, m is 0 or 1, n is an integer of 2–10, provided that no more than one of $R_1$ or $R_2$ can be hydroxy, alkanoyloxy or

and, when R is hydrogen, salts thereof with pharmaceutically acceptable bases, and, when R is $(CH_2)_n-N-(\text{lower alkyl})_2$, addition salts thereof with pharmaceutically acceptable acids.

The compounds of formula I are useful as agents for the treatment of inflammatory diseases such as arthritis, inflammatory bowel diseases such as colitis, cardiovascular diseases such as myocardial ischemia, skin diseases such as psoriasis by topical administration, and bronchopulmonary diseases such as asthma.

DETAILED DESCRIPTION OF THE INVENTION

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl, and the like. Branched chain saturated hydrocarbons are preferred for $R_6$, $R_9$ and $R_{11}$. The term "halogen" denotes all the halogens, that is, bromine, chlorine, fluorine, and iodine. The term "aryl" denotes phenyl or phenyl bearing one or two substituents independently selected from the group consisting of halogen, trifluoromethyl, lower alkyl, lower alkoxy, nitro, amino, lower alkylamino and di-lower alkylamino. The term "acyl" denotes an "alkanoyl" group derived from an aliphatic carboxylic acid of 1 to 7 carbon atoms, for example, formyl, acetyl, propionyl, and the like; and an "aroyl" group derived from an aromatic carboxylic acid, for example, benzoyl and the like. The term "alkanoyloxy" denotes a group derived from an aliphatic carboxylic acid of 1 to 7 carbon atoms, for example, formyloxy, acetoxy, propionyloxy, and the like. The term "cycloalkyl" denotes preferably a cyclic hydrocarbon of 3 to 6 carbon atoms which may be unsubstituted or substituted by lower alkyl and most preferably of 5 to 6 carbon atoms, for example, cyclopropyl, cyclopentyl, cyclohexyl or the like.

The invention relates to catechol carboxylic acid derivatives of the formula

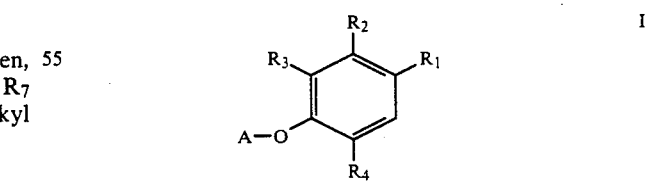
I wherein
$R^1$ is

acetyl, hydrogen, hydroxy or alkanoyloxy, $R_2$ is

hydroxy, hydrogen or alkanoyloxy, wherein R is hydrogen, lower alkyl or $-(CH_2)_nN$ (lower alkyl)$_2$, $R_3$ is hydrogen, lower alkyl or amino,
$R_4$ is hydrogen, lower alkyl, halogen or amino,
A is

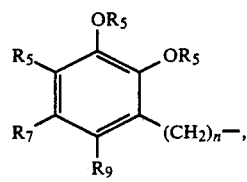

wherein $R_5$ is hydrogen or acyl, $R_6$ is hydrogen, halogen, lower alkyl, aryl or cycloalkyl, and $R_7$ and $R_8$, independently, are hydrogen, lower alkyl or halogen, or A is

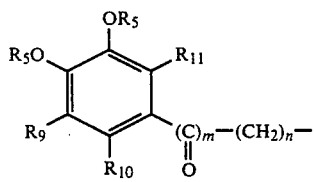

wherein $R_5$ is hydrogen or acyl, $R_9$ is hydrogen or lower alkyl, $R_{10}$ is hydrogen, lower alkyl or halogen, $R_{11}$ is hydrogen, lower alkyl, cycloalkyl or halogen, m is 0 or 1, n is an integer of 2-10, provided, that no more than one of $R_1$ or $R_2$ can be hydroxy, alkanoyloxy or

and, when R is hydrogen, salts thereof with pharmaceutically acceptable bases, and, when R is $-(CH_2)_n-N-$(lower alkyl)$_2$, addition salts thereof with pharmaceutically acceptable acids.

The compounds of formula I can also be characterized by the formulas Ia and Ib, depending upon whether the moiety A is fragment A' or A", respectively, as follows:

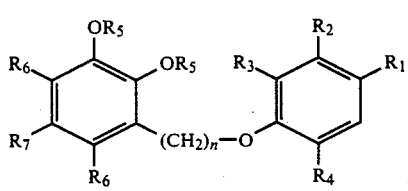

or

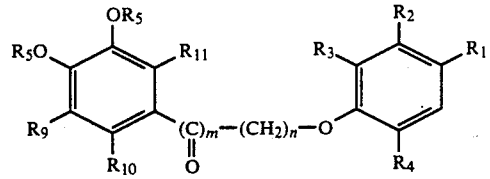

wherein $R_1$, $R_2$, $R_3$, $R_4$, $R_5$, $R_6$, $R_7$, $R_8$, $R_9$, $R_{10}$, $R_{11}$, m and n are as herein described.

Preferred compounds of formula Ia of the invention are those wherein $R_1$ is carboxy or acetyl, $R_2$ is hydroxy, $R_3$ is hydrogen or propyl, $R_4$ is hydrogen or chloro, n is an integer 2–10, $R_5$ is hydrogen or acetyl, $R_6$ is hydrogen, lower alkyl or aryl, $R_7$ and $R_8$ are hydrogen.

Preferred compounds of formula Ib of the invention are those wherein $R_1$ is carboxy or acetyl, $R_2$ is hydroxy, $R_3$ is hydrogen or propyl, $R_4$ is hydrogen or chloro, m is 0 or 1, n is an integer from 2–10, $R_5$ is hydrogen or acetyl, $R_9$ and $R_{10}$ are hydrogen, and $R_{11}$ is hydrogen or chloro.

More preferred compounds of formula Ia are those wherein $R_1$ is carboxy or acetyl, $R_2$ is hydroxy, $R_3$ is hydrogen or propyl, $R_4$ is hydrogen or chloro, n is an integer from 4 to 8, $R_5$ is hydrogen or acetyl, $R_6$ is hydrogen or lower alkyl and $R_7$ and $R_8$ are hydrogen.

More preferred compounds of formula Ib are those wherein $R_1$ is carboxy or acetyl, $R_2$ is hydroxy, $R_3$ is n-propyl, $R_4$ is hydrogen, m is 0, n is an integer from 4–6, $R_5$ is hydrogen or acetyl, $R_9$ and $R_{10}$ are hydrogen, $R_{11}$ is hydrogen or chloro.

Most preferred compounds of formula Ia are those wherein $R_1$ is carboxy or acetyl, $R_2$ is hydroxy, $R_3$ is n-propyl or hydrogen, $R_4$ is hydrogen, n is an integer from 4–8, $R_5$ is hydrogen, $R_6$ is hydrogen or α-branched lower alkyl, and $R_7$ and $R_8$ are hydrogen.

Most preferred compounds of formula Ib are those wherein $R_1$ is carboxy or acetyl, $R_2$ is hydroxy, $R_3$ is n-propyl, $R_4$ is hydrogen, m is 0, n is an integer from 4 to 6, $R_5$, $R_9$, $R_{10}$ and $R_{11}$ are hydrogen.

The preferred compounds of the invention are:
4-[6-(2,3-dihydroxyphenyl)hexyloxy]-2-hydroxybenzoic acid;
4-[6-(2,3-dihydroxyphenyl)hexyloxy]benzoic acid;
4-[6-(3,4-dihydroxy-2,5-dimethylphenyl)hexyloxy]-2-hydroxy-3-propylbenzoic acid;
4-[5-(2,3,4-trichloro-5,6-dihydroxyphenyl)pentyloxy]-2-hydroxy-3-propylbenzoic acid;
4-[4-(2,3-dihydroxyphenyl)butoxy]-2-hydroxy-3-propylbenzoic acid;
4-[6-(2,3-dihydroxyphenyl)hexyloxy]-2-hydroxy-3-propylbenzoic acid;
4-[8-(2,3-dihydroxyphenyl)octyloxy]-2-hydroxy-3-propylbenzoic acid;
4-[6-[2,3-bis(acetyloxy)phenyl]hexyloxy]2-hydroxy-3-propylbenzoic acid;
4-[6-[2,3-dihydroxy-4-(1-methylethyl)phenyl]hexyloxy]-2-hydroxy-3-propylbenzoic acid;
4-[3-(3,4-dihydroxyphenyl)propoxy]-2-hydroxy-3-propylbenzoic acid;
4-[6-(3,4-dihydroxyphenyl)hexyloxy]-2-hydroxy-3-propylbenzoic acid;
4-[[6-(3,4-dihydroxyphenyl)-6-oxohexyl]oxy]-2-hydroxy-3-propylbenzoic acid; and
1-[2-hydroxy-4-[4-(2,3-dihydroxyphenyl)butoxy]-3-propylphenyl]ethanone Exemplary of other compounds of the invention are:

4-[6-[2,3-dihydroxy-4-(1,1-dimethylethyl)phenyl]hexyloxy]2-hydroxy-3-propylbenzoic acid;

4-[6-[2,3-dihydroxy-4-methylphenyl]hexyloxy]2-hydroxy-3-propylbenzoic acid;

4-[4-[2,3-dihydroxy-4-(2-methylpropyl)phenyl]butoxy]2-hydroxy-3-propylbenzoic acid;

4-[6-[2,3-dihydroxy-5,6-dimethylphenyl]hexyloxy]2-hydroxy-3-propylbenzoic acid;

4-[5-[5-chloro-2,3-dihydroxyphenyl]pentyloxy]-2-hydroxy-3-propylbenzoic acid;

4-[6-[2,3-dihydroxy-6-fluorophenyl]hexyloxy]2-hydroxy-3-propylbenzoic acid;

4-[4-[2,3-dihydroxy-4-cyclohexylphenyl]butoxy]2-hydroxy-3-propylbenzoic acid;

4-[4-[2,3-dihydroxy-4-(1,1-dimethylethyl)phenyl]butoxy]2-hydroxy-3-propylbenzoic acid;

4-[8-[2,3-dihydroxy-4-(1,1-dimethylethyl)phenyl]octyloxy]2-hydroxy-3-propylbenzoic acid;

4-[4-[2,3-dihydroxy-4-(1,1-dimethylethyl)phenyl]butoxy]2-hydroxybenzoic acid;

4-[8-[2,3-dihydroxy-4-(1-methylethyl)phenyl]octyloxy]2-hydroxybenzoic acid;

4-[8-[2,3-dihydroxyphenyl]butoxy]-3,5-dipropyl-2-hydroxybenzoic acid;

4-[4-[2,3-dihydroxy-4-(1-methylethyl)phenyl]butoxy]-3,5-dipropylbenzoic acid;

4-[6-[2,3-dihydroxy-4-(1-methylethyl)phenyl]hexyloxy]3-propylbenzoic acid;

4-[6-[2,3-bis(acetyloxy)-4-(1-methylethyl)phenyl]hexyloxy]2-hydroxy-3-propylbenzoic acid;

2-acetyloxy-4-[6-(2,3-dihydroxy-4-(1-methylethyl)phenyl]hexyloxy]-3-propylbenzoic acid;

4-[6-[2,3-bis[4-methylbenzoyl)oxy]-4-(1-methylethyl)phenyl]-hexyloxy]-2-hydroxy-3-propylbenzoic acid;

1-[2-hydroxy-4-[6-[2,3-dihydroxy-4-(1,1-dimethylethyl)phenyl]-hexyloxy]-3-propylphenyl]ethanone;

1-[2-hydroxy-4-[8-[2,3-dihydroxy-6-fluorophenyl]octyloxy]-3-propylphenyl]ethanone;

1-[2-hydroxy-4-[6-[6-chloro-2,3-dihydroxyphenyl]hexyloxy]-3-propylphenyl]ethanone;

1-[2-hydroxy-4-[6-[5,6-dichloro-2,3-dihydroxyphenyl]hexyloxy]-3-propylphenyl]ethanone;

1-[2-hydroxy-4-[6-[2,3-dihydroxy-4,5,6-trichlorophenyl]hexyloxy]-3-propylphenyl]ethanone;

5-[6-(2,3-dihydroxy-4-(1-methylethyl)phenyl]hexyloxy]-2-hydroxybenzoic acid;

4-[6-[2,3-dihydroxy-4-(1-methylethyl)phenyl]hexyloxy]benzoic acid;

4-[6-[2,3-dihydroxy-4-(1-methylethyl)phenyl]hexyloxy]2-hydroxy-3-propylbenzoic acid ethyl ester;

4-[6-[2,3-dihydroxy-4-(1-methylethyl)phenyl]hexyloxy]-2-hydroxy-3-propylbenzoic acid ethyl ester;

4-[8-(3,4-dihydroxyphenyl)octyloxy]-2-hydroxy-3-propyl benzoic acid;

4-[3-(3,4-dihydroxyphenyl)propoxy]-2-hydroxy-3-propyl benzoic acid ethyl ester;

4-[6-(3,4-dihydroxyphenyl)hexyloxy]-2-hydroxy benzoic acid;

4-[6-(3,4-dihydroxyphenyl)hexyloxy]-3-propylbenzoic acid;

4-[8-(3,4-dihydroxyphenyl)octyloxy]benzoic acid;

3-[8-(3,4-dihydroxyphenyl)octyloxy]benzoic acid;

5-[8-(3,4-dihydroxyphenyl)octyloxy]-2-hydroxybenzoic acid;

4-[[8-(3,4-dihydroxyphenyl)-8-oxooctyl]oxy]-2-hydroxy-3-propylbenzoic acid;

4-[[4-(3,4-dihydroxyphenyl)-4-oxobutyl]oxy]-2-hydroxy-3-propylbenzoic acid;

4-[6-(3,4-dihydroxy-5-fluorophenyl)hexyloxy]-2-hydroxy-3-propylbenzoic acid;

4-[6-(3,4-dihydroxy-6-fluorophenyl)hexyloxy]-2-hydroxy-3-propylbenzoic acid;

4-[6-(3,4-dihydroxy-6-chlorophenyl)hexyloxy]-2-hydroxy-3-propylbenzoic acid;

4-[4-(3,4-dihydroxy-5(1-methylethyl)phenyl]butoxy]-2-hydroxy-3-propylbenzoic acid;

4-[4-[3,4-dihydroxy-5(1,1-dimethylethyl)phenyl]butoxy]-2-hydroxybenzoic acid;

4-[6-[3,4-bis(acetyloxy)phenyl]hexyloxy]-2-hydroxy-3-propylbenzoic acid;

2-acetyloxy-4-[6-(3,4-dihydroxyphenyl)hexyloxy[-3-propylbenzoic acid;

4-[[4-[3,4-dihydroxy-5-(1-methylethyl)phenyl]-4-oxobutyl]oxy]-2hydroxybenzoic acid;

4-[6-[3,4-dihydroxy-2-(1-methylethyl)phenyl]hexyloxy]-2-hydroxy-3-propylbenzoic acid;

4-[[4-(3,4-dihydroxy-2,5-dimethylphenyl)-4-oxobutyl]oxy]-2-hydroxy-3-propylbenzoic acid;

4-[4-(3,4-dihydroxy-2,5-dimethylphenyl)butoxy]-2-hydroxy-3-propylbenzoic acid;

4-[[6-(3,4-dihydroxy-2,5-6-trimethylphenyl)-6-oxohexyl]oxy]-2-hydroxy-3-propylbenzoic acid;

4-[6-(3,4-dihydroxy-,5,6-trimethylphenyl)hexyloxy]-2-hydroxy-3-propylbenzoic acid;

1-[2-hydroxy-4-[6-(3,4-dihydroxyphenyl)hexyloxy]-3-propylphenyl-1-ethanone;

1-[2-hydroxy-4-[8-(3,4-dihydroxyphenyl)octyloxy]-3-propylphenyl-1-ethanone;

1-[2-hydroxy-4-[6-(3,4-dihydroxy-2,5-dimethylphenyl)hexyloxy]-3-propylphenyl-1-ethanone;

1-[2-hydroxy-4-[6-(3,4-dihydroxy-6-chlorophenyl)hexyloxy]-3-propylphenyl-1-ethanone;

1-[2-hydroxy-4-[6-(3,4-dihydroxy-2-chlorophenyl)hexyloxy]-3-propylphenyl-1-ethanone;

1-[2-hydroxy-4-[6-(3,4-dihydroxy-6-fluorophenyl)hexyloxy]-3-propylphenyl-1-ethanone;

The compounds of Formula I, and intermediates therefor, can be prepared as described in Reaction Schemes I to XII.

REACTION SCHEME I

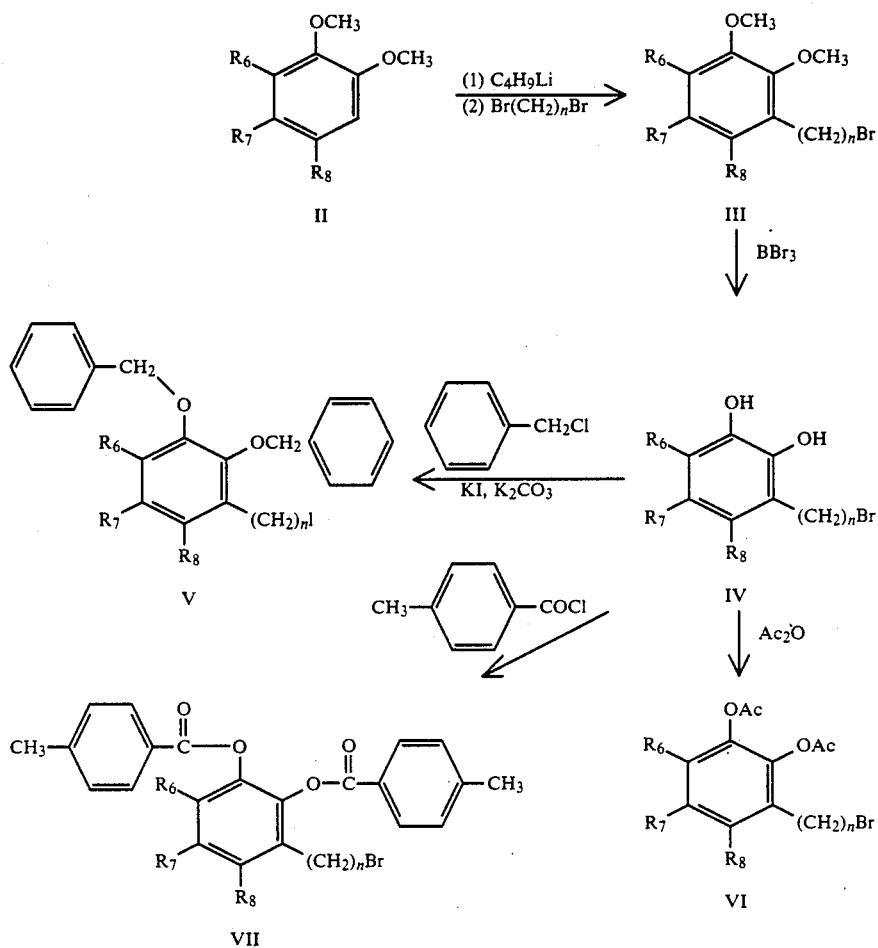

wherein $R_6$, $R_7$, $R_8$ and n are as previously described, and Ac is acetyl.

In Reaction Scheme I, a compound of formula II, which are known compounds or can be prepared according to known procedures, can be converted to the corresponding known compounds of formula III as described in H. Halim, H. D. Locksley and J. J. Memon, J. Chem. Soc. Perkin I, 2331 (1980). More particularly, a compound of formula II is reacted with an alkyl lithium reagent, preferably butyl lithium, in the presence of a solvent such as diethylether, tetrahydrofuran or the like at a temperature in the range of from about $-75°$ to $0°$, to yield the corresponding lithium salt followed by reaction in situ with an excess of a dibromo alkane at a temperature in the range of from about $0°$ to $50°$.

A compound of formula III can be converted to the corresponding compound of formula IV, for example, with boron tribromide in a halogenated hydrocarbon solvent, for example, chloroform or 1,2-dichloroethane or preferably methylene chloride at a temperature in the range of from about $-75°$ to about $25°$.

The resulting compound of formula IV can be converted to the corresponding compound of formula V in the presence of benzyl chloride, benzyl bromide or the like, potassium iodide or sodium iodide and an alkali metal carbonate, for example, sodium or potassium carbonate, in a solvent such as acetone, methyl ethyl ketone or the like, at reflux or with dimethyl formamide at a temperature in the range of from about $50°$ to about $100°$.

The compound of formula IV can be converted to a corresponding compound of formula VI in the presence of acetic anhydride and acid catalyst, for example, perchloric acid, in a solvent such as ethyl acetate and the like, at a temperature in the range of from $0°$ to about $25°$.

Alternatively, the resulting compound of formula IV can be converted to a corresponding compound of formula VII with 4-methylbenzoyl chloride and an organic tertiary amine base such as triethylamine, in a solvent such as tetrahydrofuran, dioxane or ethyl ether, at a temperature in the range of from $0°$ to about $25°$.

REACTION SCHEME II

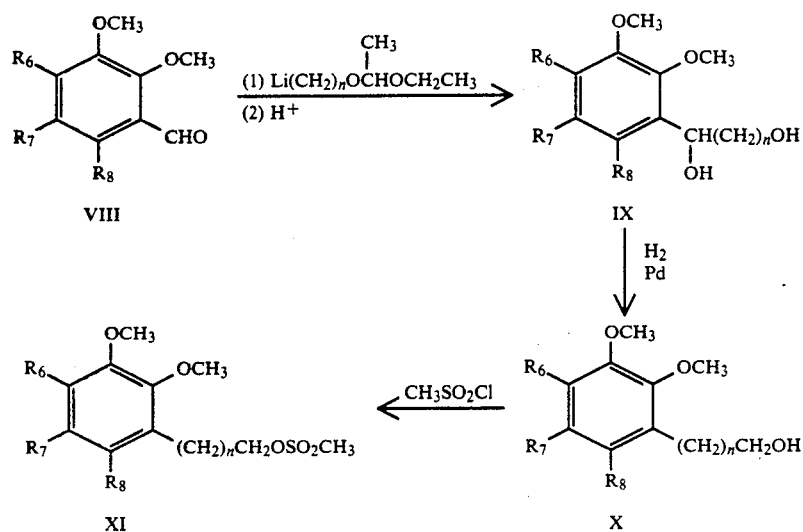

wherein $R_6$, $R_7$ and $R_8$ and n are as previously described.

In Reaction Scheme II, an aldehyde of formula VIII, which are known compounds or can be prepared according to known procedures, can be converted to the corresponding compound of formula IX as described in J. H. P. Tyman and C. H. Khor, Chem. Ind., 526 (1974). More particularly, the aldehyde of formula VIII is allowed to react with a lithium reagent, prepared by standard procedures, in a solvent such as ethyl ether, tetrahydrofuran or the like, at a temperature in the range of from about $-20°$ to about $35°$. The alcohol protecting group can be removed from the product by treatment with dilute hydrochloric acid at $25°$ to give a diol of formula IX.

Thereafter, hydrogenolysis of a compound of formula IX gives the corresponding compound of formula X by shaking on a Parr apparatus under hydrogen pressure of from about 40–60 psi, using a palladium catalyst, at a temperature in the range of from about $25°$ to about $50°$, in a solvent, such as, ethyl acetate, ethanol, tetrahydrofuran and the like.

Conversion of a compound of formula X to the corresponding mesylate XI can be carried out under standard conditions, for example, with methanesulfonyl chloride and triethylamine in a solvent such as methylene chloride at a temperature in the range of from about $-20°$ to about $25°$.

REACTION SCHEME III

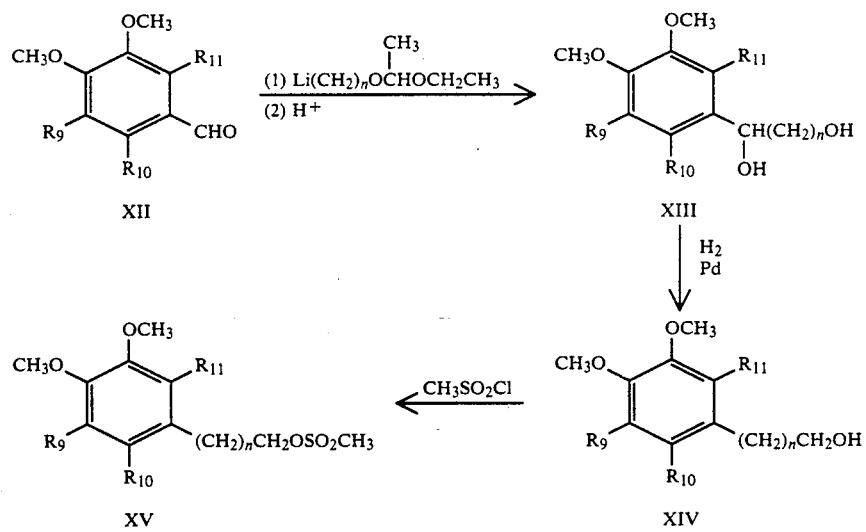

wherein $R_9$, $R_{10}$, $R_{11}$ and n are as previously described.

In Reaction Scheme III, a compound of formula XII can be converted to a corresponding compound of formula XIII and which in turn can be converted to corresponding compounds of formulas XIV and XV, utilizing the reaction conditions set forth in Reaction Scheme II.

REACTION SCHEME IV

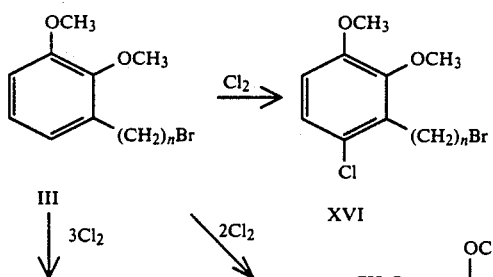

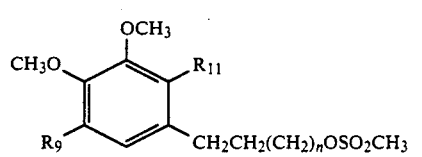

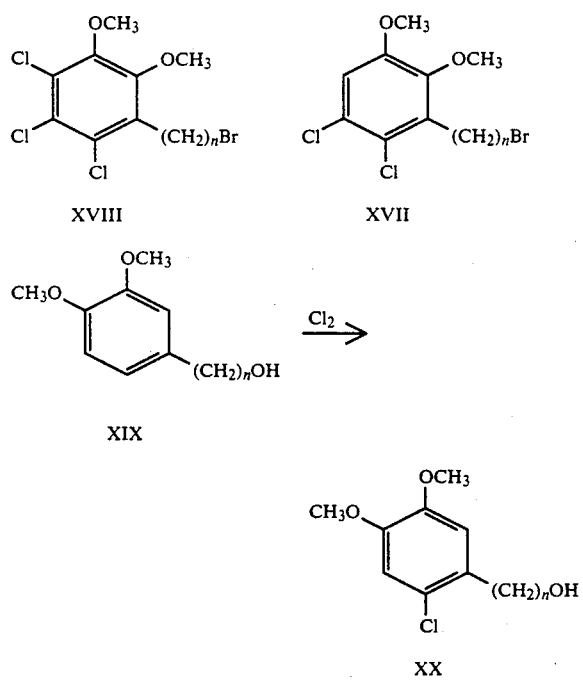

wherein n is as previously described.

In Reaction Scheme IV, a compound of formula III, which are known compounds or can be prepared according to known procedures, can be converted to the corresponding monochloro compounds of formula XVI, the dichloro compounds of formula XVII and the trichloro compounds of formula XVIII by treatment with the appropriate quantity of chlorine, in an inert solvent such as a chlorinated hydrocarbon, for example, methylene chloride, chloroform, 1,2-dichloromethane and the like, at a temperature in the range of from about −20° to about 25°.

The conversion of a compound of formula XIX to the corresponding compound of formula XX can be carried out utilizing the reaction condition first described above.

REACTION SCHEME V

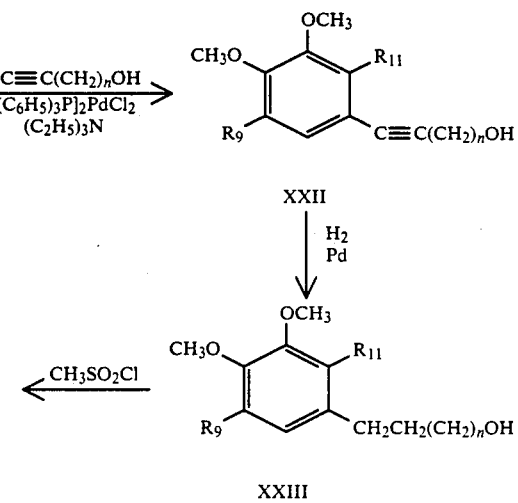

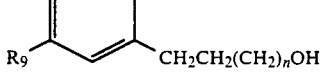

wherein $R_9$, $R_{11}$ and n are as previously described.

In Reaction Scheme V, a compound of formula XXI is converted to an acetylenic alcohol of formula XXII by reaction with an acetylenic alcohol in the presence of bis(triphenylphosphine) palladium dichloride, cuprous iodide and an organic amine (triethylamine) as described in K. Sonogashira, Y. Tohda and N. Hagihara, Tet. Letters, 4467 (1975).

The reaction is carried out in a solvent, for example, a halogenated hydrocarbon, for example, methylene chloride, chloroform, 1,2-dichloroethane and the like, at a temperature in the range of from about 25° to about 50°.

A resulting compound of formula XXII is converted to a compound of formula XXIII utilizing standard conditions, for example, catalytic hydrogenation at atmospheric pressure and room temperature.

A resulting compound of formula XXIII can be converted to a compound of formula XXIV utilizing standard conditions, for example, in the presence of methanesulfonyl chloride, triethylamine in methylene chloride, as the solvent at a temperature in the range of from about −20° to about 25°.

REACTION SCHEME VI

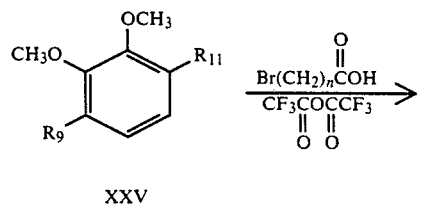

-continued
REACTION SCHEME VI

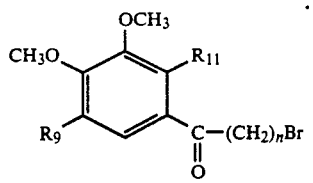

XXVI

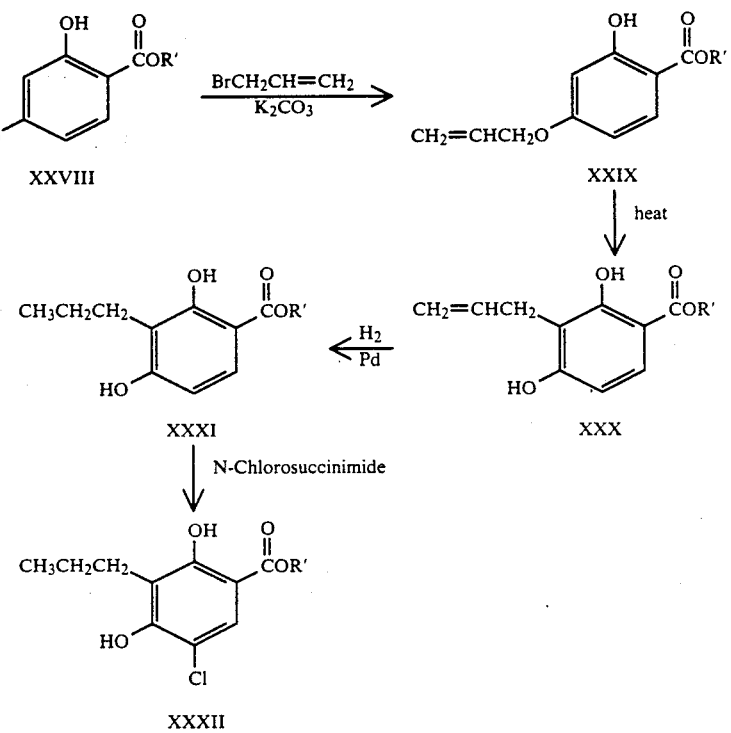

XXVII wherein $R_9$, $R_{11}$ and n are as previously described.

In Reaction Scheme VI, a compound of formula XXV, which are known compounds or can be prepared according to known procedures, can be converted to a compound of formula XXVI utilizing standard acylation conditions, for example, treatment with a bromo acid and trifluoroacetic anhydride at a temperature in the range of from 25° to about 40° without solvent or with a solvent such as methylene chloride, 1,2-dichloroethane or the like. Alternatively, a bromoacid chloride and aluminum chloride in a solvent such as methylene chloride or 1,2-dichloroethane at a temperature in the range of from 0° to about 40° can be also be utilized.

The reduction of a compound of formula XXVI to the corresponding compound of formula XXVII can be accomplished by hydrogenation in a Parr apparatus at hydrogen pressures of about 50 to about 60 psi, using a palladium catalyst in a solvent such as ethanol, ethyl acetate, tetrahydrofuran or the like, at a temperature in the range of from 25° to about 70°. A mineral acid catalyst can be used in addition to palladium catalyst.

REACTION SCHEME VII wherein R' is lower alkyl.

In Reaction Scheme VII, a compound of formula XXVIII, which are known compounds or can be prepared according to known procedures, can be converted to the corresponding compound of formula XXIX utilizing standard alkylation conditions, for example, utilizing allyl bromide or chloride, an alkali metal carbonate such as sodium carbonate, or preferably potassium carbonate in a solvent such as methyl ethyl ketone, dimethylformamide, preferably, acetone at a temperature in the range of from about 40° to about 60°.

The rearrangement of a compound of formula XXIX to a compound of formula XXX is carried out by heating in an inert atmosphere, at a temperature in the range of from about 175° to about 200°.

The hydrogenation of a compound of formula XXX to the corresponding compound of formula XXXI can be carried out utilizing a standard catalytic hydrogenation reaction, for example, at atmospheric pressure or under hydrogen pressure such as 50 psi, in a solvent such as ethyl acetate, tetrahydrofuran, ethanol or the like, at a temperature in the range of from about 25° to about 50°.

The chlorination of a compound of formula XXXI to the corresponding compound of formula XXXII can be carried out utilizing a standard chlorination reaction, for example, with N-chlorosuccinimide in a solvent such as carbon tetrachloride, chloroform or the like, at the reflux temperature.

REACTION SCHEME VIII

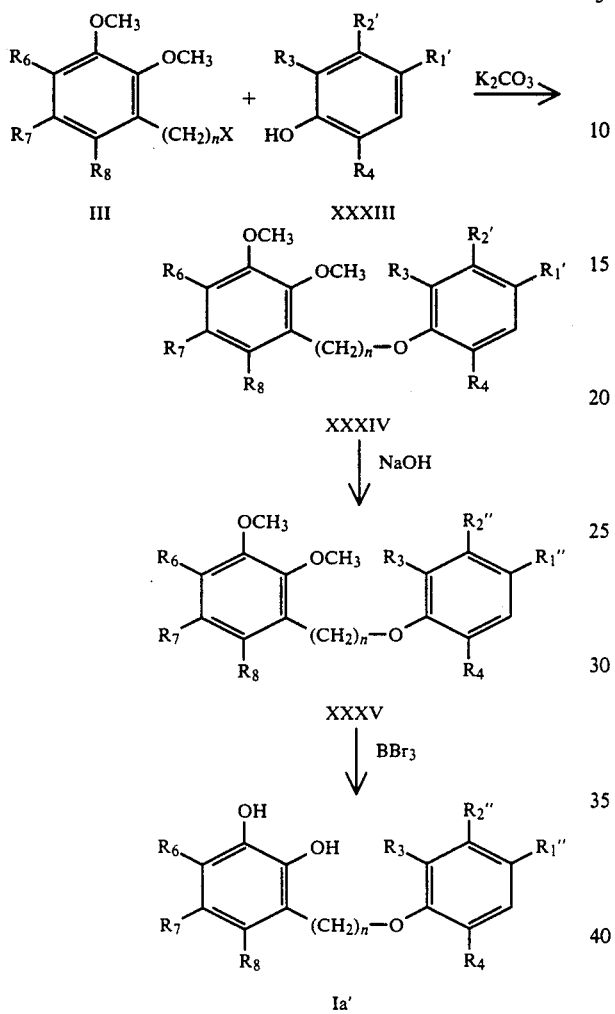

wherein $R_1'$, is —COOR', acetyl, hydrogen or hydroxy, $R_2'$ is —COOR', hydrogen or hydroxy, R' is lower alkyl, $R_1''$, is carboxy, acetyl, hydrogen or hydroxy, $R_2''$ is carboxy, hydrogen or hydroxy, X is bromo or methanesulfonyloxy, provided that no more than one of $R_1'$ or $R_2'$ can be hydroxy or —COOR', or that no more than one of $R_1''$ or $R_2''$ can be carboxy or hydroxy, $R_3$, $R_4$, $R_6 R_7$ and $R_8$ and n are as previously described.

In Reaction Scheme VIII, a compound of formula III is reacted with a compound of formula XXXIII to yield the corresponding compound of formula XXXIV. The reaction is carried out utilizing an alkali metal carbonate as the base, for example, sodium carbonate, preferably potassium carbonate, with added sodium iodide or potassium iodide, in a solvent such as acetone, methyl ethyl ketone, dimethylformamide, toluene or the like, at a temperature in the range of from about 40° C. to about 70° C. The solid-liquid phase-transfer catalyst tris[2-(2-methoxyethoxy)ethyl]amine can be used to facilitate the reaction when toluene is the solvent.

The hydrolysis of a compound of formula XXXIV to the corresponding compound of formula XXXV can be carried out utilizing standard conditions, for example, utilizing an alkali metal hydroxide such as sodium hydroxide or potassium hydroxide, in a solvent such as methanol, ethanol or the like, sometimes with added dioxane to aid solubility, at a temperature in the range of from about 25° to about 65°.

The conversion of a compound of formula XXXV to the corresponding compound of formula Ia' can be carried out utilizing, for example, boron tribromide in a solvent such as methylene chloride, chloroform, 1,2-dichloroethane or the like at a temperature in the range of from $-70°$ to $25°$. The resulting compound of formula Ia' is recovered and purified utilizing known and conventional procedures, for example, precipitation, crystallization, chromatography or the like.

REACTION SCHEME IX

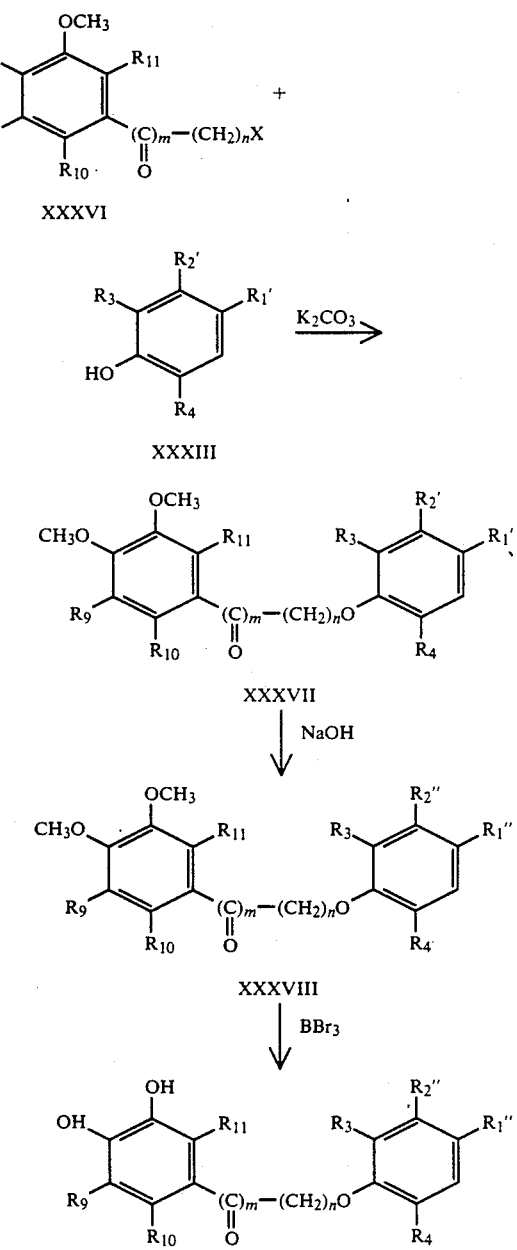

wherein $R_3$, $R_4$, $R_9$, $R_{10}$, $R_{11}$, $R_2'$, $R_1'$, $R_2''$, $R_1''$, m, n and X are as previously described, provided that no more than one of $R_1'$ and $R_2'$ can be hydroxy or —COOR', or that no more than one of $R_1''$ and $R_2''$ can be carboxy or hydroxy.

In Reaction Scheme IX, a compound of formula XXXVI is reacted with a compound of formula XXXIII to yield the corresponding compound of formula XXXVII. The reaction is carried out utilizing an alkali metal carbonate such as sodium carbonate or preferably potassium carbonate in a solvent such as acetone, methyl ethyl ketone, dimethylformamide or the like, at a temperature in the range of from about 40° to about 70°.

The conversion of a compound of formula XXXVII to the corresponding compound of formula XXXVIII can be carried out utilizing, for example, an alkali metal hydroxide such as sodium hydroxide, potassium hydroxide or the like, in a solvent such as methanol, ethanol or the like, sometimes with added dioxane to aid solubility, at a temperature in the range of from about 25° to about 65°.

The conversion of a compound of formula XXXVIII to the corresponding compound of formula Ib' can be carried out utilizing, for example, boron tribromide, in a solvent such as methylene chloride, chloroform, 1,2-dichloroethane or the like at a temperature in the range of from about −70° to about 25°. The resulting compound of formula Ib' is recovered and purified utilizing known and conventional procedures, for example, precipitation, crystallization, chromatography or the like.

If desired, a compound of formula XXXVII, XXXVIII or Ib' wherein m=1 can be converted to the corresponding compounds where m=0 and the linking chain contains n+1 methylene groups by shaking under hydrogen pressure. The conversion can be carried out using a catalyst such as palladium in a solvent such as ethanol, ethyl acetate or tetrahydrofuran using pressure of 40–60 psi. Small amounts of an acid such as concentrated sulfuric acid can be used to accelerate the reaction.

REACTION SCHEME X

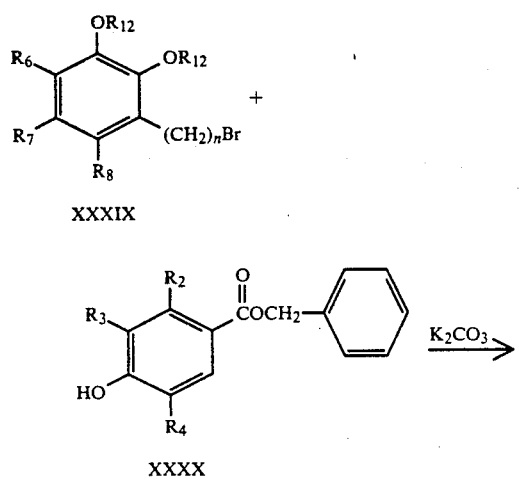

-continued
REACTION SCHEME X

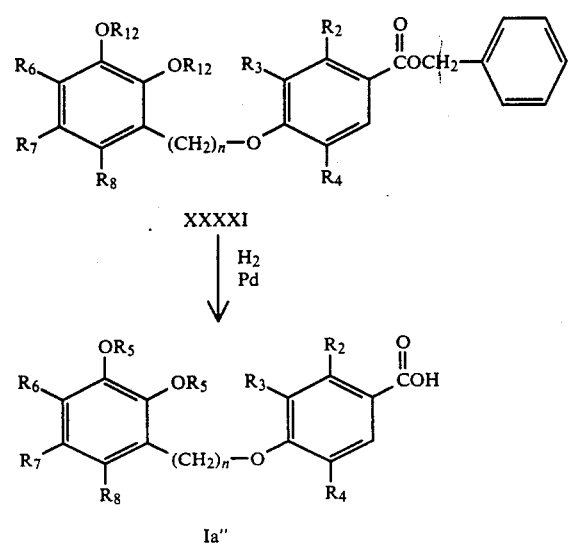

wherein $R_2$, $R_3$, $R_4$, $R_6$, $R_7$, $R_8$ and n are as previously described and $R_{12}$ is benzyl or acyl.

In Reaction Scheme X, a compound of formula XXXIX is reacted with a compound of formula XXXX to yield the corresponding compound of formula XXXXI. The reaction is carried out utilizing an alkali metal carbonate such as sodium carbonate or potassium carbonate, or sodium hydride, in a solvent such as acetone, methyl ethyl ketone, dimethylformamide or the like at a temperature in the range of from about 25° to about 70°. The hydrogenolysis of a compound of formula XXXXI to the corresponding compound of formula Ia'' can be carried out utilizing a standard catalytic hydrogenolysis reaction, for example, at atmospheric pressure or hydrogen pressure up to 50 psi at a temperature in the range of from about 25° to about 50°, in a solvent such as ethyl acetate, tetrahydrofuran or the like, and in the presence of a catalyst such as palladium. The resulting compound of formula Ia'' is recovered and purified utilizing known and conventional procedures, for example, precipitation, crystallization, chromatography or the like.

REACTION SCHEME XI

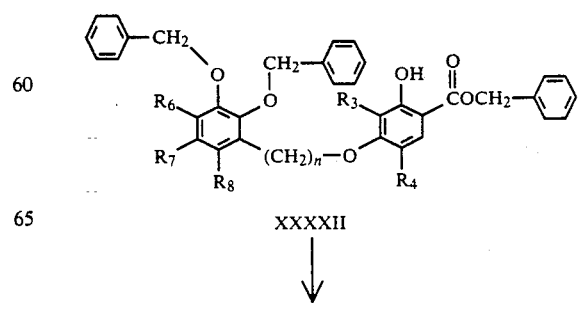

-continued
REACTION SCHEME XI

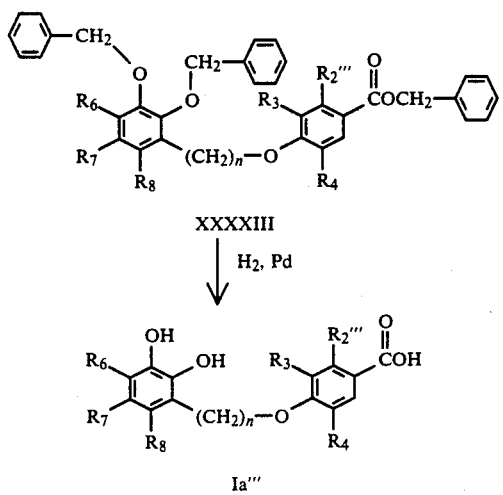

wherein $R_3$, $R_4$, $R_6$, $R_7$, $R_8$ and n are previously described and $R_2'''$ is alkanoyloxy.

In Reaction Scheme XI, a compound of formula XXXXII can be converted to the corresponding alkanoyl derivative of formula XXXXIII by treatment with a lower alkyl carboxylic acid anhydride in the presence of an organic base such as pyridine at a temperature in the range of from about 25° to about 70°.

A resulting compound of formula XXXXIII can be converted to a compound of formula Ia''' by hydrogenolysis, for example, by shaking in a hydrogen atmosphere under pressure or at atmospheric pressure at a temperature in the range of from about 25° to about 70° in the presence of a catalyst such as palladium in a solvent such as ethyl acetate, tetrahydrofuran or the like.

REACTION SCHEME XII

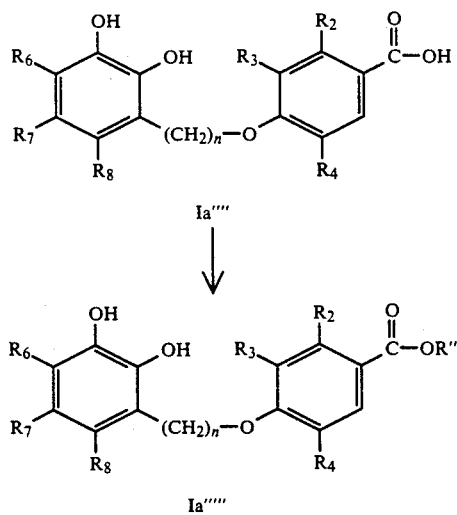

wherein $R_2$, $R_3$, $R_4$, $R_6$, $R_7$, $R_8$ and n are as previously described, and R" is lower alkyl or $-(CH_2)_n-N-(-$lower alkyl$)_2$, provided that $R_2$ is other than carboxy.

A lower alkyl ester or basic ester of formula Ia''''', and if desired the corresponding compound of formula Ib, where $R_5$ is H can be prepared by Scheme XII.

More particularly, to prepare a lower alkyl ester of formula Ia''''' a compound of formula Ia, wherein $R_1$ or $R_2$ is

that is, a compound of formula Ia'''', is reacted with a lower alkyl iodide in a solvent such as acetone, dimethylformamide or the like in the presence of an alkali metal bicarbonate, such as sodium bicarbonate or potassium bicarbonate at a temperature in the range of from about 30° to about 70° to yield the corresponding compound of formula Ia'''''.

To prepare a basic ester of formula Ia''''', a compound of formula Ia wherein $R_1$ or $R_2$ is

that is, a compound of formula Ia'''', is reacted with di-lower-alkylamino-lower-alkyl chloride in a solvent such as dimethylformamide, tetrahydrofuran or the like in the presence of an alkali metal bicarbonate, such as sodium bicarbonate or potassium bicarbonate at a temperature in the range of from about 30° to about 70° to yield the corresponding compound of formula Ia'''''.

It is understood that preferably any intermediate prepared in Reaction Schemes I-XII is recovered and isolated utilizing known procedures, for example, precipitation, crystallization, chromatography or the like, prior to use in the next reaction step. The end-products of formula I are recovered by similar known procedures.

The invention also relates to salts of the compound of formula I, when R is hydrogen, which salts are prepared by the reaction of the said acids with a base having a non-toxic, pharmacologically acceptable cation. In general, any base which will form a salt with a carboxylic acid and whose pharmacological properties will not cause an adverse physiological effect is within the scope of this invention. Suitable bases thus include, for example, the alkali metal and alkaline earth metal hydroxides, carbonates, and the like, for example, calcium hydroxide, sodium hydroxide, sodium carbonate, potassium carbonate and the like, ammonia, primary, secondary and tertiary amines, such as monoalkylamines, dialkylamines, trialkylamines, for example, methylamine, diethylamine, triethylamine and the like, nitrogen containing heterocyclic amines, for examples, piperidine and the like. A salt thus produced is the functional equivalent of the corresponding compound of formula I wherein R is hydrogen and one skilled in the art will appreciate that the variety of salts embraced by the invention is limited only by the criterion that a base employed in forming the corresponding salts be both non-toxic and physiologically acceptable.

The invention also relates to addition salts of the compounds of formula I, when R is $-(CH_2)_n-N-(-$lower alkyl$)_2$, which salts are prepared by the reaction of said amines with a non-toxic pharmacologically or pharmaceutically acceptable acid. In general, the referred to compounds of formula I form pharmaceutically acceptable addition salts with, for example, both pharmaceutically acceptable organic and inorganic acids, such as, acetic acid, succinic acid, formic acid, methanesulfonic acid, p-toluenesulfonic acid, hydrochloric acid, nitric acid, phosphoric acid, sulfuric acid and the like.

It is known that oxidative metabolism of arachidonic acid by the $\Delta^5$-lipoxygenase ($\Delta^5$—LO) pathway leads to the peptidoleukotrienes ($LTC_4$ and $LTD_4$) and leukotriene $B_4$ ($LTB_4$). $LTC_4$ and $LTD_4$ are potent bronchoconstrictors of human bronchi and contribute to edema in some species by increasing capillary permeability. $LTB_4$ is a potent chemotactic factor for inflammatory cells. $LTB_4$ has also been found in synovial fluid from patients with rheumatoid arthritis and gout and may be a mediator of inflammation and joint destruction in these diseases. Consequently, inhibitors of $\Delta^5$—LO may be of therapeutic value in the treatment of asthma and inflammatory diseases.

Furthermore, products of the $\Delta^5$—LO pathway ($LTB_4$, $LTC_4$, $LTD_4$) are present in elevated levels in skin lesions of patients with psoriasis and atopic dermatitis and may be mediators of these skin diseases. The intracutaneous application of $LTB_4$ to human skin gives a wheal and flare reaction followed by infiltration of neutrophils into the site of application. The influx of neutrophils is also observed during the inflammatory reactions associated with psoriatic lesions. Topical application of $LTB_4$ to human skin causes abscesses similar to those of pustular psoriasis.

Oxygen - derived free radicals and their metabolites may contribute to the irreversible injury which occurs on reperfusion of previously ischemic myocardial tissue. Therapy directed toward the toxic effects of these free radicals by radical scavenging drugs may provide protection against this injury.

The compounds of formula I exhibit activity, for example, as antioxidants, as $\Delta^5$-lipoxygenase inhibitors, and as hereinafter further described. The useful pharmacological activities of the compound of formula I can be demonstrated by the tests hereinafter set forth.

The compounds of formula I are useful as agents for the treatment of inflammatory diseases such as arthritis; inflammatory bowel disease such as colitis and as hereinafter further described; cardiovascular diseases such as myocardial ischemia; as anti-inflammatory agents in the topical therapeutic treatment of leukotriene-mediated dermal inflammations including psoriasis; and bronchopulmonary diseases such as asthma.

Inflammatory bowel disease (IBD) includes a variety of diseases of the gastrointestinal (GI) tract such as Crohn's disease of the colon and ileum, ulcerative colitis and pseudomembraneous colitis. Common symptoms of these diseases include inflammation of the affected area of the GI mucosa, mucosa ulceration, edema, infiltration of the mucosa with inflammatory cells and severe diarrhea. Arachidonic acid metabolites from the $\Delta^5$—LO pathway are believed to mediate IBD.

IN VITRO TEST FOR $\Delta^5$-LIPOXYGENASE INHIBITORS

Compounds of formula I of the invention were tested for their effect on $\Delta^5$-lipoxygenase from rat basophilic leukemia (RBL-1) cells.

Materials

RBL-1 cells (CRL 1378) were obtained from the American Type Culture Collection, Rockville, MD. DMEM and glutamine were purchased from Flow Labs, McLean, Va. FBS (Gibco, Grand Island, N.Y.) was heat-inactivated for 1 hour at 56° C. Reagents for protein determinations were obtained from Biorad, Rockville Center, N.Y. Arachidonic acid (approx. 99%), ATP (disodium salt), BHT, dextran (clinical grade), tetrasodium EDTA, gelatin, gentamycin sulfate solution, reduced glutathione, 1 M HEPES buffer, indomethacin, NaCl, reduced NADPH, Trizma 7.2, and Trizma 8.5 were purchased from Sigma Chemical, St. Louis, Mo. $CaCL_2$ dihydrate, Norit A charcoal, and citric acid monohydrate were obtained from Fisher Scientific, Pittsburgh, Pa. [$^3H$]-5-HETE (specific activity 229.5 Ci/mmol) was purchased from New England Nuclear, Boston, Mass. A synthetic 5-HETE standard was supplied by Dr. M. Rosenberger, Dept. of Medicinal Chemistry, Hoffmann La-Roche, Nutley, N.J.; [see Corey, E. J., and Hashimoto, S. (1981) Tet. Letters, 22, 299-302 for method of preparation]. Ecoscint liquid scintillation fluid was purchased form National Diagnostics, Sommerville, N.J.

Isolation of 5-lipoxygenase

The most stable enzyme preparations were obtained from RBL-1 cells thawed from liquid $N_2$ storage, then maintained in tissue culture flasks containing DMEM supplemented with 25 mM glucose, 12.5 mM HEPES, 40 mM glutamine, 50 ug/ml gentamycin sulfate, and 10% heat-inactivated FBS. Approximately 7-9 days after thawing, RBL-1 cells growing in log phase were seeded at a density of 7500 viable cells/ml in a closed 89-liter spinner flask. The cells were stirred constantly for 3-4 days at 37° C. until they reached a density greater than 500,000/ml but less than 800,000/ml. RBL-1 cells were harvested by centrifugation at 4° C. at $1500 \times g$ for 10 minutes and were washed 3 times with ice cold 0.05M tris-hCl, pH 7.2, tetrasodium EDTA (buffer 1). The cells were washed last in 0.05M Tris-HCl containing 14 $\mu$M indomethacin, 1 mM glutathione, 1.5 mM NaCl, and 1 mM tetrasodium EDTA (buffer 2), resuspended at a density of $5 \times 10^8$'/ml approximately 10 ml) and disrupted manually at 4° C. using a 40 ml Dounce (type A pestle) homogenizer. After 5 minutes of homogenization, 95% cell lysis was confirmed by phase contrast microscopy. The broken cells were diluted 1:2 with buffer 2 and centrifuged at $12,380 \times g$ for 10 minutes at 4° C. to pellet cellular debris and granules. The $12,380 \times g$ supernatant was centrifuged at $113,000 \times g$ for 60 minutes to pellet microsomes. The high-speed supernatant ($5.9 \pm 0.48$ mg/ml protein) was frozen immediately in 1 ml aliquots using a dry ice/acetone bath. The isolated cytosolic fraction was stored in liquid $N_2$ for up to 8 weeks without loss of 5-LO enzyme activity.

Lipoxygenase Assay

Compounds were dissolved at 25 mM concentration in DMSO, then diluted to final concentrations using 95% ethanol. For a typical enzyme assay, the partially purified 5-LO preparation was preincubated with drug or vehicle for 10 minutes at 30° C. The assay tubes were then transferred at a 37° C. water bath where they received arachidonic acid (8.25 $\mu$M final concentration) to initiate 5-LO activity. In addition to enzyme and substrate, each reaction tube contained: 12.5 $\mu$moles of Tris-HCl (pH 7.2), 25 $\mu$moles glutathione, 1.4 $\mu$moles indomethacin, and 1.25 $\mu$moles of $CaCl_2$ and ATP to yield a total volume of 250 $\mu$l 0.3M citric acid to yield pH 3.5. The samples were immediately cooled on ice and neutralized by dilution with 0.05M Tris-HCl, pH 8.5, which contained 25 mg/l BHT. A boiled cytosol control was placed at the end of each assay to emasure non-enzymatic oxidation of arachidonic acid. The mean specific activity of the 5-LO enzyme preparation was approximately 66.16±14.39 pmol 5-HETE 1 min/mg protein.

Radioimmunoassay for 5-HETE

Under the assay conditions described, the 5-LO catalyzed the conversion of arachidonic acid to 5-HPETE which, as a consequence of peroxidase activity, was reduced to 5-HETE. A specific radioimmunoassay was employed to quantitate the amount (pmoles) of 5-HETE formed during the enzyme reaction. To prepare the immunogen, Dr. M. Rosenberger (Dept. of Medicinal Chemistry) converted the racemic 5-HETE lactone (Corey, E. J., and Hashimoto, S. (1981) Tet. Letters, 22, 299–302) to its hydrazine derivative. The hydrazide was conjugated to thiolated Keyhole Limpet Hemocyanin (Young, R. N., Kakushima, M., and Rokach, J. (1982) Prostaglandins 23, 603–613) using N-ethyl-maleimide as previously described for $LTB_4$ by (Young, R., N, Zomboni, R. and Rokach, J. 91983) Prostaglandins, 26, 605–613). New Zealand White rabbits received multiple intradermal injections on their backs with 100 °g conjugate emulsified in complete Freund's adjuvant. A schedule of injections reported by Salmon (Salmon, J. A. (1978) Prostaglandins, 15, 383–397) was followed. After the monthly i.p. booster injections, blood was obtained from the marginal ear vein 5–7 days later and assessed for antibody titer.

Rabbit 5-HETE anti-sera was diluted 1:300 in RIA buffer (50 mM Tris-HCl plus 1.5 mM NaCL, pH 8.6, containing 0.1% gelatin) and aliquots were mixed with standard (0.75–25 pmole 5-HETE/ml) or dilute assay samples and placed in an ice bath. [$^3$H]-5-HETE (approximately 10,000–12,000 cpm) was added to yield a total assay volume of 300 °l. After a 90 minute incubation at 25° C., 1 ml ice-cold dextran-coated charcoal was added to separate antibody-bound from unbound 5-HETE (Salmon, J. A. (1978) Prostaglandins, 15, 383–397). The charcoal was sedimented at 2000×g for 10 minutes, after which 0.8 ml of supernatant was added to 10 mls Ecoscint fluid. Radioactivity (dpm) was determined after 10 minute counts using a LKB model 1219 scintillation counter (40% efficiency for [$^3$H].

Data Analysis

Each inhibitor concentration was tested in quadruplicate. The inhibitory concentration that yielded a 50% inhibition (IC-50) of control 5-HETE formation was calculated by regression analysis of the dose-response data. Data (IC-50) for the compounds of this invention in this test is reported in Table I.

Carrageenan Pleurisy Test (In Vivo)

The animals utilized in these studies were male Lewis rats (Charles River Breeding Laboratories) weighing between 230–250 g. Carrageenan (CG) pleurisy was induced by injecting 0.2 ml of 1% lambda carrageenan (Sigma Lot #60F-0652) dissolved in sterile, pyrogen free, saline into the right pleural cavity of the rat using a 26 gauge (⅜") intradermal needle. Compounds suspended in aqueous suspending vehicle (ASV, 0.5% carboxymethylcellulose containing 0.9% NaCl, 0.37% Tween 80, and 0.85% benzyl alcohol) were administered by intubation 1 hour before CG injection for the 5 hour treatment period and 1 hour before and 5 hour after CG injection for the 24 hour treatment period.

Drugs were administered at doses which, on the basis of preliminary experiments, would significantly suppress the development of CG-induced pleurisy under our experimental conditions.

At 5 or 24 hours after CG injection, the rats were killed by decapitation, exsanguinated, and the pleural cavity exposed by cutting the ribs on both sides of the sternum. The exudate fluid was removed from the pleural cavity with disposable plastic pipettes and its volume quantitated. The pleural cavity was then washed once with phosphate buffered saline containing fetal bovine serum (1:1) and the washings combined with the exudate. The total number of cells in the pleural cavity was quantitated using a Coulter Counter (Model ZM) adjusted to exclude any contaminating RBC. (Published in "Plant Flavonoids in Biology & Medicine: Biochemical, Pharmacological and Structure-Activity Relationships" p. 231–242 (1986) Alan R. Liss, Inc.)

Data for the compounds of this invention in this test is reported in Table I.

Mouse Ear Edema Test (In Vivo)

In this animal model system, the application of arachidonic acid to the ear results in the biosynthesis of the metabolic products 5-hydroperoxy-6,8,11,14-eicosatetraenoic acid (5-HETE), leukotriene $B_4$ ($LTB_4$), leukotriene $C_4$($LTC_4$), 12-hydroperoxy-5,8,10,14-eicosatetraenoic acid (12-HETE), and prostaglandin $E_2$ ($PGE_2$) at the site of application, followed by the influx of neutrophils into the site and the rapid development of edema within 30 to 60 minutes (See, for instance, Young, Wagern and Spries, "Tachyphylaxis in 12-O-Tetradecanoylphorbol Acetate And Arachidonic Acid-Induced Ear Edema", J. Invest. Dermatol. 80:48 (1983) and Hames, Opas and Bonney, "Arachidonic Acid Metabolites in Mouse Ear Edema" Advances in Inflammation Research, 11:57 (1986). Inhibitors of these metabolites and of their metabolic pathways also inhibit edema formation.

CD-1 male mice weighing 15 to 25 g were employed, and they were designated as follows: (1) Control Group, in which no arachidonic acid or test compound was to be applied, (2) Arachidonic Acid-Treated Group, in which no test compound was to be applied, and (3) Treated Group, in which the test compound was to be applied first, followed by the application of arachidonic acid.

In the case of the Group (3) animals, the test compound, dissolved in acetone, was applied to the dorsal surface of the right ear of the mouse with a 25-microliter pipettor, with the dose of the test compound being varied. After 0.5 hours in some cases and 4 hours in others, the arachidonic acid was topically applied in the same manner as above to the pretreated ear areas. In each case of arachidonic acid application, an amount of 0.5 mg dissolved in 25 microliters of acetone was used. After 1 hour, the mice were sacrificed by carbon dioxide inhalation. A 6 mm-diameter standard biopsy punch was used to obtain a uniform tissue sample from the ear of each mouse so treated, and the tissue samples were weighed to the nearest 0.1 mg. The percent inhibition of ear edema formation was calculated as follows:

$$\frac{\text{Wt. of Arachidonic Acid Group} - \text{Wt. of Testing Group}}{\text{Wt. of Arachidonic Acid Group} - \text{Wt. of Control group}} \times 100$$

Data for compounds of this invention in this test is reported in Table I.

TABLE I

| Name | Inhib. of $\Delta^5$ Lipoxygenase IC$_{50}$ ($\mu$M) | Rat Carrageenan Pleurisy % Inhib. of Exudate Volume at 100 mg/kg p.o | Mouse Ear Edema % Inhibition at 1 mg Topically |
|---|---|---|---|
| 4-[4-(2,3-dihydroxyphenyl)butoxy]-2-hydroxy-3-propylbenzoic acid | 0.09 | 76 | 17 |
| 4-[5-(2,3-dihydroxyphenyl)pentyloxy]-2-hydroxy-3-propylbenzoic acid | 0.006 | 63 | 0 |
| 4-[6-(2,3-dihydroxyphenyl)hexyloxy]-2-hydroxy-3-propylbenzoic acid | 0.02 | 68 | 46 |
| 4-[7-(2,3-dihydroxyphenyl)heptyloxy]-2-hydroxy-3-propylbenzoic acid | 0.005 | 57 | 57 |
| 4-[8-(2,3-dihydroxyphenyl)octyloxy]-2-hydroxy-3-propylbenzoic acid | 62% at 0.1 $\mu$M | 66 | 78 |
| 4-[10-(2,3-dihydroxyphenyl)decyloxy]-2-hydroxy-3-propylbenzoic acid | 0.02 | 61 | 49 |
| 4-[6-(2,3-dihydroxyphenyl)hexyloxy] 2-hydroxy-3-propylbenzoic acid ethyl ester | 100% at 1 $\mu$M | 44 | 64 |
| 4 [6-(2,3-dihydroxyphenyl)hexyloxy] 2-hydroxy-3-propylbenzoic acid [2-(diethylamino)ethyl]ester | 0.67 | 42 | 48 |
| 2 (acetyloxy-4-[6-(2,3-dihydroxyphenyl)hexyloxy]-3-propylbenzoic acid | 0.19 | 42 | Not Tested |
| 4-[6-[2,3-bis(acetyloxy)phenyl]hexyloxy]2-hydroxy-3-propylbenzoic acid | 0.15 | 43 (75 mg/kg) | Not Tested |
| 4-[6-[2,3-dihydroxy-4-(1-methylethyl)phenyl]hexyloxy]-2-hydroxy-3-propyl benzoic acid | 0.1 | 47 (75 mg/kg) | 45 |
| 4-[6-(2,3-dihydroxyphenyl)hexyloxy] benzoic acid | 0.17 | 46 | 48 |
| 4-[6-(2,3-dihydroxyphenyl)hexyloxy]-2-hydroxybenzoic acid | 0.32 | 0 | 50 |
| 4-[6-(2,3-dihydroxyphenyl)hexyloxy]-3-propylbenzoic acid | 0.02 | 0 | 52 |
| 4-[6-(2,3-dihydroxyphenyl)hexyloxy]-3,5-dipropylbenzoic acid | 0.46 | Not tested | 59 |
| 4-[3-(3,4-dihydroxyphenyl)propoxy]-2-hydroxy-3-propylbenzoic acid | 97 % at 1 $\mu$M | 55 | 32 |
| 4-[6-(3,4-dihydroxyphenyl)hexyloxy]-2-hydroxy-3-propylbenzoic acid | 0.005 | 0 | 21 |
| 4-[[6-(3,4-dihydroxyphenyl)-6-oxohexyl]oxy]-2-hydroxy-3-propylbenzoic acid | 51% at 1 $\mu$M | Not Tested | Not Tested |
| 1-[2-hydroxy-4-[6-(2,3-dihydroxyphenyl)hexyloxy]-3-propylphenyl]ethanone | 0.03 | 51 | 21 |
| 1-[2-hydroxy-4-[4-(2,3-dihydroxyphenyl)butoxy]-3-propylphenyl]ethanone | 48% at 0.01 $\mu$M | 53 | Not Tested |
| 1-[2-hydroxy-4-[8-(2,3-dihydroxyphenyl)octyloxy]-3-propylphenyl]ethanone | 95% at 0.1 $\mu$M | 0 | 0 |
| 1-[2-hydroxy-4 [6-[2,3 dihydroxy-4-(1-methylethyl)phenyl]hexyloxy]-3 propylphenyl]ethanone | 35% at 0.1 $\mu$M | | |
| 5-chloro-4 [6 (2,3 dihydroxyphenyl)hexyloxy] 2 hydroxy 3 propylbenzoic acid | 48% at 0.1 $\mu$M | 45 (50 mg/kg) | 51 |

Acetic Acid-Induced Colitis in Rats, In Vivo

The rat acetic acid-induced colitis bioassay has been described by J. E. Krawisz, et al. in Amer. J. Proc. Gastro. Col. Rec. Surg. 31: 11–18 (1980), and by P. Sharon and W. F. Stenson in Gastroenterolgy 88: 55–63 (1985) and 86: 453–460 (1984). Acetic acid-induced colitis is characterized by the movement of inflammatory cells into the colon, with the number of such cells in the mucosa being measured by the activity of myeloperoxidase, a marker enzyme for these cells. Positive desirable activity is indicated by a reduction in the high levels of myeloperoxidase caused by acetic acid. Male rats (Sprague-Dawley), weighing 150 to 300 g, were pretreated twice daily for two days with either the vehicle (water, or dimethylsulfoxide) or the test inhibitor compound suspended in water or dissolved in dimethylsulfoxide and orally administered. On the third day, the animals were dosed the same as on the previous two days, anesthetized with metofane, and 2 ml of 2.5% acetic acid was injected by syringe into the colonic lumen, followed immediately by 3 ml of air and a rinse consisting of 3 ml of phosphate-buffered saline (the acetic acid is present in the lumen for a sufficient period to cause inflammation without producing severe necrosis or irreversible damage). The animals were administered a second dose of the test compound in the same amount about 16 hours later. 24 hours after the acetic acid treatment, the animals were sacrificed, the colonic mucosa was surgically removed and homogenized in an aqueous buffer at pH 6 with a Tissumizer or similar device and myeloperoxidase was measured in the homogenate using o-phenylenediamine as a chromagen, as described by A. Voller, D. E. Bidwell and A. Bartlett in The Enzyme Linked Immunosorbent Assay (ELISA), Zoological Soc., London, 1979, pages 29–30. Control animals were pretreated with the vehicle and saline in place of acetic acid.

Data for representative compounds of this invention is reported in Table II.

Antibiotic-Induced Colitis in Hamsters, In Vivo

Male Syrian hamsters (LUG), weighing 80 to 120 g were each given a single dose of 175 mg/kg of clindamycin-phosphate or of clindamycin-hydrochloride intraperitoneally, to induce colitis. Approximately seven hours after injection, the animals were given the test compound orally or intraperitoneally and the therapy was continued twice a day for a period of four more days. For oral administration, the antibiotic was suspended in water or dissolved in dimethylsulfoxide and delivered to the animals by gavage using an oral intubating needle. The effect of the therapy was measured by use of the Hazard Ratio, which is the ratio of the mortality of the animals treated with the test inhibitor compound contained in a vehicle to the mortality of the animals treated with the vehicle containing none of the test inhibitor compound. The mortality was determined for the test inhibitor compound-treated groups and for the vehicle-treated groups, respectively, twice daily, and was evaluated by comparing the survival curves of each group. The Kaplan-Meier estimate of the survival curve was calculated for each group and the Mantel-Cox (logrank) test was used to compare the survival curve of each test inhibitor compound-treated (therapy) group to that of the corresponding vehicle control group. A Hazard Ratio of 1.0 indicates that the therapy has no better effect compared with the vehicle alone, while a Hazard Ratio greater than 1.0 ($>1.0$) indicates that the therapy prolongs survival in comparison with the group treated with the vehicle alone. (See, J. G. Bartlett et al. Amer. J. Vet. Res. 39: 1525–1530 (1978)).

Data for representative compounds of this invention are reported in Table II.

TABLE II

| | Rat Acetic Acid Colitis Model | | Hamster Colitis Model | |
|---|---|---|---|---|
| Name | Dose (mg/kg p.o) | % Inhib. of Myeloperoxidase Accumulation | Dose (mg/kg p.o) | Hazard Ratio |
| 4-[4-(2,3-dihydroxyphenyl)butoxy]- 2-hydroxy-3-propylbenzoic acid | 10 | 73 ± 10 | 10 | 1.35 |
|  | 30 | 71 ± 11 | 100 | 0.1 |
| 4-[6-(2,3-dihydroxyphenyl)hexyloxy]- 2-hydroxy-3-propylbenzoic acid | 10 | 42 ± 2 | 10 | 2.26** |
|  | 30 | 67 ± 15 | 100 | 4.22** |
| 4-[8-(2,3-dihydroxyphenyl)octyloxy]- 2-hydroxy-3-propylbenzoic acid | 10 | 35 ± 7 | | |
|  | 100 | 27 ± 3 | | |
| 4-[6-[2,3-dihydroxy-4-(1-methylethyl) phenyl]hexyloxy]-2-hydroxy-3-propyl benzoic acid | 10 | 53 ± 12 | | |
|  | 100 | 86 ± 9 | | |
| 1-[2-hydroxy-4-[4-(2,3-dihydroxyphenyl) butoxy]-3-propylphenyl]ethanone | 10 | 46 ± 7 | | |
|  | 30 | 89 ± 11 | | |
| 4-[6-(2,3-dihydroxyphenyl)hexyloxy]- 2-hydroxybenzoic acid | 1 | 82 ± 9 | | |
|  | 3 | 81 ± 15 | | |
| 4-[6 (2,3 dihydroxyphenyl)hexyloxy] benzoic acid | 3 | 79 ± 8 | | |
|  | 10 | 89 ± 28 | | |
| 4-[6-(2,3-dihydroxyphenyl)hexyloxy]- 2-hydroxy-3 propylbenzoic acid ethyl ester | 1 | 40 ± 9 | | |
|  | 3 | 67 ± 11 | | |
| 4-[6-(3,4-dihydroxy-2,5-dimethyl- phenyl)hexyloxy]-2-hydroxy-3- propylbenzoic acid | 3 | 37 ± 6 | | |
|  | 10 | 85 ± 13 | | |
| 4-[3-(2,3-Dihydroxyphenyl)propoxy]- 2-hydroxy-3-propylbenzoic acid | 10 | 54 ± 5 | | |
| 4-[5 (2,3 Dihydroxyphenyl)pentyloxy] 2-hydroxy 3 propylbenzoic acid | 1 | 96 ± 13 | | |
| 5 Chloro 4 [6 (2,3 dihydroxyphenyl) hexyloxy] 2-hydroxy-3-propylbenzoic acid | 30 | 44 ± 6 | | |
| 4 [3-(3,4 Dihydroxyphenyl)propoxy] 2 hydroxy 3 propylbenzoic acid | 30 | 39 ± 5 | | |
| 4 [2 (3,4 Dihydroxyphenyl)ethoxy]- 2 hydroxy 3 propylbenzoic acid | 10 | 56 ± 6 | | |
| 4-[[6-(2 Fluoro 4,5 dihydroxyphenyl) 6 oxohexyl]oxy 2 hydroxy 3 propyl benzoic acid | 10 | 40 ± 5 | | |
| 1-[4-[6-(2,3-Dihydroxyphenyl)hexyloxy] | 10 | 51 ± 5 | | |
| 1-[4-[6-(2,3-Dihydroxy-4-(1-methylethyl) phenyl]hexyloxy-2-hydroxy-3-propylphenyl] ethanone | 10 | 65 ± 10 | | |
| 1-[4-[5-(3,4-Dihydroxyphenyl)pentyloxy]- 2-hydroxy-3-propyl]ethanone | 10 | 52 ± 6 | | |
| 4-[5-(2-Chloro-5,6-dihydroxyphenyl)penty- loxy]-2-hydroxy-3-propylbenzoic acid | 3 | 54 ± 9 | | |
| 4-[5-(2,3-Dichloro-5,6-dihydroxyphenyl) pentyloxy]-2-hydroxy-3-propylbenzoic acid | 1 | 73 ± 5 | | |
| 4 [5-(2,3,4 Trichloro-5,6-dihydroxy- phenyl)pentyloxy] 2 hydroxy 3 propyl- benzoic acid | 1 | 115 ± 21 | | |
| 3-Amino-4-[6-(2,3-dihydroxyphenyl) | 1 | 55 ± 7 | | |

TABLE II-continued

| | Rat Acetic Acid Colitis Model | | Hamster Colitis Model | |
|---|---|---|---|---|
| Name | Dose (mg/kg p.o) | % Inhib. of Myeloperoxidase Accumulation | Dose (mg/kg p.o) | Hazard Ratio |
| hexyloxy]benzoic acid | | | | |

**p < 0.01

In Vitro, Testing of Antiperoxidative Agents

The test system employs hypoxanthine-xanthine oxidase (XO)-$Fe^{3+}$·ADP as the free radical generator and purified, native rat-heart membrane phosphoglyceride in Hepes-KCl buffer, pH 7.4, as the substrate. Inhibition of superoxide-dependent, iron-promoted lipid peroxidation in the linear reaction phase (after 1 hour of reaction) is measured as the net formation of thiobarbituric acid (TBA)-reactive material. In this system, the TBA-reactive material, isolated by HPLC, is exclusively (>95%) malondialdehyde (MDA), a fragmentation end-product arising from fatty acyl hydroperoxides and cyclic endoperoxides.

(a) Isolation and Purification of Rat Cardiac Lipid

Conscious male Sprague-Dawley rats (~275 g) maintained on a normal rodent diet were decapitated. The hearts were rapidly removed and perfused via the aorta with ice-cold 10 mM Hepes buffer, pH 7.4. The aorta and atria were removed, and the ventricular tissue was blotted and weighed (wet weight). The hearts were minced on ice with scissors and finally homogenized (100 mg tissue/ml ice-cold buffer) for 15 seconds (3×5 seconds) with a Tekmar Tissumizer at "maximal" setting. The homogenate was filtered through 4-ply cheesecloth, and homogenate lipids were extracted and purified by a modified Bligh-Dyer procedure (M. D. Marshall and M. Kates; Biochem. Biophys. Acta 260, 558 (1972). The cardiac lipids were stored in $CHCl_3$ under nitrogen at −20° C.

(b) Preparation of Cardiac Liposomes

Liposomes were prepared from extracted and purified, native rat heart cardiac lipid and were used as substrate for free-radical attack. Cardiac lipid (in $CHCl_3$) was placed in a glass flask and evaporated to dryness under nitrogen at room temperature; the flask was gently rotated during evaporation to yield a thin, dry lipid film. The lipid was taken up in 10 mM Hepes-0.145M CKl, pH 7.4, and was resuspended by indirect anaerobic sonication for 15 minutes at room temperature. The liposome suspension was used immediately.

(c) Preparation of $Fe^{3+}$-ADP chelate

A chelate was formed in Hepes-KCl buffer between $Fe^{3+}$ (1.0 mM $FeCl_3$, final concentration) and ADP (10 mM, final concentration) at pH 7.4 with stirring at room temperature. Chelation was allowed to proceed for 90 minutes prior to use. The chelate was prepared fresh for each days experiments to ensure iron solubility, effective chelation, and valence state.

(d) Thiobarbituric Acid Reaction for Determination of Malondialdehyde Equivalents Malondialdehyde (MDA) equivalents were measured as thiobarbituric acid (TBA)-reactive material by the following modification of published methods. The reaction mixture, prepared fresh daily, contained water:BHT (7.1M BHT in absolute ethanol):TBA (1.5% TBA in 0.2M Tris, pH 7.0) in the volume ratio 1:1:5. To each 1.0 ml of peroxidation reaction assayed (see below), 0.35 ml reaction mixture was added. After thorough mixing, the tubes were incubated in an 80° C. shaking water bath for 30 minutes. After this time, the tubes were plunged into an ice water bath, and the reaction was immediately stopped with 0.5 ml ice-cold 91% TCA followed by 2.0 ml $CHCl_3$. After centrifugation for 30 minutes at 2000 rpm in a Sorval HL-8 rotor (4° C.), the absorbance of the washed, pink upper phase was read at 532 nm. A standard curve (0.8–40.0 nmol MDA) was run with every assay. For each curve, MDA was freshly prepared by acidification of 1,1,3,3-tetraethoxypropane with 75% TCA-2.3N HCl (0.15 ml acid mixture with 1.0 ml suitably diluted tetraethoxypropane). Computer-assisted regression analysis of the standard curve was used to quantify the molar amounts of MDA equivalents in the experimental samples.

(e) Lipid Peroxidation Reaction

Cardiac liposomes were subjected to superoxide-dependent, iron-promoted peroxidation in glass vessels to avoid the well-known antioxidant effects of many common polymerizing agents used to fabricate plastic labware. Screening was performed in triplicate in glass 12×75 mm tubes at a final reaction volume of 1.0 ml and a reaction time of 60 minutes. Per milliliter of peroxidation reaction, the components were: Tris-KCl buffer (0.1 ml), cardiac liposomes (0.5 ml, equivalent to 125 µg phospholipid), 1 mM HX (0.1 ml), 0.1 mM $Fe^{3+}$−1.0 mM ADP chelate (0.1 ml), test substance (0.1 ml solubilized in Tris-KCl, ethanol, or DMSO) and 10 mU XOD (0.1 ml). All components are listed at their final concentrations and were prepared at the time of assay. The peroxidation reaction was started with the addition of XOD and was carried out at 37° C. in a shaking water bath. Peroxidation was terminated by adding 0.15 ml ice-cold 76% TCA-2.3N HCl for each 1.0 ml of peroxidation reaction to be assayed for MDA equivalents (above). To check for possible interference by test substance, a second set of samples was run, but in these the peroxidation reaction was stopped immediately with the TCA-HCl mixture. Test substances were screened at 1.0 µM final concentration. If peroxidation were inhibited by ≧50%, an $IC_{50}$ value was determined.

For kinetic studies, peroxidation was carried out in glass Erlenmeyer flasks. At each desired time, 1.0 ml samples, in triplicate, were withdrawn into iced tubes containing 0.15 ml 76% TCA-2.3N HCl and were then reacted with TBA (above).

(f) Calculation of the Effect of a Test Substance on Lipid Peroxidation

The effect of a test substance on cardiac lipid peroxidation during the 60 minute screening assay was taken as the ratio between the end MDA equivalents produced in the presence of the drug and the net MDA equivalents produced in its absence. The percent inhibition of lipid peroxidation was calculated by:

$$\% \text{ Inhibition of peroxidation} = 1 - \frac{Drug_{60'} - Drug_{0'}}{T_{60'} - T_{0'}} \times 100$$

$Drug_{60'}$ = MDA equivalents produced after 60 minutes with the free radical generator + test substance.
$Drug_{0'}$ = MDA equivalents produced after 0 minutes with the free radical generator + test substance
$T_{60'}$ = Total MDA equivalents produced without test substance at 60 minutes.
$T_{0'}$ = Endogenous TBA reactivity of reaction mixture at 0 minutes.

Data for the compounds of this invention in this test is reported in Table III.

In Vivo Testing of Antiperoxidative Agents

In this preparation a free radical generating (FRG) system consisting of purine (2.3 mM), xanthine oxidase (0.02 U/ml) and iron loaded transferring (0.6 μM) complex is infused into the carotid artery near the ostium of the coronary artery in spontaneously hypertensive rats. Blood is withdrawn before and 24 hours after the FRG challenge for measuring the isoenzymes of lactic acid dehydrogenase ($LDH_1:LDH_2$). An increase in $LDH_1:LDH_2$ ratio reflects cell damage to the myocardium. The electrocardiogram is also taken before and 24 hours after the FRG infusion. At the end of the experiment the heart is removed, sliced in a breadloaf fashion, and stained with triphenyltetrazolium chloride to determine infarct size. A drug or vehicle is administered intravenously 10-30 minutes before the FRG challenge. A drug is considered active if there is no elevation of the $LDH_1:LDH_2$ ratio, no ECG abnormalities and no histologic evidence of an infarction.

Rat In Vivo Model of Myocardial Ischemia

Male spontaneously hypertensive rats (280-320 g) from Taconic Farms, were lightly anesthetized with sodium pentobarbital (30-50 mg/kg, i.p.). Rats exhibiting abnormal patterns prior to surgery were eliminated from the study. A catheter of PE 50 tubing was inserted into the right common carotid artery to a position proximal to the ostia of the coronary arteries and used to sample blood and infuse the free radical generator (FRG) system. A second catheter of PE 10 tubing was inserted into the left jugular vein to administer drugs. The infusion system for the FRG consisted of a double syringe infusion pump, Sage Model 351, with one syringe containing xanthine oxidase (0.01 units/ml) in a HEPES (0.05M) buffer and the other syringe containing purine (2.3 mM) plus $Fe^{3+}$ loaded transferring (0.06 μM) in a HEPES (0.05M) buffer. The FRG infused separately mixes simultaneously near the ostia of the coronary arteries. This infusion was delivered at a rate of 0.03 ml/minute for a total infusion time of 10 minutes. The drugs were infused over a one minute period in a 0.9% saline vehicle.

Standard Lead II ECG was monitored continuously on a Hewlett-Packard 7758A recorder prior to treatment, throughout the FRG infusion and 10 minutes post infusion. Catheters were removed and animals were allowed to recover and fed standard rat chow and water ad libitum. 24 hours following the FRG infusion, animals were reanesthetized with sodium pentobarbital (30-50 mg/kg, i.p.) and an ECG was obtained. Blood samples were taken prior to and after the FRG infusion and at the conclusion of the experiment. These samples were centrifuged and assayed for total lactate dehydrogenase (LDH) and lactate dehydrogenase isoenzymes ($LDH_1:LDH_2$), using electrophoresis.

The animals were sacrificed, the hearts rapidly excised, and washed free of blood and sectioned. The left ventricle was weighed and stored in a Revco ® freezer at −70° C. The left ventricle was sliced into 2 mm-thick rings, incubated in a 1% triphenyltetrazolium chloride solution for 20 minutes, and then fixed in a 10% formalin solution. Infarcted areas were measured and quantitated as a percentage of the total left ventricular volume.

Data for the compounds of this invention in this test is reported in Table III.

TABLE III

| Name | Inhib. of Lipid Peroxidation $IC_{50}$ (μM) | Rat Ischemia Model 10 mg/kg iv | |
|---|---|---|---|
| | | Infarcts/ Total | % Infarction* |
| 4-[4-(2,3-dihydroxyphenyl)butoxy]-2-hydroxy-3-propylbenzoic acid | 0.5 | 2/5 | 8 |
| 4-[5-(2,3-dihydroxyphenyl)pentyloxy]-2-hydroxy-3-propylbenzoic acid | 0.4 | 4/5 | 15 |
| 4-[6-(2,3-dihydroxyphenyl)hexyloxy]-2-hydroxy-3-propylbenzoic acid | 0.3 | 4/5 | 8 |
| 4-[7-(2,3-dihydroxyphenyl)heptyloxy]-2-hydroxy-3-propylbenzoic acid | 0.5 | 3/5 | 18 |
| 4-[8-(2,3-dihydroxyphenyl)octyloxy]-2-hydroxy-3-propylbenzoic acid | 0.3 | 1/5 | 8 |
| 4-[10-(2,3-dihydroxyphenyl)decyloxy]-2-hydroxy-3-propylbenzoic acid | 0.4 | 3/3 | 13 |
| 4-[6-[2,3-dihydroxy-4-(1 methylethyl)phenyl]hexyloxy]-2-hydroxy-3-propyl benzoic acid | 0.7 | 1/5 | 5 |
| 4-[6-(2,3-dihydroxyphenyl)hexyloxy] benzoic acid | >1 | 2/5 | 19 |
| 4-[6-(2,3-dihydroxyphenyl)hexyloxy]-2-hydroxy benzoic acid | >1 | 3/5 | 10 |
| 4-[6-(3,4-dihydroxyphenyl)hexyloxy] 2-hydroxy-3 propylbenzoic acid | 0.6 | 1/5 (5 mg/kg iv) | 11 |
| 1-[2-hydroxy-4-[6-(2,3-dihydroxy phenyl)hexyloxy]-3-propylphenyl] ethanone | 0.7 | 4/4 | 24 |
| 1 [2-hydroxy-4 [4-(2,3-dihydroxy-phenyl)butoxy] 3 propylphenyl] | >1 | 1/5 | 12 |

TABLE III-continued

| Name | Inhib. of Lipid Peroxidation IC$_{50}$ (μM) | Rat Ischemia Model 10 mg/kg iv | |
|---|---|---|---|
| | | Infarcts/Total | % Infarction* |
| ethanone | | | |
| 1 [2 hydroxy 4 [6 [2,3-dihydroxy 4 (1 methylethyl)phenyl]hexyloxy] 3 propylphenyl]ethanone | 0.7 | 2/5 | 11 |

*Percent of left ventricle infarcted of the animals with an infarct.

A compound of formula I or a salt thereof or a composition containing a therapeutically effective amount of a compound of formula I or a salt thereof can be administered by methods well known in the art. Thus, a compound of formula I or a salt thereof can be administered either singly or with other pharmaceutical agents, orally, parenterally, rectally, or by inhalation, for example, in the form of an aerosol, micropulverized powder or nebulized solution. For oral administration the described compound can be administered in the form of tablets, capsules, for example, in admixture with talc, starch, milk sugar or other inert ingredients, that is, pharmaceutically acceptable carriers, in the form of aqueous solutions, suspensions, elixirs or aqueous alcoholic solutions, for example, in admixture with sugar or other sweetening agents, flavoring agents, colorants, thickeners and other conventional pharmaceutical excipients, or beadlets for oral administration. For parenteral administration, the desired compound can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the areosol composition. For rectal administration, the desired compound can be administered in the form of suppositories utilizing an inert carrier material cocoa butter and the like. For topical administration, the compounds of formula I can be incorporated into ointments, creams, lotions, gels, and the like. In general, the solutions, ointments and creams which are useful in accordance with this invention include formulations having absorbable, water soluble or emulsion-type bases, such as petrolatum, lanolin, polyethylene glycols, or the like.

Suitable solutions will contain the compounds of formula I dissolved in a pharmaceutically acceptable solvent, such as polyethylene glycol, or the like.

Suitable lotions include, true solutions to aqueous or hydroalcoholic formulations containing finely divided particles. Lotions can contain suspending or dispersing agents such as cellulose derivatives, for example, methyl cellulose, ethyl cellulose, or the like. Gels will typically be semi-solid preparations made by gelling a solution or suspension of a compound of formula I in a suitable hydrous or anhydrous vehicle, using a gelling agent such as a carboxy polymethylene, or the like, and thereafter neutralizing it to proper consistency with an alkali metal hydroxide, for example, sodium hydroxide, and an amine, for example, polyethylenecocoamine. Topical pharmaceutical compositions containing a compound of formula I can also be formulated to include conventional ingredients such as preservatives, stabilizers, wetting agents, emulsifying agents, buffers, and the like, in conventional amounts adjusted for particular requirements and which are readily determinable by those skilled in the art.

In the practice of the invention, the dose of a compound of formula I or a salt thereof to be administered and the frequency of administration will be dependent on the potency and duration of activity of the particular compound of formula I or salt to be administered and on the route of administration, as well as the severity of the condition, age of the mammal to be treated and the like. Oral doses of a compound of formula I or a salt thereof contemplated for use in practicing the invention are in the range of from about 25 to about 1000 mg per day, preferably about 25 to about 250 mg either as a single dose or in divided doses.

The Examples which follow further illustrate the invention. All temperatures set forth in the specification and the Examples are in degrees Centigrade. Melting points were taken on a Thomas Hoover capillary melting point apparatus and are uncorrected. All compounds were characterized by proton magnetic resonance spectra taken on a Varian XL-100 or SL-200 spectrometer and mass spectra taken on a CEC 21-110 mass spectrometer at 70 eV. Preparative high-pressure liquid chromatography (HPLC) was performed on silica gel Prep-Pak 500 cartridges using a Waters Associates Prep LC 500A. Extracts were dried over anhydrous magnesium sulfate unless otherwise noted.

EXAMPLE 1

1-(6-Bromohexyl)-2,3-dimethoxybenzene

A solution of 1.55M butyl lithium in hexane (195 mL, 0.3 mol) was added dropwise over 30 minutes to a stirred solution of 1,2-dimethoxybenzene (41.4 g, 0.3 mol) in 700 mL of anhydrous tetrahydrofuran at room temperature under argon. The reaction mixture was stirred and heated at 40° for 4 hours and then cooled to −70°. A solution of 46 mL (0.3 mol) of 1,6-dibromohexane in 250 mL of anhydrous tetrahydrofuran was added dropwise over 30 minutes. The cooling bath was removed and the reaction mixture was stirred for 1 hour and then heated at 40° for 4 hours. Most of the solvent was removed, 90 mL of 3N HCl was added and the product was extracted with hexane. The extract was washed with sodium bicarbonate solution, dried and concentrated under reduced pressure to yield an oil. Distillation gave 1-(6-bromohexyl)-2,3-dimethoxybenzene as a yellow oil (29 g, 32% yield, b.p. 125°–140°/0.15 mm).

This procedure is known and described for 1-(7-bromoheptyl)-2,3-dimethoxybenzene in the following reference: H. Halim, H. D. Locksley and J. J. Memon, J. Chem. Soc. Perkin I, 2331 (1980). It was used for the preparation of all of the bromo intermediates wherein n=3-10.

EXAMPLE 2

1-(6-Iodohexyl)-2,3-bis-(phenylmethoxy)benzene

Boron tribromide (266 mL, 0.266 mol, 1M in methylene chloride) was added dropwise over 1 hour to a cooled (−65°) solution of 40.0 g (0.133 mol) of 1-(6-bromohexyl)-2,3-dimethoxybenzene in 800 mL of anhydrous methylene chloride which was stirred in an argon atmosphere. The cooling bath was then removed and the reaction mixture was stirred for 1.5 hours. After cooling in an ice bath, 100 mL of water and 50 mL of 3N HCl were added and the mixture was stirred for 2 hours. The organic layer was separated, dried and concentrated under reduced pressure to an oil which was purified by HPLC using 5% methanol-chloroform to yield 34.7 g of 1-(6-bromohexyl)-2,3-dihydroxybenzene as an oil. To this was added 32 mL (0.28 mol) of benzyl chloride, 46 g (0.28 mol) of potassium iodide, 122 g (0.88 mol) of potassium carbonate and 700 mL of anhydrous acetone and the reaction mixture was stirred at reflux for 72 hours. The solid was removed by filtration and the filtrate was concentrated under reduced pressure to an oil which was purified by HPLC using 1% ethyl acetate-hexane to give 47 g (74% yield) of 1-(6-Iodohexyl)-2,3-bis-(phenylmethoxy)benzene as an oil. The nmr spectrum was consistent with the structure (CH$_2$I at δ3.14) and the mass spectrum showed the molecular ion at m/e 500 ($C_{26}H_{29}IO_2$).

EXAMPLE 3

1-[(2-Methanesulfonyloxy)ethyl]-2,3-dimethoxybenzene

To 20 g (0.145 mol) of 1,2-dimethoxybenzene in 300 mL of anhydrous tetrahydrofuran stirred at room temperature under argon was added 90 mL (0.145 mol) of 1.6M butyl lithium in hexane over 30 minutes. The reaction mixture was stirred and heated at 40° for 4 hours and then cooled in an ice bath. Ethylene oxide (14 mL, 0.29 mol) was allowed to distill into the ice cooled reaction mixture over 45 minutes. The reaction mixture was stirred with ice bath cooling for 1.5 hours and then at room temperature for 17 hours. Most of the solvent was removed under reduced pressure and water was added to the residue. The product was extracted with ether and the dried extract was concentrated under reduced pressure to an oil. The remaining 1,2-dimethoxybenzene (7.5 g) was removed by distillation (bp 45°-60°/0.2 mm) and the residue was purified by HPLC using 20% ethylacetate-toluene to give 5 g (19% yield) of 1-(2-hydroxyethyl)-2,3-dimethoxybenzene. This intermediate (5 g, 0.028 mol) was dissolved in 100 mL of anhydrous methylene chloride and the solution was cooled in an ice bath. Triethylamine (7.7 mL, 0.056 mol) was added and followed by 2.6 mL (0.033 mol) of methane sulfonyl chloride added dropwise. The reaction mixture was stirred with ice bath cooling for two hours and then was washed with water, with sodium bicarbonate solution, dried and concentrated under reduced pressure to give (7.2 g) of 1-[(2-methanesulfonyloxy)ethyl]-2,3-dimethoxybenzene as an oil which was used without purification.

EXAMPLE 4

1-(6-Bromohexyl)-2,3-bis[(4-methylbenzoyl)oxy]benzene

To 9.0 g (0.033 mol) of 1-(6-bromohexyl)-2,3-dihydroxybenzene in 200 mL of anhydrous tetrahydrofuran and 13.7 mL (0.099 mol) of triethylamine stirred in an ice bath was added 10.9 mL (0.082 mol) of 4-methylbenzoyl chloride dropwise over 30 minutes. After 30 minutes, the bath was removed and stirring was continued at room temperature for 2.5 hours. The reaction mixture was concentrated under reduced pressure, the residue was treated with sodium bicarbonate and the product was extracted with ether. The dried extract was concentrated to an oil which was purified by HPLC using 10% ethyl acetate-hexane to give 15.2 g (90% yield) of 1-(6-bromohexyl)-2,3-bis[(4-methylbenzoyl)oxy]benzene as an oil.

EXAMPLE 5

1-(6-Bromohexyl)-2,3-bis(acetyloxy)benzene

To 1.0 g (3.8 mmol) of 1-(6-bromohexyl)-2,3-dihydroxybenzene in 150 mL of ethyl acetate and 15 mL of acetic anhydride was added 0.03 mL of 70% perchloric acid. The solution was left at room temperature for 1.5 hours and then was washed with sodium bicarbonate solution. After drying, the organic layer was concentrated to give 1.3 g of 1-(6-bromohexyl)-2,3-bis(acetyloxy)benzene as an oil.

EXAMPLE 6

1-[(2-Methanesulfonyloxy)ethyl]-2,3-dimethoxybenzene

To 3.3 g (0.018 mol) of 3,4-dimethoxyphenethyl alcohol in 50 mL of methylene chloride and 4.2 mL (0.03 mol) of triethylamine cooled in an ice bath was added 1.6 mL (0.02 mol) of methanesulfonyl chloride with stirring. The reaction mixture was stirred for 75 minutes and then washed successively with water, 1N hydrochloric acid and sodium bicarbonate solution. After drying, the extract was concentrated under reduced pressure to give 1-[(2-methanesulfonyloxy)ethyl]-2,3-dimethoxybenzene as an oil.

EXAMPLE 7

1-(6-Bromo-1-oxohexyl)-3,4-dimethoxybenzene

A mixture of 1.0 mL (7.8 mmol) of 1,2-dimethoxybenzene and 2.0 g (10 mmol) of 6-bromohexanoic acid was warmed briefly until homogeneous and stirred while 1.7 mL (11.7 mmol) of trifluoroacetic anhydride was added. The reaction mixture was stirred at room temperature for 17 hours and then was poured into sodium bicarbonate solution. The product was extracted with ethyl acetate and the dried extract was concentrated to an oil which was purified by chromatography on 150 g of silica gel. Elution with 25% ethyl acetate-hexane gave 1.6 g (65% yield) of 1-(6-bromo-1-oxohexyl)-3,4-dimethoxybenzene. The nmr spectrum was consistent with the structure.

EXAMPLE 8

4-(3,4-Dimethoxyphenyl)-3-butyn-1-ol

A mixture of 10 g (46 mmol) of 1-bromo-3,4-dimethoxybenzene, 3.4 g (48 mmol) of 3-butyn-1-ol and 8 mL (58 mmol) of triethylamine in 20 mL of methylene chloride was stirred and flushed with argon. To the mixture there was added 0.12 g (0.06 mmol) of cuprous iodide and 0.30 g (0.43 mmol) of bis(triphenylphosphine)palladium dichloride. The reaction mixture was stirred at room temperature for 4 hours and at reflux for 16 hours. After filtration, the filtrate was washed with water, dried and concentrated. The crude product was purified by HPLC using 30% ethyl acetate-toluene to give 3.0 g (32% yield) of 4-(3,4-dimethoxyphenyl)-3-butyn-1-ol.

EXAMPLE 9

4-(3,4-Dimethoxyphenyl)butan-1-ol

A mixture of 2.0 g of 4-(3,4-dimethoxyphenyl)-3-butyn-1-ol and 0.2 g of 10% palladium on carbon in 40 mL of ethanol was stirred in a hydrogen atmosphere for 4 hours. After filtration, the filtrate was concentrated under reduced pressure to give 1.9 g of 4-(3,4-dimethoxyphenyl)butan-1-ol as an oil.

EXAMPLE 10

4-(2,3-Dimethoxyphenyl)butan-1-ol

To 0.8 g (0.12 g-atoms) of lithium ribbon cut in small pieces in 50 mL of anhydrous ether stirred at room temperature under an argon atmosphere was added 12 g (0.06 mol) of 3-bromo-propan-1-ol 1-ethoxy ethyl ether [P. E. Eaton, G. F. Cooper, R. C. Johnston, and R. H. Mueller, J. Org. Chem. 37, 1947 (1972)]. After about 1 mL was added, the reaction mixture was cooled in an ice-salt bath and the rest of the bromo compound was added dropwise over 35 minutes. Stirring was continued with cooling for 1.5 hours and then 7.5 g (0.045 mol) of 2,3-dimethoxybenzaldehyde in 45 mL of anhydrous ether was added dropwise over 30 minutes. After 1 hour, the cooling bath was removed and stirring was continued at room temperature for 1 hour. The reaction mixture was poured into half-saturated ammonium sulfate solution. The ether layer was separated, dried ($Na_2SO_4$) and concentrated to an oil (13.9 g). Ethanol (25 mL), water (25 mL) and 2 mL of concentrated hydrochloric acid were added and the solution was left at room temperature for 35 minutes. Potassium carbonate was added with stirring until the mixture was basic. The ethanol was removed under reduced pressure and the product was extracted with ethyl acetate. The dried extract was concentrated to an oil (12.0 g). This was dissolved in 150 mL of ethanol, 1 g of 10% palladium on carbon was added and the mixture was shaken on a Parr hydrogenator under an initial hydrogen pressure of 55 psi for 5 hours. The reaction mixture was filtered through Celite and the filtrate was concentrated to an oil. Purification by HPLC using 30% ethylacetate-hexane gave 7.45 g (79% yield) of 4-(2,3-dimethoxyphenyl)butan-1-ol.

This procedure has been reported in the literature to prepare 7-(2,3-dimethoxyphenyl)heptan-1-ol. J. H. P. Tyman and C. H. Khor, Chem. Ind. (1974), 526.

EXAMPLE 11

2-Hydroxy-4-(2-propenyloxy)benzoic acid methyl ester

A mixture of 102 g (0.607 mol) of methyl 2,4-dihydroxybenzoate, 54 mL (0.619 mol) of allyl bromide and 126 g (0.91 mol) of anhydrous potassium carbonate in 300 mL of anhydrous acetone was stirred at reflux for 3 hours. The reaction mixture was filtered and the solid was washed with acetone. After removal of the acetone from the filtrate under reduced pressure, the residue was distilled to give 85 g (67% yield), bp 106°–108°/0.3 mm of 2-hydroxy-4-(2-propenyloxy)benzoic acid methyl ester.

EXAMPLE 12

2,4-Dihydroxy-3-(2-propenyl)benzoic acid methyl ester 81 g of 2-hydroxy-4-(2-propenyloxy)benzoic acid methyl ester was heated in an oil bath under argon until the internal temperature reached 180°–185°. The temperature was maintained in this range for 1.5 hours and then raised to 210° for 1.5 hours. After cooling, the oil crystallized and was recrystallized from ether-petroleum ether to give 37 g (46% yield), mp 65°–66° of 2,4-dihydroxy-3-(2-propenyl)benzoic acid methyl ester. Anal. Calcd for $C_{11}H_{12}O_4$: C, 63.46; H, 5.81; C, 63.65; H, 6.09.

EXAMPLE 13

2,4-Dihydroxy-3-propylbenzoic acid methyl ester

A solution of 54 g of 2,4-dihydroxy-3-(2-propenyl)-benzoic acid methyl ester in 900 mL of ethanol and 3 g of 10% palladium on carbon was shaken in a hydrogen atmosphere until the uptake ceased (45 minutes). The catalyst was removed by filtration through Celite and the filtrate was concentrated under reduced pressure to an oil which solidified. After stirring with hexane, the product was filtered to give 51 g, mp 66°–68°, of 2,4-dihydroxy-3-propylbenzoic acid methyl ester.

Anal. Calcd for $C_{11}H_{14}O_4$: C, 62.85; H, 6.71. Found: C, 62.95; H, 6.74.

EXAMPLE 14

2,4-Dihydroxy-3-propylbenzoic acid phenylmethyl ester

A solution of 37 g (0.18 mol) of 2,4-dihydroxy-3-propylbenzoic acid methyl ester in 750 mL of methanol and 415 mL of 3N sodium hydroxide was stirred at reflux for 3 hours. The methanol was removed under reduced pressure and the residue was treated with water and 6N hydrochloric acid to acidify. The solid product was extracted with ethyl acetate and the extract was dried and concentrated under reduced pressure to a tan solid which was used without purification. This crude acid (35 g, 0.18 mol), 23 mL (0.2 mol) of benzyl chloride and 17 g (0.2 mol) of sodium bicarbonate in 250 mL of anhydrous dimethylformamide was stirred and heated at 60° for 23 hours. The solvent was removed under reduced pressure and the residue was treated with saturated sodium bicarbonate solution and the product was extracted with ethyl acetate. The dried extract was concentrated under reduced pressure and the residual oil was purified by HPLC using 15% ethyl acetate hexane to give 36 g (70% yield), mp 86°–88° of 2,4-dihydroxy-3-propylbenzoic acid phenylmethyl ester.

EXAMPLE 15

5-Chloro-2,4-dihydroxy-3-propylbenzoic acid methyl ester

A solution of 2.1 g (0.01 mol) of 2,4-dihydroxy-3-propylbenzoic acid methyl ester and 1.6 g (0.012 mol) of N-chlorosuccinimide in 50 mL of carbon tetrachloride was stirred at reflux for 9.5 hours. Additional N-chlorosuccinimide (1.6 g) was added and reflux was continued for 17 hours. 0.8 g of N-chlorosuccinimide was added and reflux was continued for 8 hours. Water was added. The organic layer was separated and washed with sodium thiosulfate solution, sodium bicarbonate solution, dried and concentrated under reduced pressure to give 5-chloro-2,4-dihydroxy-3-propylbenzoic acid methyl ester. Recrystallization from hexane gave analytically pure material, mp 75°–76°.

Anal. Calcd for $C_{11}H_{13}ClO_4$: C, 54.00; H, 5.35; Cl, 14.49. Found: 54.26; H, 5.32; Cl, 14.20.

EXAMPLE 16

4-[6-(2,3-Dimethoxyphenyl)hexyloxy]-2-hydroxy-3-propylbenzoic acid methyl ester

A mixture of 29.2 g (0.097 mol) of 1-(6-bromohexyl)-2,3-dimethoxybenzene, 18.5 g (0.088 mol) of 2,4-dihydroxy-3-propylbenzoic acid methyl ester, 18.2 g (0.13 mol) of anhydrous potassium carbonate and 21.9 g (0.13 mol) of potassium iodide in 550 mL of anhydrous acetone was stirred at reflux for 22 hours. The reaction mixture was filtered and the filtrate was concentrated under reduced pressure to an oil which was purified by HPLC using 8% ethyl acetate-hexane to give 31.4 g (83% yield) of 4-[6-(2,3-dimethoxyphenyl)hexyloxy]-2-hydroxy-3-propylbenzoic acid methyl ester as an oil.

Anal. Calcd for $C_{25}H_{34}O_6$: C, 69.74; H, 7.96, Found: C, 69.72; H, 7.81.

Compounds of Examples 17–23 which follow were prepared in accordance with the procedure of Example 16.

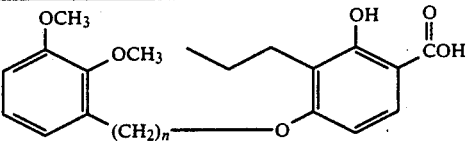

| Ex. No. | n | mp (°C.)* | Yield % | Formula | Microanalysis Calcd C | H | Found C | H |
|---|---|---|---|---|---|---|---|---|
| 25 | 2 | 154–156 | 88 | $C_{20}H_{24}O_6$ | 66.65 | 6.71 | 66.83 | 6.58 |
| 26 | 3 | 133–134 | 92 | $C_{21}H_{26}O_6$ | 67.36 | 7.00 | 67.26 | 6.98 |
| 27 | 4 | 111–113 | 78 | $C_{22}H_{28}O_6$ | 68.02 | 7.27 | 67.87 | 7.35 |
| 28 | 7 | 98–100 | 91 | $C_{25}H_{34}O_6$ | 69.74 | 7.96 | 69.79 | 8.05 |
| 29 | 8 | 90–92 | 81 | $C_{26}H_{36}O_6$ | 70.24 | 8.16 | 70.03 | 7.92 |
| 30 | 10 | 77–78 | 90 | $C_{28}H_{40}O_6$ | 71.16 | 8.53 | 71.14 | 8.52 |

*All compounds were recrystallized from ether hexane

EXAMPLE 31

2-Hydroxy-4-[6-[2,3-dimethoxy-4-(1-methylethyl)phenyl]hexyloxy]-3-propylbenzoic acid A solution of 6.96 g of 2-hydroxy-4-[6-[2,3-dimethoxy-4-(1-methylethyl)phenyl]hexyloxy]-3-propylbenzoic acid phenylmethyl ester in 150 mL of ethyl acetate and 1.4 g of 10% palladium on carbon was stirred in a hydrogen atmosphere for 3 hours. The reaction mixture

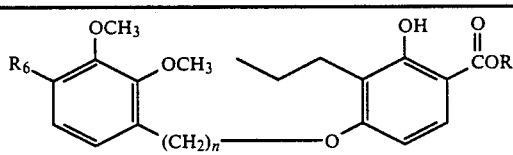

| Ex. No. | $R_6$ | R | n | % EtoAc-Hexane used in HPLC, mp (°C.) | Yield % | Formula | Microanalysis Calcd C | H | Found C | H |
|---|---|---|---|---|---|---|---|---|---|---|
| 17 | H | $CH_3$ | 2 | 5, 77–80 | 19 | $C_{21}H_{26}O_6$ | 67.36 | 7.00 | 67.24 | 7.15 |
| 18 | H | $CH_3$ | 3 | 10, 51–53 | 74 | $C_{22}H_{28}O_6$ | 68.02 | 7.27 | 68.26 | 7.54 |
| 19 | H | $CH_3$ | 4 | 10, oil | 88 | $C_{23}H_{30}O_6$ | 68.64 | 7.51 | 68.50 | 7.55 |
| 20 | H | Benzyl | 7 | 8, oil | 93 | $C_{32}H_{40}O_6$ | 73.82 | 7.74 | 74.04 | 7.66 |
| 21 | H | $CH_3$ | 8 | 10, oil | 96 | $C_{27}H_{38}O_6$ | 70.72 | 8.35 | 70.62 | 8.42 |
| 22 | H | Benzyl | 10 | 10, oil | 89 | $C_{35}H_{46}O_6$ | 74.70 | 8.24 | 74.46 | 8.50 |
| 23 | $CH(CH_3)_2$ | Benzyl | 6 | 5, oil | 95 | $C_{34}H_{44}O_6$ | not submitted | | | |

EXAMPLE 24

4-[6-(2,3-Dimethoxyphenyl)hexyloxy]-2-hydroxy-3-propylbenzoic acid

A solution of 31.4 g (0.073 mol) of 4-[6-(2,3-dimethoxyphenyl)hexyloxy]-2-hydroxy-3-propylbenzoic acid methyl ester in 800 ml of methanol and 365 mL (0.0365 mol) of 1N sodium hydroxide was stirred at reflux for 1.5 hours. The methanol was removed under reduced pressure, the residue was acidified and the product was extracted with methylene chloride. The dried extract was concentrated under reduced pressure to a solid which was recrystallized from ether-hexane to give 24.8 g (82% yield), mp 115°–118°, of 4-[6-(2,3-dimethoxyphenyl)hexyloxy]-2-hydroxy-3-propylbenzoic acid.

Anal. Calcd for $C_{24}H_{32}O_6$: C, 69.21; H, 7.74 Found: C, 69.50; H, 7.69

Compounds of Examples 25–30 were prepared by the procedure of Example 24.

was filtered through a Celite pad and the filtrate was concentrated under reduced pressure to 5.45 g, mp 106°–108°, of 2-hydroxy-4-[6-[2,3-dimethoxy-4-(1-methylethyl)phenyl]hexyloxy]-3-propylbenzoic acid.

Anal. Calcd for $C_{27}H_{38}O_6$; C, 70.72; H, 8.35. Found: C, 70.74; H, 8.27.

EXAMPLE 32

4-[6-(2,3-Dihydroxyphenyl)hexyloxy]-2-hydroxy-3-propylbenzoic acid

To 5.0 g (0.012 mol) of 4-[6-(2,3-dimethoxyphenyl)hexyloxy]-2-hydroxy-3-propylbenzoic acid suspended in 250 mL of anhydrous methylene chloride and cooled at −70° was added 36 mL (0.036 mol) of 1M boron tribromide in methylene chloride dropwise over 30 minutes. The reaction mixture was stirred at −70° for 30 minutes and then kept at −18° for 17 hours. Water (150 mL) was added dropwise with stirring and the product was extracted with ether. The extract was concentrated under reduced pressure. The residue was taken up in 500 mL of ether and shaken vigorously with 125 mL of 1N HCl. The extract was dried and concentrated under reduced pressure to a solid. Recrystallization from ether-hexane gave 3.7 g (80% yield), mp 147°-150°, of 4-[6-(2,3-dihydroxyphenyl)hexyloxy]-2-hydroxy-3-propylbenzoic acid.

Anal. Calcd for $C_{22}H_{28}O_6$: C, 68.02; H, 7.27. Found: C, 67.82; H, 7.33.

The compounds of Examples 33–39 were prepared by the procedure of Example 32.

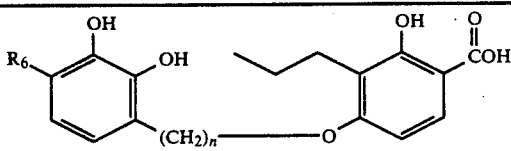

| Ex. No. | $R_6$ | n | mp (°C.)* | Yield % | Formula | Microanalysis Calcd C | H | Found C | H |
|---|---|---|---|---|---|---|---|---|---|
| 33 | H | 2 | 184–189 | 67 | $C_{18}H_{20}O_6$ | 65.05 | 6.07 | 64.70 | 6.03 |
| 34 | H | 3 | 189–191 | 86 | $C_{19}H_{22}O_6$ | 65.88 | 6.40 | 65.75 | 6.46 |
| 35 | H | 4 | 160–162 | 87 | $C_{20}H_{24}O_6$ | 66.65 | 6.71 | 66.49 | 6.67 |
| 36 | H | 7 | 144–146 | 81 | $C_{23}H_{30}O_6$ | 68.64 | 7.51 | 68.53 | 7.65 |
| 37 | H | 8 | 136–139 | 81 | $C_{24}H_{32}O_6$ | 69.21 | 7.74 | 69.11 | 7.93 |
| 38 | H | 10 | 126–128 | 75 | $C_{26}H_{36}O_6$ | 70.24 | 8.16 | 70.05 | 8.17 |
| 39 | $CH(CH_3)_2$ | 6 | 104–105 | 68 | $C_{25}H_{34}O_6$ | 69.74 | 7.96 | 69.85 | 8.21 |

*All compounds were recrystallized from ether hexane

EXAMPLE 40

4-[5-(2,3-Dihydroxyphenyl)pentyloxy]-2-hydroxy-3-propylbenzoic acid

A mixture of 6.88 g (0.0138 mol) of 1-(5-iodopentyl)-2,3-diphenylmethoxybenzene, 3.60 g (0.0125 mol) of 2,4-dihydroxy-3-propylbenzoic acid phenylmethyl ester, 2.60 g (0.0188 mol) of anhydrous potassium carbonate and 3.10 g (0.0188 mol) of potassium iodide in 150 mL of anhydrous acetone was stirred at reflux for 42 hours. The reaction mixture was filtered and the filtrate was concentrated under reduced pressure. The residue was purified by HPLC using 10% ethyl acetate-hexane to give 7.37 g (91% yield) of the phenylmethyl ester of 2-hydroxy-4-[5-[2,3-bis(phenylmethoxy)pentyloxy]-3-propylbenzoic acid as an oil which solidified, mp 65°-69°.

Anal. Calcd for $C_{42}H_{44}O_6$: C, 78.23; H, 6.88. Found: C, 78.04; H, 6.80.

A solution of 7.2 g of 2-hydroxy-4-[5-[2,3-bis (phenylmethoxy)pentyloxy]-3-propylbenzoic acid phenylmethyl ester in 500 mL of tetrahydrofuran and 1.4 g of 10% palladium on carbon was stirred in a hydrogen atmosphere for 25 hours. The reaction mixture was filtered through a Celite pad and the filtrate was concentrated under reduced pressure to a solid which was recrystallized from ether-hexane to give 3.8 g (90% yield), mp 155°-157°, of 4-[5-(2,3-dihydroxyphenyl)pentyloxy]-2-hydroxy-3-propylbenzoic acid.

Anal. Calcd for $C_{21}H_{26}O_6$: C, 67.36; H, 7.00. Found: C, 67.14; H, 7.16

EXAMPLE 41

4-[6(2,3-Dimethoxyphenyl)hexyloxy]-3-propylbenzoic acid ethyl ester

A mixture of 1.40 g (4.8 mmol) of 1-(6-bromohexyl)-2,3-dimethoxybenzene, 1.00 g (4.8 mmol) of 4-hydroxy-3-propylbenzoic acid ethyl ester, 1.30 g (9.6 mmol) of potassium carbonate and 0.72 g (4.8 mmol) of sodium iodide in 35 mL of acetone was stirred at reflux for 47 hours. Workup and purification as described in Example 16 gave 2.0 g of 4-[6-(2,3-dimethoxyphenyl)hexyloxy]-3-propylbenzoic acid ethyl ester as an oil. The mass spectrum showed the molecular ion at m/e 428.

EXAMPLE 42

4-[6-(2,3-Dimethoxyphenyl)hexyloxy]-3-propylbenzoic acid

A solution of 2.0 g of 4-[6-(2,3-dimethoxyphenyl)hexyloxy]-3-propylbenzoic acid ethyl ester in 70 mL of methanol and 24 mL of 1N sodium hydroxide was stirred at reflux for 3 hours. Workup as in Example 24 gave 1.87 g, mp 107°-108°, of 4-[6-(2,3-dimethoxyphenyl)hexyloxy]-3-propylbenzoic acid.

Anal. Calcd for $C_{24}H_{32}O_5$: C, 71.97; H, 8.05. Found C, 71.75; H, 8.05

EXAMPLE 43

4-[6-(2,3-Dihydroxyphenyl)hexyloxy]-3-propylbenzoic acid

To 1.80 g of 4-[6-(2,3-dimethoxyphenyl)hexyloxy]-3-propylbenzoic acid in 125 mL of methylene chloride cooled at −70° was added 14 mL of 1M boron tribromide in methylene chloride. After 30 minutes at −70° and 5 hours at −20°, the reaction was worked up as in Example 32 and the product was recrystallized from ether-hexane to give 1.12 g, mp 123°-124° of 4-[6-(2,3-dihydroxyphenyl)hexyloxy]-3-propylbenzoic acid.

Anal. Calcd for $C_{22}H_{28}O_5$: C, 70.94; H, 7.58. Found: C, 70.99; H, 7.83

EXAMPLE 44

4-[6-(2,3-Dimethoxyphenyl)hexyloxy]-3,5-dipropylbenzoic acid ethyl ester

A mixture of 1.20 g (4.0 mmol) of 1-(6-bromohexyl)-2,3-dimethoxybenzene, 1.00 g (4.0 mmol) of 3,5-dipropyl-4-hydroxybenzoic acid ethyl ester, 1.10 g (8 mmol) of potassium carbonate and 0.6 g (4 mmol) of sodium iodide in 35 mL of acetone was stirred at reflux for 47 hours. Workup and purification as in Example 16 gave 4-[6-(2,3-dimethoxyphenyl)hexyloxy]-3,5-dipropylbenzoic acid ethyl ester as an oil.

EXAMPLE 45

4-[6-(2,3-Dimethoxyphenyl)hexyloxy]-3,5-dipropylbenzoic acid

A solution of 1.8 g of 4-[6-(2,3-dimethoxyphenyl)hexyloxy]-3,5-dipropylbenzoic acid ethyl ester in 100 mL of methanol and 20 mL of 1N sodium hydroxide was stirred at reflux for 3 hours. Workup as in Example 24 gave 4-[6-(2,3-dimethoxyphenyl)hexyloxy]-3,5-dipropylbenzoic acid, mp 61°–65°.

Anal. Calcd for $C_{27}H_{38}O_5$: C, 73.27; H, 8.65. Found: C, 73.30; H, 8.72.

EXAMPLE 46

4-[6-(2,3-Dihydroxyphenyl)hexyloxy]-3,5-dipropylbenzoic acid

To 1.7 g of 4-[6-(2,3-dimethoxyphenyl)hexyloxy]-3,5-dipropylbenzoic acid in 125 mL of methylene chloride cooled at −70° was added 14 mL of 1M boron tribromide in methylene chloride. After 30 minutes at −70° and 5 hours at −20°, the reaction was worked up as in Example 32 and the product was recrystallized from ether-hexane to give 0.27 g, mp 94°–96°; of 4-[6-(2,3-dihydroxyphenyl)hexyloxy]-3,5-dipropylbenzoic acid.

Anal. Calcd. for $C_{25}H_{34}O_5$: C, 72.44; H, 8.27. Found: C, 72.70; H, 8.32

EXAMPLE 47

4-[6-(2,3-Dihydroxyphenyl)hexyloxy]-2-hydroxy-3-propylbenzoic acid ethyl ester

A mixture of 0.90 g (0.0023 mol) of 4-[6-(2,3-dihydroxyphenyl)hexyloxy]-2-hydroxy-3-propylbenzoic acid, 1.9 mL (0.023 mol) of ethyl iodide and 0.21 g of sodium bicarbonate in 10 mL of anhydrous dimethylformamide was stirred and heated at 50° for 6 hours. The solvent was removed on the oil pump, the residue was treated with sodium bicarbonate solution and the product was extracted with ethyl acetate. The dried extract was concentrated and the residue was chromatographed on 35 g of silica gel. Elution with 10% ethyl acetate-toluene gave 0.89 g of an oil which was stirred with hexane and filtered to give 0.71 g (70% yield), mp 54°–57°; of 4-[6-(2,3-dihydroxyphenyl)hexyloxy]-2-hydroxy-3-propylbenzoic acid ethyl ester.

Anal. Calcd for $C_{24}H_{32}O_6$: C 69.21; H, 7.74. Found: C, 68.85; H, 7.82.

EXAMPLE 48

4-[6-(2,3-Dihydroxyphenyl)hexyloxy]-2-hydroxy-3-propylbenzoic acid [2-(diethylamino)ethyl]ester hydrochloride.

A mixture of 1.0 g (2.57 mmol) of 4-[6-(2,3-dihydroxyphenyl)hexyloxy]-2-hydroxy-3-propylbenzoic acid, 3.5 g (25.7 mmol) of 2-diethylaminoethyl chloride and 0.24 g (2.83 mmol) of sodium bicarbonate in 20 mL of anhydrous dimethylformamide was stirred and heated at 50° for 1.5 hours. The solvent was removed on the oil pump. The residue was treated with sodium bicarbonate solution and the product was extracted with ethyl acetate. The dried extract was concentrated and the residue was chromatographed on 50 g of silica gel. Elution with $CH_2Cl_2$:95% MeOH:$NH_4OH$ (95:5:0.05) gave 1.0 g of the free base of 4-[6-(2,3-dihydroxyphenyl)hexyloxy]-2-hydroxy-3-propylbenzoic acid [2-(diethylamino)ethyl]-ester. This was dissolved in methylene chloride, treated with 3.2 mL of 2M HCl in ethanol. After concentration and addition of hexane, 0.91 g (68% yield), mp 98°–100°, of 4-[6-(2,3-dihydroxyphenyl)hexyloxy]-2-hydroxy-3-propylbenzoic acid [2-(diethylamino)ethyl]-ester hydrochloride was obtained.

Anal. Calcd for $C_{28}H_{41}NO_6HCl$: C, 64.17; H, 8.08; N, 2.67; $Cl^-$, 6.76. Found: C, 64.35; H, 8.38; N, 2.51; $Cl^-$, 6.55

EXAMPLE 49

2-Hydroxy-4-[6-[2,3-bis[(4-methylbenzoyl)oxy]phenyl]-hexyloxy]-3-propylbenzoic acid phenylmethyl ester A mixture of 1.91 g (3.75 mmol) of 1-(6-bromohexyl)-2,3-bis[(4-methylbenzoyl)oxy]benzene, 1.07 g (3.75 mmol) 2,4-dihydroxy-3-propylbenzoic acid phenylmethyl ester, 0.94 g (5.63 mmol) of potassium iodide and 0.75 g (5.63 mol) of potassium carbonate in 40 mL of acetone was stirred at reflux for 26 hours. The reaction mixture was filtered and the filtrate was concentrated under reduced pressure. The crude product was purified by HPLC using 5% ethyl acetate-hexane to give 0.85 g (32% yield) of 2-hydroxy-4-[6-[2,3-bis[(4-methylbenzoyl)oxy]phenyl]hexyloxy]-3-propylbenzoic acid phenylmethyl ester as an oil.

Anal. Calcd for $C_{45}H_{46}O_8$: C, 75.61; H, 6.49. Found: C, 75.63; H, 6.57

EXAMPLE 50

2-Hydroxy-4-[6-[2,3-bis[4-methylbenzoyl)oxy]phenyl]-hexyloxy]-3-propylbenzoic acid A solution of 0.78 g of 2-hydroxy-4-[6-[2,3-bis[(4-methylbenzoyl)oxy]phenyl]hexyloxy]-3-propylbenzoic acid phenylmethyl ester in 65 mL of tetrahydrofuran and 0.16 g of 10% palladium on carbon was shaken in a hydrogen atmosphere for 3 hours. The reaction mixture was filtered through Celite and the filtrate was concentrated under reduced pressure to a solid which was recrystallized from methylene chloride-hexane to give 0.57 g, mp 141°–143°, of 2-hydroxy-4-[6-[2,3-bis[4-methylbenzoyl)oxy]phenyl]hexyloxy]-3-propylbenzoic acid.

Anal. Calcd for $C_{38}H_{40}O_8$: C, 73.06; H, 6.45. Found: C, 72.91, H, 6.56.

EXAMPLE 51

4-[6-[2,3-Bis(acetyloxy)phenyl]hexyloxy]-2-hydroxy-3-propylbenzoic acid phenylmethyl ester To a suspension of 0.14 g (3.5 mmol, 60% on oil) of sodium hydride in 10 mL of anhydrous dimethylformamide stirred at room temperature was added 0.88 g (3.1 mmol) of 2,4-dihydroxy-3-propylbenzoic acid phenylmethyl ester. The reaction mixture was stirred for 2 hours and then 1.09 g (3.1 mmol) of 1-(6-bromohexyl)-2,3-bis(acetyloxy)benzene in 10 mL of dimethylformamide was added dropwise. Stirring at 50° was continued for 16 hours and then the solvent was removed on the oil pump. The crude product was purified by HPLC using 25% ethyl acetate-hexane to give 0.55 g (28% yield) of 4-[6-[2,3-bis(acetyloxy)phenyl]hexyloxy]-2-hydroxy-3-propylbenzoic acid phenylmethyl ester as an oil.

Anal. Calcd for $C_{33}H_{38}O_8$: C, 70.44; H, 6.81. Found: C, 70.07; H, 6.83.

EXAMPLE 52

4-[6-[2,3-Bis(acetyloxy)phenyl]hexyloxy]-2-hydroxy-3-propylbenzoic acid

A solution of 0.53 g of 4-[6-[2,3-bis(acetyloxy)-phenyl]hexyloxy]-2-hydroxy-3-propylbenzoic acid phenylmethyl ester in 50 mL of tetrahydrofuran and 0.10 g of 10% palladium on carbon was shaken in a hydrogen atmosphere for 3 hours. The reaction mixture was filtered through Celite and the filtrate was concentrated to a solid which was recrystallized from ether-hexane to give 0.35 g, mp 120°–122°, of 4-[6-[2,3-bis(acetyloxy)phenyl]hexyloxy]-2-hydroxy-3-propylbenzoic acid.

Anal. Calcd for $C_{26}H_{32}O_8$: C, 66.09; H, 6.83. Found: C, 66.08; H, 6.87

EXAMPLE 53

2-Hydroxy-4-[6-[2,3-bis(phenylmethoxy)phenyl]hexyloxy]-3-propylbenzoic acid phenylmethyl ester A mixture of 1.31 g (2.6 mmol) of 1-(6-iodohexyl)-2,3-bis(phenylmethoxy)benzene, 0.74 g (2.6 mmol) of 2,4-dihydroxy-3-propylbenzoic acid phenylmethyl ester and 0.54 g (3.9 mmol) of potassium carbonate in 35 mL of acetone was stirred at reflux for 39 hours. The reaction mixture was filtered and the filtrate was concentrated under reduced pressure to an oil which was purified by HPLC using 8% ethyl acetate-hexane to give 1.03 g (60% yield) of 2-hydroxy-4-[6-[2,3-bis(phenylmethoxy)phenyl]hexyloxy]-3-propylbenzoic acid phenylmethyl ester as an oil.

Anal. Calcd for $C_{43}H_{46}O_6$: C, 78.39; H, 7.04. Found: C, 78.24; H, 7.06

EXAMPLE 54

2-Acetyloxy-4-[6-[2,3-bis(phenylmethoxy)phenyl]hexyloxy]-3-propylbenzoic acid phenylmethyl ester A solution of 1.15 g of 2-hydroxy-4-[6-[2,3-bis(phenylmethoxy)phenyl]hexyloxy]-3-propylbenzoic acid phenylmethyl ester in 15 mL of pyridine and 15 mL of acetic anhydride was stirred and heated at 50° for 15 hours. The reaction mixture was concentrated on the oil pump. The residue was dissolved in ethyl acetate and the solution was washed with sodium bicarbonate solution, dried and concentrated under reduced pressure to give 1.03 g of 2-acetyloxy-4-[6-[2,3-bis(phenylmethoxy)phenyl]hexyloxy]-3-propylbenzoic acid phenylmethyl ester as an oil.

Anal. Calcd for $C_{45}H_{48}O_7$: C, 77.12; H, 6.90. Found: C, 77.17; H, 7.18.

EXAMPLE 55

2-Acetyloxy-4-[6-(2,3-dihydroxyphenyl)hexyloxy]-3-propylbenzoic acid

A solution of 1.02 g of 2-acetyloxy-4-[6-[2,3-bis(phenylmethoxyphenyl]hexyloxy]-3-propylbenzoic acid phenylmethyl ester in 65 mL of tetrahydrofuran and 0.20 g of 10% palladium on carbon was stirred in hydrogen atmosphere for 24 hours. The reaction mixture was filtered through Celite and the filtrate was concentrated and the residue was crystallized from ether-hexane to give 0.51 g (82% yield), mp 130°–132°, of 2-acetyloxy-4-[6-(2,3-dihydroxyphenyl)hexyloxy]-3-propylbenzoic acid.

Anal. Calcd for $C_{24}H_{30}O_7$: C, 66.96; H, 7.02. Found: C, 67.27; H, 7.16

EXAMPLE 56

5-Chloro-2-hydroxy-4-[6-[2,3-bis(phenylmethoxy)phenyl]hexyloxy]-3-propylbenzoic acid methyl ester A mixture of 0.41 g (0.8 mmol) of 1-(6-iodohexyl)-2,3-bis(phenylmethoxy)benzene, 0.18 g (0.74 mmol) of 5-chloro-2,4-dihydroxypropylbenzoic acid methyl ester and 0.22 g (1.6 mmol) of potassium carbonate in 15 mL of acetone was stirred at reflux for 16 hours. The reaction mixture was filtered and the filtrate was concentrated to an oil. Chromatography on 30 g of silica gel and elution with 10% ethyl acetate-hexane gave 0.31 g (68% yield) of 5-chloro-2-hydroxy-4-[6-[2,3-bis(phenylmethoxy)phenyl]hexyloxy]-3-propylbenzoic acid methyl ester as an oil.

EXAMPLE 57

5-Chloro-2-hydroxy-4-[6-[2,3-bis(phenylmethoxy)phenyl]hexyloxy]-3-propylbenzoic acid A solution of 0.30 g of 5-chloro-2-hydroxy-4-[6-[2,3-bis(phenylmethoxy)phenyl]hexyloxy]-3-propylbenzoic acid methyl ester in 10 mL of methanol, 5 mL of dioxane and 2.5 mL of 1N sodium hydroxide was left at room temperature for 3 days. The solvent was removed under reduced pressure and the residue was acidified and extracted with ethyl acetate. The dried extract was concentrated and chromatographed on 30 g of silica gel using acetic acid:ethyl acetate:toluene (1:25:75) to give 0.21 g of 5-chloro-2-hydroxy-4-[6-[2,3-bis(phenylmethoxy)phenyl]hexyloxy]-3-propylbenzoic acid as an oil.

EXAMPLE 58

5-Chloro-2-hydroxy-4-[6-(2,3-dihydroxyphenyl)hexyloxy]-3-propylbenzoic acid

A solution of 0.21 g of 5-chloro-2-hydroxy-4-[6-[2,3-bis(phenylmethoxy)phenyl]hexyloxy]-3-propylbenzoic acid in 30 mL of ethyl acetate and 0.073 g of 10% palladium on carbon was shaken under hydrogen pressure (30–40 p.s.i.) for 21 hours. The reaction mixture was filtered through Celite and the filtrate was concentrated to an oil. Chromatography on 20 g of silica gel and elution with acetic acid:ethyl acetate:toluene (5:20:75) gave 82 mg, mp 110°–113°, of 5-chloro-2-hydroxy-4-[6-(2,3-dihydroxyphenyl)hexyloxy]-3-propylbenzoic acid.

Anal. Calcd for $C_{22}H_{27}ClO_6$: C, 62.48; H, 6.44; Cl, 8.38. Found: C, 62.58; H, 6.75; Cl, 8.16.

EXAMPLE 59

4-[6-(2,3-Dimethoxyphenyl)hexyloxy]-2-hydroxybenzoic acid methyl ester

A mixture of 1.0 g (3.3 mmol) of 1-(6-bromohexyl)-2,3-dimethoxybenzene, 0.55 g (3.3 mmol) of 2,4-dihydroxybenzoic acid methyl ester, 1.2 g (9 mmol) of potassium carbonate and 0.75 g (4.5 mmol) of potassium iodide in 25 mL of acetone was stirred at reflux for 20 hours. Workup as in Example 16 gave 1.2 g of 4-[6-(2,3-dimethoxyphenyl)hexyloxy]-2-hydroxybenzoic acid methyl ester as an oil.

EXAMPLE 60

4-[6-(2,3-Dimethoxyphenyl)hexyloxy]-2-hydroxybenzoic acid

A solution of 0.45 g (1.2 mmol) of 4-[6-(2,3-dimethoxyphenyl)hexyloxy]-2-hydroxybenzoic acid methyl ester in 25 mL of methanol and 8 mL of 1N sodium hydroxide was refluxed for 7 hours. Workup as in Example 24 and recrystallization from methanol gave 0.36 g (82% yield), mp 115°–116° of 4-[6-(2,3-dimethoxyphenyl)hexyloxy]-2-hydroxybenzoic acid.

Anal. Calcd for $C_{21}H_{26}O_6$: C, 67.36; H, 7.00. Found: C, 67.12; H, 7.14.

EXAMPLE 61

4-[6-(2,3-Dihydroxyphenyl)hexyloxy]-2-hydroxybenzoic acid

To 0.35 g of 4-[6-(2,3-dimethoxyphenyl)hexyloxy]-2-hydroxybenzoic acid in 10 mL of methylene chloride stirred and cooled at −70° was added 3.5 mL of 1M boron tribromide in methylene chloride. The reaction mixture was stirred at −70° for 20 minutes and at −20° for 6.5 hours. Workup as in Example 32 and crystallization from methanol gave 0.20 g (60% yield), mp 179°–180°, of 4-[6-(2,3-dihydroxyphenyl)hexyloxy]-2-hydroxy-benzoic acid.

Anal. Calcd for $C_{19}H_{22}O_6$: C, 65.58; H, 6.40. Found: C, 65.94; H, 6.57

EXAMPLE 62

2-Hydroxy-5-[6-[2,3-bis(phenylmethoxy)phenyl]hexyloxy]benzoic acid methyl ester A mixture of 1.00 g of 1-(6-iodohexyl)-2,3-bis(phenylmethoxy)benzene, 0.34 g of 2,5-dihydroxybenzoic acid methyl ester and 1.0 g of potassium carbonate in 30 mL of acetone was stirred at reflux for 17 hours. Workup as in Example 16 and chromatography on 60 g of silica gel using 1% ethyl acetate-toluene gave 0.42 g (39% yield) of 2-hydroxy-5-[6-[2,3-bis(phenylmethoxy)phenyl]hexyloxy]benzoic acid methyl ester as an oil.

EXAMPLE 63

2-Hydroxy-5-[6-[2,3-bis(phenylmethoxy)phenyl]hexyloxy]benzoic acid

A solution of 0.42 g of 2-hydroxy-5-[6-[2,3-bis(phenylmethoxy)phenyl]hexyloxy]benzoic acid methyl ester in 12 mL of ethanol and 4 mL of 1N sodium hydroxide was stirred at reflux for 1.5 hours. Workup as in Example 24 and recrystallization from ether-hexane gave 0.25 g, mp 97°–100°, of 2-hydroxy-5-[6-[2,3-bis(phenylmethoxy)phenyl]hexyloxy]benzoic acid.

Anal. Calcd for $C_{33}H_{34}O_6$: C, 75.26; H, 6.51. Found: C, 75.28; H, 6.58

EXAMPLE 64

2-Hydroxy-5-[6-(2,3-dihydroxyphenyl)hexyloxy]benzoic acid

A mixture of 0.22 g of 2-hydroxy-5-[6-[2,3-bis(phenylmethoxy)phenyl]hexyloxy]benzoic acid and 30 mg of 10% palladium on carbon in 10 ml of methanol was stirred in a hydrogen atmosphere for 5 hours. Workup as in example 36 and recrystallization from acetone-hexane gave 0.10 g, mp 159°–161° of 2-hydroxy-5-[6-(2,3-dihydroxyphenyl)hexyloxy]benzoic acid.

Anal. Calcd. for $C_{19}H_{22}O_6$: C, 65.88; H, 6.40. Found: C, 65.91; H, 6.56

EXAMPLE 65

4-[6-(2,3-Dimethoxyphenyl)hexyloxy]benzoic acid methyl ester

A mixture of 1.00 g (3.3 mmol) of 1-(6-bromohexyl)-2,3-dimethoxybenzene, 0.45 g (3.0 mmol) of 4-hydroxybenzoic acid methyl ester, 0.62 g (4.5 mmol) of potassium carbonate and 0.75 g (4.5 mmol) of potassium iodide in 25 mL of acetone was stirred at reflux for 23 hours. Workup as in Example 16 and purification by HPLC using 15% ethyl acetate-hexane gave 1.10 g (89% yield) of 4-[6-(2,3-dimethoxyphenyl)hexyloxy]benzoic acid methyl ester as an oil.

Anal. Calcd for $C_{22}H_{28}O_5$: C, 70.94; H, 7.58. Found: C, 70.86; H, 7.59

EXAMPLE 66

4-[6-(2,3-Dihydroxyphenyl)hexyloxy]benzoic acid

To 0.80 g (2.2 mmol) of 4-[6-(2,3-dimethoxyphenyl)hexyloxy]benzoic acid methyl ester in 25 mL of methylene chloride stirred and cooled at −70° was added 8.0 mL of 1M boron tribromide in methylene chloride. The reaction mixture was stirred at −70° for 30 minutes and at −20° for 7 hours. Workup as in example 32 and recrystallization from ethyl acetate-hexane gave 0.30 g (42% yield), mp 170°–172° of 4-[6-(2,3-dihydroxyphenyl)hexyloxy]benzoic acid.

Anal. Calcd for $C_{19}H_{22}O_5$: C, 69.07; H, 6.71 Found: C, 68.81; H, 6.70

EXAMPLE 67

3-[6-[2,3-Bis(phenylmethoxy)phenyl]hexyloxy]benzoic acid methyl ester

A mixture of 0.58 g of 1-(6-iodohexyl)-2,3-bis(phenylmethoxy)benzene, 0.18 g of 3-hydroxybenzoic acid methyl ester and 0.25 g of potassium carbonate in 15 mL of acetone was stirred at reflux for 18 hours. Workup as in Example 16 and purification by HPLC using toluene gave 0.40 g (66% yield) of 3-[6-[2,3-bis(phenylmethoxy)phenyl]hexyloxy]benzoic acid methyl ester as an oil.

Anal. Calcd for $C_{34}H_{36}O_5$: C, 77.85; H, 6.92. Found: C, 77.62; H. 6.89.

EXAMPLE 68

3-[6-[2,3-Bis(phenylmethoxy)phenyl]hexyloxy]benzoic acid

A solution of 0.5 g of 3-[6-[2,3-bis(phenylmethoxy)phenyl]hexyloxy]benzoic acid methyl ester in 15 mL of methanol and 5 mL of 1N sodium hydroxide was stirred at reflux for 2 hours. Workup as in Example 24 and crystallization from methanol gave 0.34 g (70% yield), mp 72°–74°, of 3-[6-[2,3-bis(phenylmethoxy)phenyl]hexyloxy]benzoic acid.

Anal. Calcd for $C_{33}H_{34}O_5$: C, 77.62; H, 6.71. Found: C, 77.10; H, 6.66

EXAMPLE 69

3-[6-(2,3-Dihydroxyphenyl)hexyloxy]benzoic acid

A mixture of 0.33 g of 3-[6-[2,3-bis(phenylmethoxy)phenyl]hexyloxy]benzoic acid and 95 mg of 10% palladium on carbon in 20 mL of ethyl acetate and 5 mL of ethanol was stirred in a hydrogen atmosphere for 11 hours. The reaction mixture was filtered through Celite and the filtrate was concentrated under reduced pressure to an oil. Chromatography on 10 g of silica gel and elution with 10% methanol-chloroform gave a solid which was recrystallized from ether-hexane to give 0.14 g (63% yield), mp 123°–125°, of 3-[6-(2,3-dihydroxyphenyl)hexyloxy]benzoic acid.

Anal. Calcd for $C_{19}H_{22}O_5$: C, 69.07; H, 6.71. Found: C, 69.17; H, 6.93

EXAMPLE 70

3-Chloro-4-[6-[2,3-bis(phenylmethoxy)phenyl]hexyloxy]benzoic acid methyl ester A mixture of 5.6 g of 1-(6-iodohexyl)-2,3-bis(phenylmethoxy) benzene, 2.1 g of 3-chloro-4-hydroxybenzoic acid methyl ester and 5.0 g of potassium carbonate in 50 mL of acetone was stirred at reflux for 20 hours. Workup as in Example 16, chromatography on 100 g of silica gel using 15% ethyl acetate-hexane and crystallization from ethyl acetate-hexane gave 3.7 g (59% yield), mp 68°-69°, 3-chloro-4-[6-[2,3-bis(phenylmethoxy)phenyl]hexyloxy]benzoic acid methyl ester.

EXAMPLE 71

3-Chloro-4-[6-[2,3-bis(phenylmethoxy)phenyl]hexyloxy]benzoic acid

A solution of 3.6 g of 3-chloro-4-[6-[2,3-bis(phenylmethoxy)phenyl hexyloxy]benzoic acid methyl ester in 90 mL of methanol and 30 mL of 1N sodium hydroxide was refluxed for 2 hours. Workup as in Example 24, chromatography on 70 g of silica gel using 50% ethyl acetate-hexane and recrystallization from ether-hexane gave 1.3 g, mp 87°-89°, of 3-chloro-4-[-[2,3-bis(phenylmethoxy)phenyl]hexyloxy]benzoic acid.

EXAMPLE 72

3-Chloro-4-[6-(2,3-dihydroxyphenyl)hexyloxy]benzoic acid.

A mixture of 0.6 g of 3-chloro-4-[6-[2,3-bis(phenylmethoxy)phenyl]hexyloxy]benzoic acid and 60 mg of 10% palladium on carbon in 20 ml of tetrahydrofuran was stirred in a hydrogen atmosphere for 6 hours. Workup as in Example 36 and recrystallization from ethyl acetate-hexane gave 0.24 g, mp benzoic acid.

Anal. Calcd for $C_{19}H_{21}ClO_5$: C, 62.55; H, 5.80; Cl, 9.72. Found: C, 62.40; H, 5.95; Cl, 9.51

EXAMPLE 73

4-[2-(3,4-Dimethoxyphenyl)ethoxy]-2-hydroxy-3-propylbenzoic acid methyl ester

A mixture of 3.4 g (0.016 mol) of 2,4-dihydroxy-3-propylbenzoic acid methyl ester, 4.7 g (0.018 mol) of 1-[(2-methanesulfonyloxy)ethyl]-2,3-dimethoxybenzene, 4.4 g (0.032 mol) of potassium carbonate and 2.7 g (0.018 mol) of sodium iodide in 90 ml of acetone was stirred at reflux for 18 hours. 4.7 g of 1-[(2-methanesulfonyloxy)ethyl]-2,3-dimethoxybenzene and 4.4 g of potassium carbonate were added and reflux was continued for 41 hours. The reaction mixture was filtered and the filtrate was concentrated under reduced pressure to an oil which was purified by high pressure liquid chromatography using 10% ethyl acetate-hexane to remove impurities and then ethyl acetate to obtain 4.5 g of oil. This was stirred with hexane and filtered to give 1.65 g (28% yield), mp 56°-58°, of 4-[2-(3,4-dimethoxyphenyl)ethoxy]-2-hydroxy-3-propylbenzoic acid methyl ester.

Anal. Calcd for $C_{21}H_{26}O_6$: C, 67.36; H, 7.00. Found: C, 67.37; H, 7.06

EXAMPLE 74

4-[3-(3,4-Dimethoxyphenyl)propoxy]-2-hydroxy-3-propylbenzoic acid methyl ester

A mixture of 9.5 g (0.037 mol) of 1-(3-bromopropyl)-3,4-dimethoxybenzene [G. H. Douglas, C. R. Walk and H. Smith, J. Med. Chem., 9, 27 (1966)], 7.0 g (0.033 mol) of 2,4-dihydroxy-3-propylbenzoic acid methyl ester, 6.9 g (0.05 mol) of potassium carbonate and 8.3 g (0.05 mol) of potassium iodide in 250 mL of acetone was stirred at reflux for 24 hours. The reaction mixture was filtered and the filtrate was concentrated under reduced pressure to an oil which was purified by high pressure liquid chromatography using 15% ethyl acetate-hexane to give 7.2 g (56% yield) of 4-[3-(3,4-dimethoxyphenyl)propoxy]-2-hydroxy-3-propylbenzoic acid methyl ester as an oil.

Anal. Calcd for $C_{22}H_{28}O_6$: C, 68.02; H, 7.27. Found: C, 67.90; H, 7.37.

Compounds of Examples 78–80 were prepared using the procedure of Example 77.

| Ex. No. | R | n | Yield % | Formula | Microanalysis Calcd C | Calcd H | Found C | Found H |
|---|---|---|---|---|---|---|---|---|
| 75 | CH₃ | 4 | 49 | $C_{23}H_{30}O_6$ | 68.64 | 7.51 | 68.74 | 7.96 |
| 76 | Benzyl | 5 | 80 | $C_{30}H_{36}O_6$ | 73.15 | 7.37 | 72.99 | 7.51 |
| 77 | Benzyl | 6 | 97 | $C_{31}H_{38}O_6$ | not submitted | | | |

EXAMPLE 78

4-[3-(3,4-Dimethoxyphenyl)propoxy]-2-hydroxy-3-propylbenzoic acid .

A solution of 7.1 g of 4-[3-(3,4-dimethoxyphenyl)propoxy]-2-hydroxy-3-propylbenzoic acid methyl ester in 180 mL of methanol and 90 mL of 1N sodium hydroxide was stirred at reflux for 1 hour. The solvent was removed under reduced pressure, the residue was acidified and the product was extracted with methylene chloride. The dried (MgSO₄) extract was concentrated to 6.5 g, mp 104°-110°, of 4-[3-(3,4-dimethoxyphenyl)propoxy]-2-hydroxy-3-propylbenzoic acid.

Anal. Calcd for $C_{21}H_{26}O_6$: C, 67.36; H, 7.00. Found: C, 67.11; H, 7.00.

Compounds of Examples 82, 83 and 85 were prepared using the procedure of Example 81. Compound 84 was prepared using the procedure of Example 36, hydrogenolysis in tetrahydrofuran.

| Ex. No. | n | mp (°C.) | Yield % | Formula | Microanalysis Calcd C | Calcd H | Found C | Found H |
|---|---|---|---|---|---|---|---|---|
| 79 | 2 | 156–157 | 40 | $C_{20}H_{24}O_6$ | 66.28 | 7.23 | 66.37 | 6.82 |
| 80 | 4 | 125–127 | 87 | $C_{22}H_{28}O_6$ | 68.02 | 7.27 | 67.84 | 7.33 |
| 81 | 5 | 133–136 | 83 | $C_{23}H_{30}O_6$ | 68.64 | 7.51 | 68.45 | 7.42 |
| 82 | 6 | 99–101 | 65 | $C_{24}H_{32}O_6$ | 69.21 | 7.74 | 68.96 | 7.85 |

EXAMPLE 83

4-[3-(3,4-Dihydroxyphenyl)propoxy]-2-hydroxy-3-propylbenzoic acid

To 3.0 g (0.008 mol) of 4-[3-(3,4-dimethoxyphenyl)propoxy]-2-hydroxy-3-propylbenzoic acid suspended in 250 mL of methylene chloride and cooled at −70°, was added 24 mL (0.024 mol) of 1M boron tribromide in methylene chloride dropwise over 30 minutes. The reaction mixture was stirred at −70° for 1 hour and then in an ice bath for 1.5 hours. Water (100 mL) was added dropwise with stirring and the product was extracted with ether. The extract was concentrated under reduced pressure and the residue was taken up in ether (500 mL) and shaken vigorously with 100 mL of 1N hydrochloric acid. The dried extract was concentrated and the residue was recrystallized from ether-hexane to give 2.2 g (79% yield), mp 194°-195°, of 4-[3-(3,4-dihydroxyphenyl)propoxy]-2-hydroxy-3-propylbenzoic acid.

Anal. Calcd for $C_{19}H_{22}O_6$: C, 65.88; H, 6.40. Found: c, 65.51; H, 6.47

Compounds of examples 87-90 were prepared using the procedure of Example 86.

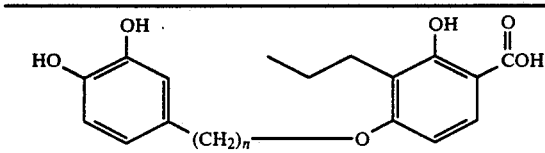

| Ex. No. | n | mp (°C.) | Yield % | Formula | Microanalysis Calcd C | H | Found C | H |
|---|---|---|---|---|---|---|---|---|
| 84 | 2 | 164-165 | 32 | $C_{18}H_{20}O_6$ | 65.05 | 6.07 | 64.66 | 6.01 |
| 85 | 4 | 190-193 | 95 | $C_{20}H_{24}O_6$ | 66.65 | 6.71 | 66.36 | 6.87 |
| 86 | 5 | 159-162 | 70 | $C_{21}H_{26}O_6$ | 67.36 | 7.00 | 66.96 | 7.08 |
| 87 | 6 | 113-114 | 58 | $C_{22}H_{28}O_6$ | 68.02 | 7.27 | 67.91 | 7.56 |

EXAMPLE 88

4-[3-(3,4-Dimethoxyphenyl)propoxy]benzoic acid ethyl ester

A mixture of 2.56 g (9.9 mmol) of 1-(3-bromopropyl)-3,4-dimethoxybenzene, 1.50 g (9 mmol) of 4-hydroxybenzoic acid ethyl ester, 1.38 g (10 mmol) of potassium carbonate and 1.66 g (10 mmol) of potassium iodide in 50 mL of acetone was stirred at reflux for 22 hours. Workup as in Example 16, purification by high pressure liquid chromatography using methylene chloride and recrystallization from 2-propanol gave 1.23 g (40% yield), mp 70°-71°, of 4-[3-(3,4-dimethoxyphenyl)propoxy]benzoic acid ethyl ester.

EXAMPLE 89

4-[3-(3,4-Dimethoxyphenyl)propoxy]benzoic acid

A solution of 1.2 g of 4-[3-(3,4-dimethoxyphenyl)propoxy]benzoic acid ethyl ester in 40 mL of methanol and 18 mL of 1N sodium hydroxide was stirred at reflux for 1 hour. Workup as in Example 24 gave 1.1 g, mp 150°-154°, of 4-[3-(3,4-dimethoxyphenyl)propoxy]benzoic acid.

Anal. Calcd for $C_{18}H_{20}O_5$: C, 68.34; H, 6.37. Found: C, 68.07; H, 6.16

EXAMPLE 90

4-[3-(3,4-Dihydroxyphenyl)propoxy]benzoic acid

To 1.08 g (3.4 mmol) of 4-[3-(3,4-dimethoxyphenyl)propoxy]benzoic acid suspended in 60 mL of methylene chloride and cooled at $-70°$ was added 10 ml (10 mmol) of 1M boron tribromide in methylene chloride. The reaction mixture was stirred at $-70°$ for 2.5 hours and then worked up as in Example 32. Recrystallization from ether-hexane gave 0.40 g (41% yield), mp 180°-185°, of 4-[3-(3,4-dihydroxyphenyl)propoxy]benzoic acid.

Anal. Calcd for $C_{16}H_{16}O_5$: C, 66.66; H, 5.59. Found: C, 66.37; H, 5.64

EXAMPLE 91

4-[[6-(3,4-Dimethoxyphenyl)-6-oxohexyl]oxy]-2-hydroxy-3-propylbenzoic acid methyl ester A mixture of 1.60 g (5 mmol) of 6-bromo-1-(3,4-dimethoxyphenyl)-1-hexanone, 0.95 g (4.5 mmol) of 2,4-dihydroxy-3-propylbenzoic acid methyl ester, 1.38 g (10 mmol) of potassium carbonate and 0.75 g (5 mmol) of sodium iodide in 40 mL of acetone was stirred at reflux for 45 hours. The reaction mixture was filtered and the filtrate was concentrated and treated with water. The product was filtered and recrystallized from methylene chloride-methanol to give 1.40 g (70% yield), mp 117°-119°, of 4-[[6-(3,4-dimethoxyphenyl)-6-oxohexyl]oxy]-2-hydroxy-3-propylbenzoic acid methyl ester.

Anal. Calcd for $C_{25}H_{32}O_7$: C, 67.55; H, 7.26. Found: C, 67.27; H, 7.29

EXAMPLE 92

4-[[6-(3,4-Dimethoxyphenyl)-6-oxohexyl]oxy]-2-hydroxy-3-propylbenzoic acid

A solution of 1.36 g of 4-[[6-(3,4-dimethoxyphenyl)-6-oxohexyl]oxy]-2-hydroxy-3-propylbenzoic acid methyl ester in 35 mL of methanol and 13 mL of 1N sodium hydroxide was stirred at reflux for 8.5 hours. The solvent was removed under reduced pressure, the residue was acidified and the product was filtered. Recrystallization from ethyl acetate-hexane gave 0.94 (71% yield), mp 114°-117°, of 4-[[6-(3,4-dimethoxyphenyl)-6-oxohexyl]oxy]-2-hydroxy-3-propylbenzoic acid.

Anal. Calcd for $C_{24}H_{30}O_7$: C, 66.96, H, 7.02; Found: C, 66.98; H, 7.20

EXAMPLE 93

4-[[6-(3,4-Dihydroxyphenyl)-6-oxohexyl]oxy]-2-hydroxy-3-propylbenzoic acid

To 0.93 g of 4-[[6-(3,4-dimethoxyphenyl)-6-oxohexyl]oxy]-2-hydroxy-3-propylbenzoic acid suspended in 60 mL of methylene chloride and cooled at $-70°$ was added 7 mL of 1M boron tribromide in methylene chloride. The reaction mixture was stirred at $-70°$ for 1 hour and then at $-18°$ for 20 hours. Workup as in Example 32 and chromatography of the crude product on 100 g of silica gel using acetic acid:ethyl acetate-toluene (5:25:70) followed by recrystallization from ethyl acetate-hexane gave 0.42 g, mp 188°-191°, of 4-[[6-(3,4-dihydroxyphenyl)-6-oxohexyl]oxy]-2-hydroxy-3-propylbenzoic acid.

Anal. Calcd for $C_{22}H_{26}O_7$: C, 65.66; H, 6.51. Found: C, 65.29; H, 6.55

EXAMPLE 94

1-[2-Hydroxy-4-[4-(2,3-dimethoxyphenyl)butoxy]-3-propylphenyl]ethanone

A mixture of 4.36 g (15.9 mmol) of 1-(4-bromobutyl)-2,3-dimethoxybenzene, 3.10 g (15.9 mmol) of 1-(2,4-dihydroxy-3-propylphenyl)ethanone, 4.4 g (32 mmol) of potassium carbonate and 2.4 g (16 mmol) of sodium iodide in 100 mL of acetone was stirred at reflux for 30 hours. The reaction mixture was filtered and the filtrate was concentrated under reduced pressure. Purification by high pressure liquid chromatography using 20% ethyl acetate-hexane gave 5.07 g (88% yield) of 1-[2-

Hydroxy-4-[4-(2,3-dimethoxyphenyl)butoxy]-3-propylphenyl]-ethanone as an oil.

Anal. Calcd for $C_{23}H_{30}O_5$: C, 71.48; H, 7.82. Found: C, 71.58; H, 7.85.

Compounds of Examples 98–100 were prepared using the procedure of Example 97.

mL of toluene was stirred at reflux for 6.5 hours. The reaction mixture was washed with half-saturated brine, then with 1N sodium hydroxide, dried and concentrated under reduced pressure to an oil. Purification by HPLC using 25% ethyl acetate-hexane gave 4.05 g (75% yield), mp 72°–75°, of 1-[2-hydroxy-4-[5-(3,4-

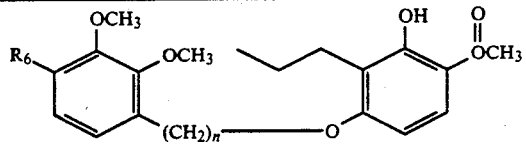

| Ex. No. | $R_6$ | n | Formula | Yield* % | % EtOAc-Hexane used in HPLC | Microanalysis Calcd C | Calcd H | Found C | Found H |
|---|---|---|---|---|---|---|---|---|---|
| 95 | H | 6 | $C_{25}H_{34}O_5$ | 88 | 20 | not submitted | | | |
| 96 | H | 8 | $C_{27}H_{38}O_5$ | 80 | 10 | 73.27 | 8.65 | 73.30 | 8.77 |
| 97 | $CH(CH_3)_2$ | 6 | $C_{28}H_{40}O_5$ | 57 | 5 | 73.65 | 8.83 | 73.75 | 8.95 |

*All compounds are oils

EXAMPLE 98

1-[2-Hydroxy-4-[4-(2,3-dihydroxyphenyl)butoxy]-3-propylphenyl]ethanone

To 5.02 g of 1-[2-hydroxy-4-[4-(2,3-dimethoxyphenyl)butoxy]-3-propylphenyl]ethanone in 300 mL of methylene chloride stirred and cooled at −70° was added 39 mL of 1M boron tribromide in methylene chloride. The reaction mixture was stirred at −70° for 30 minutes and kept at −20° for 5.5 hours. Workup as in Example 32 and recrystallization from acetone-hexane gave 3.81 g (82% yield), mp 103°–105° of 1-[2-hydroxy-4-[4-(2,3-dihydroxyphenyl)butoxy]-3-propylphenyl]ethanone.

Anal. Calcd for $C_{21}H_{26}O_5$: C, 70.37; H, 7.31. Found: C, 70.28; H, 7.43

Compounds of Examples 102–104 were prepared by the procedure of Example 101.

dimethoxyphenyl)pentyloxy]-3-propylphenyl]-1-ethanone.

Anal. Calcd for $C_{24}H_{32}O_5$: C, 71.97; H, 8.05. Found: C, 71.82; H, 8.05.

EXAMPLE 103

1-[4-[5-(3,4-Dihydroxyphenyl)pentyloxy]-2-hydroxy-3-propylphenyl]-1-ethanone

To 3.95 g (0.01 mole) of 1-[2-hydroxy-4-[5-(3,4-dimethoxyphenyl)pentyloxy)-3-propylphenyl]-1-ethanone in 80 mL of methylene chloride cooled at −70° was added 30 mL (0.03 mol) of 1M boron tribromide in methylene chloride. After 30 minutes at −70° and 6 hours at −20°, the reaction was worked up as in Example 32 and the product was recrystallized from ether:hexane to give 3.24 g (88% yield), mp 126°–127°, of 1-[4-[5-(3,4-dihydroxyphenyl)pentyloxy]-2-hydroxy-3-propylphenyl]-1-ethanone.

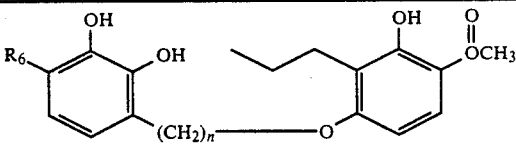

| Ex. No. | $R_6$ | n | Formula | Yield % | Recrystn Solvent mp (°C.) | Microanalysis Calcd C | Calcd H | Found C | Found H |
|---|---|---|---|---|---|---|---|---|---|
| 99 | H | 6 | $C_{23}H_{30}O_5$ | 90 | EtOAc hexane 106–108 | 71.48 | 7.82 | 71.31 | 7.84 |
| 100 | H | 8 | $C_{25}H_{34}O_5$ | 95 | Acetone hexane 116–118 | 72.44 | 8.27 | 72.32 | 8.27 |
| 101 | $CH(CH_3)_2$ | 6 | $C_{26}H_{36}O_5$ | 99 | HPLC 25% EtOAc hexane, oil | 72.87 | 8.47 | 72.63 | 8.64 |

EXAMPLE 102

1-[2-Hydroxy-4-[5-(3,4-dimethoxyphenyl)pentyloxy]-3-propylphenyl]-1-ethanone 3.0 g (0.013 mol) of 5-(3,4-dimethoxyphenyl)pentan-1-ol was converted to the mesylate as described in Example 6. A mixture of this mesylate, 2.6 g (0.013 mol) of 1-(2,4-dihydroxy-3-propylphenyl)ethanone, 2.8 g (0.02 mol) of potassium carbonate and 0.28 mL (0.9 mmol) of tris [2-(2-methoxyethoxy)ethyl]amine (TDA-1) in 75

Anal. Calcd. for $C_{22}H_{28}O_5$: C, 70.94; H, 7.58. Found: C, 70.80; H, 7.63.

EXAMPLE 104

4-(6-Bromohexyl)-2,3-dimethoxy-1,1′-biphenyl

A solution of 2.5M butyl lithium in hexane (16 mL, 0.04 mol) was added dropwise over 15 min. to a stirred solution of 8.3 g (0.039 mol) of 2,3-dimethoxybiphenyl [J. M. Bruce and F. K. Sutcliffe, J. Chem. Soc. 4435

(1955)] in 160 mL of anhydrous tetrahydrofuran cooled at 0° under argon. The reaction mixture was stirred at 0° for 2.5 hours and then refluxed for 30 min. After cooling to 5°, 6.3 mL (0.039 mole) of 1,6-dibromohexane was added. Stirring was continued at 5° for 30 min., at 25° for 30 min. and at reflux for 20 hours. Workup as in Example 1 gave an oil. Purification by HPLC using 3% ethyl acetate-hexane gave 5.7 g of unreacted 2,3-dimethoxybiphenyl and 3.3 g of 4-(6-bromohexyl)-2,3-dimethoxy-1,1'-biphenyl as an oil. The structure was confirmed by the nmr and mass spectra (molecular ion at m/e 376).

EXAMPLE 105

2-Hydroxy-4-[[6-(2,3-dimethoxy-1,1'-biphenyl)-4-yl]hexyl]oxy]-3-propylbenzoic acid phenylmethyl ester A mixture of 3.3 g (8.75 mmol) of 4-(6-bromohexyl)-2,3-dimethoxy-1,1'-biphenyl, 2.5 g (8.75 mmol) of 2,4-dihydroxy-3-propylbenzoic acid phenylmethyl ester, 1.8 g (13.1 mmol) of potassium carbonate and 0.2 mL (0.63 mmol) of tris[2-(2-methoxyethoxy)ethyl]amine (TDA-1) in 65 mL of anhydrous toluene was stirred at reflux for 30 hours. The reaction mixture was washed with half-saturated brine and then with 1N sodium hydroxide. After drying the organic layer, the solvent was removed under reduced pressure to give an oil which was purified by chromatography on 100 g of silica gel. Elution with 10% ethyl acetate-hexane gave 3.7 g (73% yield) of 2-hydroxy-4-[[6-(2,3-dimethoxy-1,1'-biphenyl)-4-yl]hexyl]oxy]-3-propylbenzoic acid phenylmethyl ester.

Anal. Calcd for $C_{37}H_{42}O_6$: C, 76.26; H, 7.26. Found: C, 76.11; H. 7.31.

EXAMPLE 106

2Hydroxy-4-[[6-(2,3-dimethoxy-1,1'-biphenyl)-4-yl]hexyl]oxy]-3-propylbenzoic acid A mixture of 3.76 g of 2-hydroxy-4-[[6-(2,3-dimethoxy-1,1'-biphenyl)-4-yl]hexyl]oxy]-3-propylbenzoic acid phenylmethyl ester and 0.30 g of 10% palladium on carbon in 80 mL of tetrahydrofuran was stirred in a hydrogen atmosphere for 17 hours. Workup as in Example 36 and recrystallization from hexane gave 2.4 g, mp 88°-80°, of 2-hydroxy-4-[[6-(2,3-dimethoxy-1,1'-biphenyl)-4-yl]hexyl]oxy]-3-propylbenzoic acid.

EXAMPLE 107

2-Hydroxy-4-[[6-(2,3-dihydroxy-1,1'-biphenyl)-4-yl]hexyl]oxy]-3-propylbenzoic acid To 1.72 g (3.5 mmol) of 2-hydroxy-4-[[6-(2,3-dimethoxy-1,1'-biphenyl)-4-hexyl]oxy]-3-propylbenzoic acid suspended in 150 mL of methylene chloride and cooled at −70° was added 10.5 mL (10.5 mmol) of 1M boron tribromide in methylene chloride. The reaction mixture was stirred at −70° for 20 min. and then kept at −18° for 17 hours. Workup as in Example 32 and two recrystallizations of the product from methylene chloride gave 1.03 g (63% yield), mp 151°-155°, of 2-hydroxy-4-[[6-(2,3-dihydroxy-1,1'-biphenyl)-4-yl]hexyl]oxy]-3-propylbenzoic acid.

Anal. Calcd. for $C_{28}H_{32}O_6$: C, 72.39; H, 6.94. Found: C, 72.32; H, 6.93.

EXAMPLE 108

2-Chloro-3,4-dimethoxybenzene hexanol

To 0.6 g (0.08 g-atoms) of lithium ribbon cut in small pieces in 40 mL of anhydrous ether stirred at room temperature under an argon atmosphere was added 9.5 g (0.04 mol) of 5-bromopentanol 2-ethoxyethyl ether. After about 1 mL was added, the reaction mixture was cooled to −5° and the rest of the bromo compound was added dropwise. Stirring at −5° was continued for 1 hour and then 6.0 g (0.03 mol) of 2-chloro-3,4-dimethoxybenzaldehyde [J. Weinstock et al., J. Med. Chem., 29, 2315 (1986)] in 50 mL of ether-20 mL of tetrahydrofuran was added dropwise over 1 hour. The cooling bath was removed and stirring was continued for 1 hour. The reaction mixture was worked up as in Example 10 to yield an oil which was dissolved in 25 mL of ethanol, 20 mL of water and 2 mL of concentrated hydrochloric acid was added. The solution was left at 25° for 45 minutes. Potassium carbonate was added with stirring until the mixture was basic. The ethanol was removed under reduced pressure and the product was extracted with ethyl acetate. The dried extract was concentrated to an oil (10 g). This was purified by HPLC using 60% ethyl acetate-hexane to give 2.9 g (34% yield), mp 75°-70°, of 6-(2-chloro-3,4-dimethoxybenzene)-6-hydroxyhexanol. This was dissolved in 50 mL of ethanol, 0.3 g of 10% palladium on carbon was added and the mixture was shaken under an initial hydrogen pressure of 54 psi for 21 hours. The reaction mixture was filtered through Celite and the filtrate was concentrated under reduced pressure to an oil. Purification by HPLC using 15% ethyl acetate-toluene gave 1.74 g (64% yield) of 2-chloro-3,4-dimethoxybenzene hexanol as an oil. The structure was confirmed by nmr and mass spectra (molecular ion at m/e 272).

EXAMPLE 109

4-[6-(2-Chloro-3,4-dimethoxyphenyl)hexyloxy]-2-hydroxy-3-propylbenzoic acid methyl ester To 1.74 g (6.4 mmol) of 2-chloro-3,4-dimethoxybenzene hexanol in 25 mL of methylene chloride cooled in an ice bath was added 1.8 mL (12.8 mmol) of triethylamine followed by 0.65 mL (8.3 mmol) of methanesulfonyl chloride. The reaction mixture was stirred with ice bath cooling for 80 min. and then worked up as in Example 3. The resulting mesylate, 1.24 g (5.9 mmol) of 2,4-dihydroxy-3-propylbenzoic acid methyl ester, 1.8 g (13 mmol) of potassium carbonate and 0.2 mL (0.7 mmole) of tris[2-(2-methoxyethoxy)ethyl]amine (TDA-1) in 40 mL of toluene was stirred at reflux for 39 hours. The reaction mixture was filtered and the filtrate was concentrated under reduced pressure. The crude product was purified by HPLC using 7% ethyl acetate-hexane to give 2.11 g (77% yield) of 4]-[6-(2-chloro-3,4-dimethoxyphenyl)hexyloxy]-2-hydroxy-3-propylbenzoic acid methyl ester as an oil. The structure was confirmed by the nmr and mass spectra (molecular ion at m/e 464).

EXAMPLE 110

4-[6-(2-Chloro-3,4-dimethoxyphenyl)hexyloxy]-2-hydroxy-3-propylbenzoic acid

A solution of 2.1 g (4.5 mmol) of 4-[6-(2-chloro-3,4-dimethoxyphenyl)hexyloxy]-2-hydroxy-3-propylbenzoic acid methyl ester in 50 mL of methanol and 15 mL dioxane and 18 mL of 1N sodium hydroxide was refluxed for 8 hours. The solvents were removed at reduced pressure, the residue was acidified and the product was extracted with ethyl acetate. The dried extract was concentrated and the residue was recrystallized from ethyl acetate-hexane to give 1.86 g (92% yield), mp 107°–108°, of 4-[6-(2-chloro-3,4-dimethoxyphenyl)-hexyloxy]-2-hydroxy-3-propylbenzoic acid.

Anal. Calcd for $C_{24}H_{31}ClO_6$: C, 63.92; H, 6.93; Cl, 7.86. Found: C, 63.73; H, 6.97; Cl, 7.98.

EXAMPLE 111

4-[6-(2-Chloro-3,4-dihydroxyphenyl)hexyloxy]-2-hydroxy-3-propylbenzoic acid

To 1.80 g (4 mmol) of 4-[6-(2-chloro-3,4-dimethoxyphenyl)hexyloxy]-2-hydroxy-3-propyl benzoic acid suspended in 120 mL of methylene chloride and cooled at −70° was added 14 mL (14 mmol) of 1M boron tribromide in methylene chloride. The reaction mixture was stirred at −70° for 15 min. and kept at −18° for 6 hours. Workup as in Example 32 and two recrystallizations from ethyl acetate-hexane gave 1.03 g (61% yield), mp 145°–146°, of 4-[6-(2-chloro-3,4-dihydroxyphenyl)hexyloxy]-2-hydroxy-3-propylbenzoic acid.

Anal. Calcd for $C_{22}H_{27}ClO_6$: C, 62.48; H, 6.44; Cl, 8.38. Found: C, 62.26; H, 6.32; Cl, 8.54.

EXAMPLE 112

1-(5-Bromopentyl)-6-chloro-2,3-dimethoxybenzene

To 4.0 g of 1-(5-bromopentyl)-2,3-dimethoxybenzene in 50 mL of methylene chloride cooled in an ice bath was added 18 mL of 0.8M chlorine in methylene chloride. The reaction mixture was kept at 0° for 3 hours and then was concentrated under reduced pressure to yield an oil. Purification by HPLC using 30% toluene-hexane gave 2.60 g (58% yield) of 1-(5-bromopentyl)-6-chloro-2,3-dimethoxybenzene. The nmr spectrum was consistent with the structure and the mass spectrum gave a molecular ion at m/z 320 ($C_{13}H_{18}BrClO_2$).

EXAMPLE 113

1-(5-Bromopentyl)-5,6-dichloro-2,3-dimethoxybenzene

To 4.0 g of 1-(5-bromopentyl)-2,3-dimethoxy benzene in 50 mL of methylene chloride cooled in an ice bath was added 18 mL of 0.8M chlorine in methylene chloride. After 15 minutes, 17 mL of 0.88M chlorine in methylene chloride was added. The reaction mixture was kept at 0° for 3 hours and then was concentrated under reduced pressure to yield an oil. Purification by HPLC using 30% toluene-hexane gave 2.03 g (41% yield) of 1-(5-bromopentyl)-5,6-dichloro-2,3-dimethoxybenzene. The nmr spectrum was consistent with the structure and the mass spectrum gave a molecular ion at m/z 354 ($C_{13}H_{17}BrCl_2O_2$).

EXAMPLE 114

1-(5-Bromopentyl)-2,3-dimethoxy-4,5,6-trichlorobenzene

To 1.9 g of 1-(5-bromopentyl)-2,3-dimethoxy benzene in 25 mL of methylene chloride cooled in an ice bath was added 23 mL of 0.88M chlorine in methylene chloride. After 1.5 hours at 0°, 5 mL of 1.35M chlorine in methylene chloride was added. The reaction mixture was kept at 0° for 17 hours and then was concentrated under reduced pressure to yield an oil. Purification by HPLC using 25% toluene-hexane gave 1.48 g (56% yield) of 1-(5-bromopentyl)-2,3-dimethoxy-4,5,6-trichlorobenzene. The nmr spectrum was consistent with the structure and the mass spectrum gave a molecular ion at m/z 388 ($C_{13}H_{16}BrCl_3O_2$).

EXAMPLE 115

6-(6-Chloro-3,4-dimethoxyphenyl)hexan-1-ol

To 1.40 g of 6-(3,4-dimethoxyphenyl)hexan-1-ol in 25 mL of methylene chloride cooled in a ethanol-dry ice bath was added 4.6 mL of 1.35M chlorine in methylene chloride. The reaction mixture was kept at −75° for 1.5 hours, at −18° for 16 hours and then at 0° for 24 hours. After concentration under reduced pressure, the crude product was purified by HPLC to give 6-(6-chloro-3,4-dimethoxyphenyl)hexan-1-ol as an oil. The nmr spectrum was consistent with the structure and the mass spectrum gave a molecular ion at m/z 272 ($C_{14}H_{21}ClO_3$).

EXAMPLE 116

6-Bromo-1-[3,4-dimethoxy-5-(1-methylethyl)phenyl]-1-hexanone

A solution of 5.0 g (0.028 mol) of 3-(1-methylethyl)-1,2-dimethoxybenzene in 5 mL of methylene chloride was added to an ice cooled mixture of 4.4 g (0.033 mol) of aluminum chloride and 7.0 g (0.033 mol) of 6-bromohexanoyl chloride in 50 mL of methylene chloride. The reaction mixture was kept at 0° for 18 hours. Water was added and the organic layer was separated and washed with sodium bicarbonate solution. The dried extract was concentrated under reduced pressure to an oil which was purified by HPLC using 5% ethyl acetate-hexane to give 8.1 g (82% yield) of 6-bromo-1-[3,4-dimethoxy-5-(1-methylethyl)phenyl]-1-hexanone as an oil. The nmr spectrum was consistent with the structure and the mass spectrum gave the molecular ion at m/z 356 ($C_{17}H_{25}BrO_3$).

EXAMPLE 117

6-Bromo-1-(3,4-dimethoxy-2,5-dimethylphenyl)-1-hexanone

A solution of 0.227 g (1.5 mmol) of 3,6-dimethylveratrole in 1 mL of methylene chloride was added to an ice cooled mixture of 0.245 g (1.8 mmol) of aluminum chloride and 0.416 g (1.9 mmol) of 6-bromohexanoyl chloride in 3 mL of methylene chloride. The reaction mixture was kept at 0° for 19 hours. Water was added and the organic layer was separated and washed with sodium bicarbonate solution. The dried extract was concentrated to an oil which was chromatographed on 60 g of silica gel using 10% ethyl acetate-hexane to give 0.235 g of 6-bromo-1-(3,4-dimethoxy-2,5-dimethylphenyl)-1-hexanone as an oil. The nmr spectrum was consistent with the structure and the mass spectrum gave the molecular ion at m/z 342 ($C_{16}H_{23}BrO_3$)

EXAMPLE 118

4-Chloro-1-[3,4-dimethoxy-6-fluorophenyl]-1-hexanone

A solution of 0.1056 g (0.64 mmol) of 4-fluoroveratrole in 1 mL of methylene chloride was added to a mixture of 0.2289 g (1.7 mmol) of aluminum chloride and 0.09 mL (0.8 mmol) of 4-chlorobutyryl chloride in 2 mL of methylene chloride at 25°. The reaction mixture was stirred at 25° for 22 hours. Water was added and the organic layer was separated and washed with sodium bicarbonate solution. The dried extract was concentrated under reduced pressure to an oil which was chromatographed on 10 g of silica gel using 25% ethyl acetatehexane to give 0.041 g, mp 81°–82°, of 4-chloro-[3,4-dimethoxy-6-fluorophenyl]-1-hexanone.

The nmr spectrum was consistent with the structure and the mass spectrum gave the molecular ion at m/z 260 ($C_{12}H_{14}ClFO_3$)

EXAMPLE 119

4-[5-(2-Chloro-5,6-dimethoxyphenyl)pentyloxy]-2-hydroxy-3-propylbenzoic acid methyl ester A mixture of 2.60 g (8.1 mmol) of 1-(5-bromopentyl)-6-chloro-2,3-dimethoxybenzene, 1.65 g (7.8 mmol) of 2,4-dihydroxy-3-propylbenzoic acid methyl ester and 5.0 g (36 mmol) of anhydrous potassium carbonate in 60 mL of acetone and 6 mL of DMF was stirred at reflux for 24 hours. The reaction mixture was filtered and the filtrate was concentrated under reduced pressure. Crystallization from hexane gave 2.95 g (83% yield), mp 53°–55°, of 4-[5-(2-chloro-5,6-dimethoxyphenyl)pentyloxy]-2-hydroxy-3-propylbenzoic acid methyl ester.

EXAMPLE 120

4-[5-(2-Chloro-5,6-dimethoxyphenyl)pentyloxy]-2-hydroxy-3-propylbenzoic acid

A solution of 2.95 g (6.7 mmol) of 4-[5-(2-chloro-5,6-dimethoxyphenyl)pentyloxy]-2-hydroxy-3-propylbenzoic acid methyl ester in 80 mL of methanol and 20 mL (20 mmol) of 1N sodium hydroxide was stirred at reflux for 4 hours. Workup as in Example 24 and recrystallization from ether-hexane gave 2.70 g (96% yield) mp 140°–142°, of 4-[5-(2-chloro-5,6-dimethoxyphenyl)pentyloxy]-2-hydroxy-3-propylbenzoic acid.

Anal. Calcd for $C_{23}H_{29}ClO_6$: C, 63.23; H, 6.69; Cl, 8.11. Found: C, 63.23; H, 6.75; Cl, 8.22.

EXAMPLE 121

4-[5-(2-Chloro-5,6-dihydroxyphenyl)pentyloxy]-2-hydroxy-3-propylbenzoic acid

To 2.70 g (6.2 mmol) of 4-[5-(2-chloro-5,6-dimethoxyphenyl)pentyloxy]-2-hydroxy-3-propylbenzoic acid suspended in 250 mL of methylene chloride and stirred at −60° was added 18.6 mL (18.6 mmol) of 1M boron tribromide in methylene chloride. The reaction mixture was stirred at −60° for 20 minutes and was then kept at −20° for 19 hours. Water was added and the product was extracted with ether. The extract was concentrated under reduced pressure and the residue was dissolved in 50 mL of ether and was shaken vigorously for 20 minutes with 50 mL of 1N hydrochloric acid. The dried extract was concentrated under reduced pressure and the residue was crystallized from ether-chloroform to give 1.10 g, mp 178°–181°, of 4-[5-(2-chloro-5,6-dihydroxy-phenyl)pentyloxy]-2-hydroxy-3-propylbenzoic acid.

Anal. Calcd for $C_{21}H_{25}ClO_6$: C, 61.69; H, 6.16; Cl, 8.67. Found: C, 61.69; H, 6.07; Cl, 8.75

EXAMPLE 122

4-[5-(2,3-Dichloro-5,6-dimethoxyphenyl)pentyloxy]-2-hydroxy-3-propylbenzoic acid methyl ester A mixture of 2.03 g (5.7 mmol) of 1-(5-bromopentyl)-2,3-dichloro-5,6-dimethoxybenzene, 1.15 g (5.5 mmol) of 2,4-dihydroxy-3-propylbenzoic acid methyl ester and 3.5 g (22 mmol) of potassium carbonate in 50 mL of acetone and 5 mL of DMF (dimethylformamide) was stirred at reflux for 24 hours. The reaction mixture was filtered and the filtrate was concentrated under reduced pressure. Crystallization from ether-hexane gave 1.5 g (56% yield), mp 113°–115°, of 4-[5-(2,3-dichloro-5,6-dimethoxyphenyl)pentyloxy]-2-hydroxy-3-propylbenzoic acid methyl ester.

EXAMPLE 123

4-[5-(2,3-Dichloro-5,6-dimethoxyphenyl)pentyloxy]-2-hydroxy-3-propylbenzoic acid A solution of 1.5 g (3.2 mmol) of 4-[5-(2,3-dichloro-5,6-dimethoxyphenyl)pentyloxy]-2-hydroxy-3-propylbenzoic acid methyl ester in 40 mL of methanol and 10 mL (10 mmol) of 1N sodium hydroxide was stirred at reflux for 5 hours. Workup as in Example 24 and recrystallization from ether-hexane gave 1.2 g (80% yield), mp 152°–154°, of 4-[5-(2,3-dichloro-5,6-dimethoxyphenyl)pentyloxy]-2-hydroxy-3-propylbenzoic acid.

Anal. Calcd. for $C_{23}H_{28}Cl_2O_6$: C, 58.61; H, 5.99; Cl, 15.04. Found: C, 58.78; H, 6.07; Cl, 15.13

EXAMPLE 124

4-[5-(2,3-Dichloro-5,6-dihydroxyphenyl)pentyloxy]-2-hydroxy-3-propylbenzoic acid To 1.2 g (2.5 mmol) of 4-[5-(2,3-dichloro-5,6-dimethoxyphenyl)pentyloxy]-2-hydroxy-3-propylbenzoic acid suspended in 100 mL of methylene chloride and stirred at −60°, was added 7.5 mL (7.5 mmol) of 1M boron tribromide in methylene chloride. After stirring at −60° for 30 minutes the reaction mixture was kept at −20° for 20 hours. Workup as in example 124 gave a solid residue which was recrystallized from ether chloroform to give 0.42 g, mp 159°–164°, of 4-[5-(2,3-dichloro-5,6-dihydroxyphenyl)pentyloxy]-2-hydroxy-3-propylbenzoic acid.

EXAMPLE 125

4-[5-(2,3,4-Trichloro-5,6-dimethoxyphenyl)pentyloxy]-2-hydroxy-3-propylbenzoic acid methyl ester A mixture of 1.48 g (3.8 mmol) of 1-(5-bromopentyl)-5,6-dimethoxy-2,3,4-trichlorobenzene, 0.76 g (3.6 mmol) of 2,4-dihydroxy-3-propylbenzoic acid methyl ester and 4.6 g (33 mmol) of potassium carbonate in 30 mL of acetone and 3 mL of DMF was stirred at reflux for 23 hours. The reaction mixture was filtered and the filtrate was concentrated under reduced pressure. Crystallization from ether-hexane gave 1.5 g (76% yield), mp 84°–87°, of 4-[5-(2,3,4-trichloro-5,6-dimethoxyphenyl)pentyloxy]-2-hydroxy-3-propylbenzoic acid methyl ester.

Anal. Calcd. for $C_{24}H_{29}Cl_3O_6$: C, 55.45; H, 5.62; Cl, 20.46. Found: C, 55.53; H, 5.70; Cl, 20.20.

EXAMPLE 126

4-[5-(2,3,4-Trichloro-5,6-dimethoxyphenyl)pentyloxy]-2-hydroxy-3-propylbenzoic acid A solution of 1.5 g (2.3 mmol) of 4-[5-(2,3,4-trichloro-5,6-dimethoxyphenyl)pentyloxy]-2-hydroxy-3-propylbenzoic acid methyl ester in 40 mL of methanol and 8.7 mL (8.7 mmol) of 1N sodium hydroxide was stirred at reflux for 5 hours. Workup as in Example 24 and recrystallization from ethyl acetate-hexane gave 1.3 g (89% yield), mp 148°–150°, of 4-[5-(2,3,4-trichloro-5,6-dimethoxyphenyl)pentyloxy]-2-hydroxy-3-propylbenzoic acid.

Anal. Calcd for $C_{23}H_{27}Cl_3O_6$: C, 54.61; H, 5.38; Cl, 21.03. Found: C, 54.60; H, 5.48; Cl, 20.88.

EXAMPLE 127

4-[5-(2,3,4-Trichloro-5,6-dihydroxyphenyl)pentyloxy]-2-hydroxy-3-propylbenzoic acid To 1.3 g (2.6 mmol) of 4-[5-(2,3,4-trichloro-5,6-dimethoxyphenyl)pentyloxy-2-hydroxy-3-propylbenzoic acid suspended in 110 mL of methylene chloride and stirred at −60°, was added 8.0 mL (8 mmol) of 1M boron tribromide in methylene chloride. The reaction mixture was stirred at −60° for 1 hour and then kept at −20° for 18 hours. Workup as in Example 124 gave a solid which was recrystallized from ether-hexane to give 0.9 g (73% yield), mp 193°–196°, of 4-[5-(2,3,4-trichloro-5,6-dihydroxyphenyl)pentyloxy]-2-hydroxy-3-propylbenzoic acid.

Anal. Calcd for $C_{21}H_{23}Cl_3O_6$: C, 52.79; H, 4.85; Cl, 22.26. Found: C, 52.58; H, 4.84; Cl, 22.51.

EXAMPLE 128

4-[[6-(3,4-Dimethoxy-2,5-dimethylphenyl)-6-oxohexyl]oxy]-2-hydroxy-3-propylbenzoic acid methyl ester A mixture of 2.50 g (7.29 mmol) of 6-bromo-1-(3,4-dimethoxy-2,5-dimethylphenyl)-1-hexanone, 1.53 g (7.29 mmol) of 2,4-dihydroxy-3-propylbenzoic acid methyl ester and 3.30 g (24 mmol) of potassium carbonate in 50 mL of acetone and 5 mL of DMF was stirred and heated at reflux for 26 hours. After workup as in Example 16 the crude product was purified by HPLC using 10% ethyl acetate-hexane to give 3.40 g (98% yield) of 4-[[6-(3,4-dimethoxy-2,5-dimethylphenyl)-6-oxohexyl]oxy]-2-hydroxy-3-propyl benzoic acid methyl ester as an oil. The nmr spectrum was consistent with the structure.

EXAMPLE 129

4-[[6-(3,4-Dimethoxy-2,5-dimethylphenyl)-6-oxohexyl]oxy]-2-hydroxy-3-propylbenzoic acid.

A solution of 3.40 g (7.2 mmol) of 4-[[6-(3,4-dimethoxy-2,5-dimethylphenyl)-6-oxohexyl]oxy]-2-hydroxy-3-propylbenzoic acid methyl ester in 90 mL of methanol and 30 mL (30 mmol) of 1.0N sodium hydroxide was stirred at reflux for 5 hours. Workup as in example 24 and recrystallization of the crude product from ether-hexane gave 3.00 g (91% yield), mp 92°–94°, of 4-[[6-(3,4-dimethoxy-2,5-dimethylphenyl)-6-oxohexyl]oxy]-2-hydroxy-3-propylbenzoic acid.

Anal. Calcd. for $C_{26}H_{34}O_7$: C, 68.10; H, 7.47. Found: C, 68.02; H, 7.60.

EXAMPLE 130

4-[[6-(3,4-Dihydroxy-2,5-dimethylphenyl)-6-oxohexyl]oxy]-2-hydroxy-3-propylbenzoic acid To 1.00 g (2.2 mmol) of 4-[[6-(3,4-dimethoxy-2,5-dimethylphenyl)-6-oxohexyl]oxy]-2-hydroxy-3-propylbenzoic acid in 100 mL of methylene chloride was added 6.6 mL (6.6 mmol) of 1M boron tribromide in methylene chloride with cooling at −70°. The mixture was stirred at −70° for 1 hour and then kept at −20° for 16 hours. Workup as in Example 32 and recrystallization of the crude product from ether-hexane gave 0.60 g (63% yield), mp 121°–125°, of 4-[[6-(3,4-dihydroxy-2,5-dimethylphenyl)-6-oxohexyl]oxy]-2-hydroxy-3-propylbenzoic acid.

Anal. Calcd. for $C_{24}H_{30}O_7$: C, 66.96; H, 7.02. Found: C, 66.70; H, 7.02

EXAMPLE 131

4-[[6-[3,4-Dimethoxy-5-(1-methylethyl)phenyl]-6-oxohexyl]oxy]-2-hydroxy-3-propylbenzoic acid methyl ester A mixture of 6.0 g (0.017 mol) of 6-bromo-1-[3,4-dimethoxy-5-(1-methylethyl)phenyl]-1-hexanone, 3.39 g (0.016 mol) of 2,4-dihydroxy-3-propylbenzoic acid methyl ester and 7.0 g (0.051 mol) of potassium carbonate in 120 mL of acetone and 12 mL of DMF was stirred at reflux for 19 hours. After workup as in Example 16, the crude product was purified by HPLC using 16% ethyl acetate-hexane to give 7.7 g (98% yield) of 4-[[6-[3,4-dimethoxy-5-(1-methylethyl)phenyl]-6-oxohexyl]oxy]-2-hydroxy-3-propylbenzoic acid methyl ester as an oil. The nmr spectrum was consistent with the structure.

EXAMPLE 132

4-[[6-[3,4-Dimethoxy-5-(1-methylethyl)phenyl]-6-oxohexyl]oxy]-2-hydroxy-3-propylbenzoic acid A solution of 7.7 g (0.016 mol) of 4-[[6-[3,4-dimethoxy-5-(1-methylethyl-phenyl)-6-oxohexyl]oxy]-2-hydroxy-3-propylbenzoic acid methyl ester in 80 mL of methanol and 60 mL (0.06 mol) of 1.0N sodium hydroxide was stirred at reflux for 5 hours. Workup as in Example 24 and recrystallization of the crude product from ethyl acetate-hexane gave 6.6 g (89% yield), mp 113°–115°, of 4-[[6-[3,4-dimethoxy-5-(1-methylethyl)-phenyl]-6-oxohexyl]oxy]-2-hydroxy-3-propylbenzoic acid.

Anal. Calcd for $C_{27}H_{36}O_7$: C, 68.62; H, 7.68. Found: C, 68.50; H, 7.84.

EXAMPLE 133

4-[[6-[3,4-Dihydroxy-5-(1-methylethyl)phenyl]-6-oxohexyl]oxy]-2-hydroxy-3-propylbenzoic acid To 2.0 g (4.2 mmol) of 4-[[6-[3,4-dimethoxy-5-(1-methylethyl)phenyl]-6-oxohexyl]oxy]-2-hydroxy-3-propylbenzoic acid in 200 mL of methylene chloride cooled at −65° was added 13 mL (13 mmol) of 1.0M boron tribromide in methylene chloride. The suspension was stirred at −50° for 2 hours and then kept at −20° for 16 hours. Workup as in Example 32 and recrystallization of the crude product from ether-hexane gave 1.5 g (81% yield), mp 169°–171°, of 4-[[6-[3,4-dihydroxy-5-(1-methylethyl)phenyl]-6-oxohexyl]oxy]-2-hydroxy-3-propylbenzoic acid.

Anal. Calcd for $C_{25}H_{32}O_7$: C, 67.55; H, 7.26. Found: C, 67.45; H, 7.19.

EXAMPLE 134

4-[[6-[3,4-Dimethoxy-5-(1-methylethyl)phenyl]hexyloxy]-2-hydroxy-3-propylbenzoic acid A mixture of 2.5 g of 4-[[6-[3,4-dimethoxy-5-(1-methylethyl)phenyl]-6-oxohexyl]oxy]-2-hydroxy-3-propylbenzoic acid in 50 mL of tetrahydrofuran containing 2 drops of concentrated sulfuric acid and 0.5 g of 10% palladium on carbon was shaken on a Parr hydrogenator under an initial hydrogen pressure of 52 psi for 20 hours. The reaction mixture was filtered through a Celite pad and the filtrate was concentrated under reduced pressure. The residue was dissolved in ether and washed with water. The extract was dried and concentrated to a solid which was recrystallized from hexane to give 2.4 g, mp 106°–108°, of 4-[[6-[3,4-dimethoxy-5-

(1-methylethyl)phenyl]hexyloxy]-2-hydroxy-3-propylbenzoic acid.

Anal. Calcd for $C_{27}H_{38}O_6$: C, 70.72; H, 8.35. Found: C, 70.71; H, 8.39

EXAMPLE 135

4-[[6-[3,4-Dihydroxy-5-(1-methylethyl)phenyl]hexyloxy]-2-hydroxy-3-propylbenzoic acid To 2.43 g (5.3 mmol) of 4-[[6-(3,4-dimethoxy-5-(1-methylethyl)phenyl]hexyloxy]-2-hydroxy-3-propylbenzoic acid in 250 mL of methylene chloride cooled at −75° was added 16 mL (16 mmol) of 1M boron tribromide in methylene chloride. The reaction mixture was stirred at −75° for 1 hour and then was kept at −20° for 17 hours. Workup as in Example 32 and recrystallization from ether-hexane gave 1.20 g, mp 138°–140°, of 4-[[6-[3,4-dihydroxy-5-(1-methylethyl)phenyl]hexyloxy]-2-hydroxy-3-propylbenzoic acid.

Anal. Calcd for $C_{25}H_{34}O_6$: C, 69.74; H, 7.96. Found: C, 69.81; H, 8.02

EXAMPLE 136

4-[[6-(3,4-Dimethoxy-2,5-dimethylphenyl)hexyloxy]-2-hydroxy-3-propylbenzoic acid A mixture of 1.45 g of 4-[[6-(3,4-dimethoxy-2,5-dimethylphenyl)-6-oxohexyl]oxy]-2-hydroxy-3-propylbenzoic acid in 40 mL of tetrahydrofuran containing 2 drops of concentrated sulfuric acid and 0.4 g of 10% palladium on carbon was shaken on a Parr hydrogenator under an initial hydrogen pressure of 52 psi for 20 hours. The reaction mixture was worked up as in Example 137 and the product was recrystallized from ether-hexane to give 1.20 g, mp 109°–112°, of 4-[[6-(3,4-dimethoxy-2,5-dimethylphenyl)hexyloxy]-2-hydroxy-3-propylbenzoic acid.

Anal. Calcd. for $C_{26}H_{36}O_6$: C, 70.24; H, 8.16. Found: C, 70.11; H, 8.17.

EXAMPLE 137

4-[[6-(3,4-Dihydroxy-2,5-dimethylphenyl)hexyloxy]-2-hydroxy-3-propylbenzoic acid To 1.2 g (2.7 mmol) of 4-[[6-(3,4-dimethoxy-2,5-dimethylphenyl)hexyloxy]-2-hydroxy-3-propylbenzoic acid in 120 mL of methylene chloride cooled at −75° was added 8 mL (8 mmol) of 1M boron tribromide in methylene chloride. The reaction mixture was stirred at −75° for 1 hour and kept at −20° for 17 hours. Workup as in Example 32 and recrystallization of the crude product from ether-hexane gave 0.60 g, mp 170°–171°, of 4-[[6-(3,4-dihydroxy-2,5-dimethylphenyl)hexyloxy]-2-hydroxy-3-propylbenzoic acid.

Anal. Calcd for $C_{24}H_{32}O_6$: C, 69.21; H, 7.74. Found: C, 68.93; H, 7.80.

EXAMPLE 138

6-Bromo-1-(2-fluoro-4,5-dimethoxyphenyl)-1-hexanone

A solution of 5.3 g (0.034 mol) of 1,2-dimethoxy-4-fluorobenzene in 25 mL of methylene chloride was added to a solution of 5.4 g (0.041 mol) of aluminum chloride and 8.7 g (0.041 mol) of 6-bromohexanoyl chloride in 60 mL of methylene chloride cooled in an ice bath. The resulting solution was kept at 0° for 5 hours and then worked up as in Example 131. The crude product was recrystallized from methylene chloride-ether to give 6.98 g (62% yield), mp 81°–83°, of 6-bromo-1-(2-fluoro-4,5-dimethoxyphenyl)-1-hexanone. The nmr spectrum was consistent with the structure and the mass spectrum gave a molecular ion at m/z 332 ($C_{14}H_{18}BrFO_3$).

EXAMPLE 139

4-[[6-(2-Fluoro-4,5-dimethoxyphenyl)-6-oxohexyl]oxy]-2-hydroxy-3-propylbenzoic acid methyl ester A mixture of 4.0 g (12 mmol) of 6-bromo-1-(2-fluoro-4,5-dimethoxyphenyl)-1-hexanone, 2.5 g (12 mmol) of 2,4-dihydroxy-3-propylbenzoic acid methyl ester and 5.0 g (36 mmol) of potassium carbonate in 80 mL of acetone and 8 mL of DMF was stirred at reflux for 86 hours. DMF (12 mL) and potassium carbonate (3 g) were added and reflux was continued for 18 hours. Workup as in Example 16 and recrystallization of the crude product from ethyl acetate gave 4.3 g (78% yield), mp 127°–129°, of 4-[[6-(2-fluoro-4,5-dimethoxyphenyl)-6-oxohexyl]oxy]-2-hydroxy-3-propylbenzoic acid methyl ester.

Anal. Calcd for $C_{25}H_{31}FO_7$: C, 64.92; H, 6.76; F, 4.11. Found: C, 64.68; h, 6.81; F, 4.19

EXAMPLE 140

4-[[6-(2-Fluoro-4,5-dimethoxyphenyl)-6-oxohexyl]oxy]-2-hydroxy-3-propylbenzoic acid A solution of 4.3 g (9.3 mmol) of 4-[[6-(2-fluoro-4,5-dimethoxy-6-oxohexyl]oxy]-2-hydroxy-3-propylbenzoic acid methyl ester in 135 mL of methanol and 45 mL (45 mmol) of 1N sodium hydroxide was stirred at reflux for 5 hours. Workup as in Example 24 and recrystallization of the crude product from ethyl acetate-hexane gave 3.7 g, mp 146°–147°, of 4-[[6-(2-fluoro-4,5-dimethoxyphenyl)-6-oxohexyl]oxy]-2-hydroxy-3-propylbenzoic acid.

Anal. Calcd. for $C_{24}H_{29}FO_7$: C, 64.27; H, 6.52; F, 4.24, Found: C, 64.14; H, 6.47; F, 4.30

EXAMPLE 141

4-[[6-(2-Fluoro-4,5-dihydroxyphenyl)-6-oxohexyl]oxy]-2-hydroxy-3-propylbenzoic acid To 2.0 g (4.46 mmol) of 4-[[6-(2-fluoro-4,5-dimethoxyphenyl)-6-oxohexyl]oxy]-2-hydroxy-3-propylbenzoic acid in 200 mL of methylene chloride cooled at −75° was added 13 mL (13 mmol) of 1M boron tribromide in methylene chloride. The reaction mixture was stirred at −75° for 1 hour and kept at −20° for 17 hours. Additional boron tribromide (7 mL) was added and the mixture was stirred at −5° for 5 hours. Workup as in Example 32 and recrystallization of the crude product from ether-hexane gave 0.84 g, mp 193°–195°, of 4-[[6-(2-fluoro-4,5-dihydroxyphenyl)-6-oxohexyl]oxy]-2-hydroxy-3-propylbenzoic acid.

Anal. Calcd for $C_{22}H_{25}FO_7$: C, 62.85; H, 5.99. Found: C, 62.56; H, 6.01.

EXAMPLE 142

4-[6-(2-Fluoro-4,5-dimethoxyphenyl)-hexyloxy]-2-hydroxy-3-propylbenzoic acid

A mixture of 0.400 g of 4-[[6-(2-fluoro-4,5-dimethoxyphenyl)-6-oxohexyl]oxy]-2-hydroxy-3-propylbenzoic acid and 0.150 g of 10% palladium on carbon in 20 mL of tetrahydrofuran containing 2 drops of concentrated sulfuric acid was shaken under an initial hydrogen pressure of 53 psi on a Parr hydrogenator for 20 hours. The reaction mixture was filtered through a Celite pad and the filtrate was concentrated under reduced pressure to a solid. Recrystallization from ethyl acetate-hexane gave 0.37 g mp 127°–130°, of 4-[6-(2-fluoro-4,5-dimethoxyphenyl)-hexyloxy]-2-hydroxy-3-propylbenzoic acid.

Anal. Calcd. for $C_{24}H_{31}FO_6$: C, 66.34; H, 7.19; F, 4.37. Found: C, 66.33; H, 7.25; F, 4.23

EXAMPLE 143

4-[6-(2-Fluoro-4,5-dihydroxyphenyl)hexyloxy]-2-hydroxy-3-propylbenzoic acid

To 0.36 g of 4-[6-(2-fluoro-4,5-dimethoxyphenyl)hexyloxy]-2-hydroxy-3-propylbenzoic acid in 60 mL of methylene chloride cooled at −75° was added 2.8 mL of 1M boron tribromide in methylene chloride. The reaction mixture was stirred at −75° for 30 minutes and then was kept at −20° for 20 hours. Workup as in Example 32 and recrystallization of the crude product from ether-hexane gave 0.18 g, mp 110°–11°, of 4-[6-(2-fluoro-4,5-dihydroxyphenyl)hexyloxy]-2-hydroxy-3-propylbenzoic acid.

EXAMPLE 144

6-Bromo-1-(3,4-dimethoxy-2,5,6-trimethylphenyl)-1-hexanone

A solution of 2.956 g (16 mmol) of 1,2-dimethoxy-3,4,6-trimethylbenzene in 10 mL of methylene chloride was added to 2.40 g (18 mmol) of aluminum chloride and 3.80 g (18 mmol) of 6-bromohexanoyl chloride in 30 mL of methylene chloride cooled in an ice bath. The solution was kept at 3° for 45 minutes and then at 23° for 42 hours. An additional 2.0 g of aluminum chloride and 3.0 g of 6-bromohexanoyl chloride were added and the reaction mixture was stirred at reflux for 22 hours. Workup as in Example 131 and purification by HPLC using 4% ethyl acetate-hexane gave 0.95 g of 6-bromo-1-(3,4-dimethoxy-2,5,6-trimethylphenyl)-1-hexanone as an oil. The nmr spectrum was consistent with the structure and the mass spectrum gave a molecular ion at m/z 356 ($C_{17}H_{25}BrO_3$).

EXAMPLE 145

4-[[6-(3,4-Dimethoxy-2,5,6-trimethylphenyl)-6-oxohexyl]oxy]-2-hydroxy-3-propylbenzoic acid methyl ester A mixture of 0.194 g (2.6 mmol) of 6-bromo-1-(3,4-dimethoxy-2,5,6-trimethylphenyl)-1-hexanone, 0.55 g (2.6 mmol) of 2,4-dihydroxy-3-propylbenzoic acid methyl ester and 1.10 g (7.8 mmol) of potassium carbonate in 20 mL of acetone and 2 mL of DMF was stirred at reflux for 17 hours. After workup as in Example 16, the crude product was purified by chromatography on 100 g of silica gel. Elution with 10% ethyl acetate-hexane gave 1.05 g (83% yield) of 4-[[6-(3,4-dimethoxy-2,5,6-trimethylphenyl)-6-oxohexyl]oxy]-2-hydroxy-3-propylbenzoic acid methyl ester. The nmr spectrum was consistent with the structure and the mass spectrum gave the molecular ion at m/z 486 ($C_{28}H_{28}O_7$).

EXAMPLE 146

4-[[6-(3,4-Dimethoxy-2,5,6-trimethylphenyl)-6-oxohexyl]oxy]-2-hydroxy-3-propylbenzoic acid A solution of 1.05 g (2.16 mmol) of 4-[[6-(3,4-dimethoxy-2,5,6-trimethylphenyl)-6-oxohexyl]oxy]-2-hydroxy-3-propylbenzoic acid methyl ester in 30 mL of methanol and 7 mL (7 mmol) of 1N sodium hydroxide was stirred at reflux for 7 hours. Workup as in Example 24 gave 0.98 g, mp 108°–112°, of 4-[[6-(3,4-dimethoxy-2,5,6-trimethylphenyl)-6-oxohexyl]oxy]-2-hydroxy-3-propylbenzoic acid.

EXAMPLE 147

4-[[6-(3,4-Dihydroxy-2,5,6-trimethylphenyl)-6-oxohexyl]oxy]-2-hydroxy-3-propylbenzoic acid To 0.98 g (2.07 mmol) of 4-[[6-(3,4-dimethoxy-2,5,6-trimethylphenyl)-6-oxohexyl]oxy]-2-hydroxy-3-propylbenzoic acid in 100 mL of methylene chloride cooled at −75° was added 7 mL (7 mmol) of 1M boron tribromide in methylene chloride. The reaction mixture was stirred at −75° for 30 minutes and then was kept at −20° for 18 hours. Workup as in Example 32 and recrystallization of the crude product from ether-hexane gave 0.51 g, mp 169°–170° of 4-[[6-(3,4-dihydroxy-2,5,6-trimethylphenyl)-6-oxohexyl]oxy]-2-hydroxy-3-propylbenzoic acid.

Anal. Calcd for $C_{24}H_{32}O_7$: C, 67.55; H, 7.26 Found: C, 67.18; H, 7.38.

EXAMPLE 148

4-[6-(2,3-Dihydroxyphenyl)hexyloxy]-2-hydroxy-3-propylbenzoic acid hexyl ester

A mixture of 1.00 g (2.57 mmol) of 4-[6-(2,3-dihydroxyphenyl)hexyloxy]-2-hydroxy-3-propylbenzoic acid, 0.76 mL (5.15 mmol) of n-hexyl iodide and 0.26 g (3.36 mmol) of sodium bicarbonate in 15 mL of anhydrous dimethylformamide was stirred and heated at 70° for 16 hours. The solvent was removed on the oil pump, water was added and the product was extracted with ethyl acetate. The dried extract was concentrated under reduced pressure to an oil which was purified by chromatography on silica gel using 5% ethyl acetate-toluene to give 1.01 g (83% yield) of 4-[6-(2,3-dihydroxyphenyl)hexyloxy]-2-hydroxy-3-propylbenzoic acid hexyl ester as an oil.

Anal. Calcd for $C_{28}H_{40}O_6$: C, 71.16; H, 8.53. Found: C, 70.89; H, 8.51.

EXAMPLE 149

4-Nitro-3-[6-[2,3-bis(phenylmethoxy)phenyl]hexyloxy]-benzoic acid phenylmethyl ester A mixture of 5.8 g (0.013 mol) of 1-(6-bromohexyl)-2,3-bis(phenylmethoxy)benzene, 3.5 g (0.013 mol) of 3-hydroxy-4-nitrobenzoic acid phenylmethyl ester, 3.5 g (0.026 mol) of anhydrous potassium carbonate and 2.9 g (0.019 mol) of sodium iodide in 125 ml of acetone and 13 ml of dimethylformamide was stirred and heated at reflux for 42 hours. Workup as described in example 16 and purification by HPLC using 10% ethyl acetate-hexane gave 5.45 g of 4-nitro-3-[6-[2,3-bis(phenylmethoxy)phenyl]hexyloxy]benzoic acid phenylmethyl ester as an oil.

Anal. Calcd for $C_{40}H_{39}NO_7$: C, 74.40; H, 6.09; N, 2.17. Found: C, 74.58; H, 6.08; N, 2.18.

EXAMPLE 150

4-Amino-3[6-(2,3-dihydroxyphenyl)hexyloxy]benzoic acid

A solution of 5.4 g of 4-nitro-3-[6-[2,3-bis(phenylmethoxy)phenyl]hexyloxy]benzoic acid phenylmethyl ester in 250 mL of tetrahydrofuran and 1 g of 10% palladium on carbon was shaken in a hydrogen atmosphere at room temperature for 17 hours. The catalyst was removed by filtration through celite and he filtrate was concentrated under reduced pressure to a solid.

Recrystallization form ether-methylene chloride gave 1.80 g (62% yield), mp 130°-132°, of 4-amino-3-[6-(2,3-dihydroxyphenyl)hexyloxy]benzoic acid.

Anal. Calcd for $C_{19}H_{23}NO_5$: C, 66.07; H, 6.71; N, 4.06. Found: C, 66.09; H, 6.86; N, 3.85.

EXAMPLE 151

3-Nitro-4-[6-[2,3-bis(phenylmethoxy)phenyl]hexyloxy]benzoic acid phenylmethyl ester A mixture of 5.8 g (0.013 mol) of 1-(6-bromohexyl)-2,3-bis(phenylmethoxy)benzene, 3.5 g (0.013 mol) of 4-hydroxy-3-nitrobenzoic acid phenylmethyl ester, 3.5 g (0.026 mol) of potassium carbonate and 2.9 g (0.019 mol) of sodium iodide in 125 mL of acetone and 13 mL of dimethylformamide was stirred and heated at reflux for 5 days. Workup as described in Example 16 and purification by HPLC using 50% methylene chloride-hexane gave 6.85 g (83% yield) of 3-nitro-4-[6-[2,3-bis(phenylmethoxy)phenyl]hexyloxy]benzoic acid phenylmethyl ester as an oil.

Anal. Calcd. for $C_{40}H_{39}NO_7$: C, 74.40; H, 6.09; N, 2.17. Found: C, 74.70; H, 6.14; N, 2.12.

EXAMPLE 152

3-Amino-4-[6-(2,3-dihydroxyphenyl)hexyloxy]benzoic acid

A solution of 6.8 g of 3-nitro-4-[6-[2,3-bis(phenylmethoxy)phenyl]hexyloxy]benzoic acid phenylmethyl ester in 250 mL of tetrahydrofuran and 1.3 g of 10% palladium on carbon was shaken in a hydrogen atmosphere at room temperature for 12 hours. The catalyst was removed by filtration through Celite and the filtrate was concentrated under reduced pressure to a solid. Recrystallization form acetone-hexane gave 2.36 g (65% yield), mp 172°-174°, of 3-amino-4-[6-(2,3-dihydroxyphenyl)hexyloxy]benzoic acid.

Anal. Calcd. for $C_{19}H_{23}NO_5$: C, 66.07; H, 6.71; N, 4.06. Found: C, 65.88; H, 6.85; N, 3.89.

EXAMPLE 153

1-(6-Bromohexyl)-2,3-dimethoxy-4-(1,1-dimethylethyl)benzene

To 27.0 g (0.139 mole) of 1,2-dimethoxy-3-(1,1-dimethylethyl)benzene in 350 mL of anhydrous tetrahydrofuran cooled in an ice-brine bath at −5° was added. 87 mL (0.139 mole) of 1.6M butyl lithium in hexane over 30 minutes. The reaction mixture was stirred at −5° for 3 hours and then at reflux for 1 hour. After cooling in an ice bath, 21.5 mL (0.139 mole) of 1,6-dibromohexane in 75 mL of tetrahydrofuran was added dropwise. The reaction mixture was then stirred at reflux for 17 hours. The solvent was removed under reduced pressure, 50 mL of 3N hydrochloric acid was added and the product was extracted with ether. The extract was washed with sodium bicarbonate solution, dried and concentrated at reduced pressure to an oil. Purification by HPLC using 20% toluene-hexane gave 7.6 g ((15% yield) of 1-(6-bromohexyl)-2,3-dimethoxy-4-(1,1-dimethylethyl)benzene.

Anal. Calcd for $C_{18}H_{29}BrO_2$: C, 60.50; H, 8.18; Br, 22.36. Found: C, 60.35; H, 8.25; Br, 22.08.

EXAMPLE 154

2-Hydroxy-4[6-[2,3-dimethoxy-4-(1,1-dimethylethyl)phenyl]hexyloxy]-3-propylbenzoic acid A mixture of 4.0 g (11.2 mmole) of 1-(6-bromohexyl)-2,3-dimethoxy-4-(1,1-dimethylethyl)benzene, 3.2 g (11.2 mmole) of 2,4-dihydroxy-3-propylbenzoic acid phenylmethyl ester, 3.1 g (22.4 mmole) of potassium carbonate and 1.7 g (11.2 mmole) of sodium iodide in 70 mL of anhydrous acetone and 7 mL of anhydrous dimethylformamide was stirred at reflux for 31 hours. Workup as in Example 16 and purification by HPLC using 5% ethyl acetate-hexane gave 5.3 g, (84% yield) of 2-hydroxy-4-[6-[2,3-dimethoxy-4-(1,1-dimethylethyl)phenyl]hexyloxy]-3-propylbenzoic acid phenylmethyl ester as an oil.

Anal. Calcd for $C_{35}H_{46}O_6$: C, 74.70; H, 8.24. Found: C, 74.96; H, 8.21.

A solution of 5.25 g of 2-hydroxy-4-[6-[2,3-dimethoxy-4-(1,1-dimethylethyl)phenyl]hexyloxy]-3-propylbenzoic acid phenylmethyl ester in 200 mL of tetrahydrofuran and 0.5 g of 10% palladium on carbon was shaken in a hydrogen atmosphere for 3 hours. The reaction mixture was filtered through Celite and the filtrate was concentrated to yield 4.0 g mp 106°-108°, of 2-hydroxy-4-[6-[2,3-dimethoxy-4-(1,1-dimethylethyl)phenyl]hexyloxy]-3-propylbenzoic acid.

Anal. Calcd for $C_{28}H_{40}O_6$: C, 71.16; H, 8.53. Found: C, 71.08; H, 8.44.

EXAMPLE 155

4-[6-[2,3-Dihydroxy-4-(1,1-dimethylethyl)phenyl]hexyloxy]-2-hydroxy-3-propylbenzoic acid To 4.0 g (8.5 mmole) of 2-hydroxy-4-[6-[2,3-dimethoxy-4-(1,1-dimethylethyl)phenyl]hexyloxy]-3-propylbenzoic acid suspended in 200 mL of methylene chloride and cooled at −70° was added 26 mL (26 mmole) of 1M boron tribromide in methylene chloride over 30 minutes. The reaction mixture was stirred at −70° for 30 minutes and kept at −20° for 41 hours. Workup as in Example 32 and recrystallization of the crude product from ether-hexane gave 1.78 g (47% yield), mp 85°-87°, of 4-[6-[2,3-dihydroxy-4-(1,1-dimethylethyl)phenyl]hexyloxy]-2-hydroxy-3-propylbenzoic acid.

Anal. Calcd for $C_{26}H_{36}O_6$: C, 70.24; H, 8.16. Found: C, 69.87; H, 8.11.

EXAMPLE 156

4-[6-(2,3-Dihydroxyphenyl)hexyloxy]benzoic acid ethyl ester

A mixture of 2.4 g (5.3 mmole) of 1-(6-bromohexyl)-2,3-bis-(phenylmethoxy)benzene, 0.88 g (5.3 mmole) of 4-hydroxybenzoic acid ethyl ester, 2.5 g (18 mmole) of potassium carbonate and 0.8 g (5.3 mmole) of sodium iodide in 40 mL of acetone was stirred at reflux for 22 hours. Workup as in Example 16 and recrystallization of the crude product from ethyl acetate-hexane gave 2.3 g, mp 63°-65° (81% yield) of 4-[6-[2,3-bis(phenylmethoxy)phenyl]hexyloxy]benzoic acid ethyl ester.

Anal. Calcd for $C_{35}H_{38}O_5$: C, 78.04; H, 7.11. Found: C, 77.89; H, 7.00.

A solution of 2.3 g of 4-[6-[2,3-bis(phenylmethoxy)phenyl]hexyloxy]benzoic acid ethyl ester in 50 mL of ethyl acetate and 0.3 g of 10% palladium on carbon was stirred in a hydrogen atmosphere for 22 hours. The reaction mixture was filtered through Celite and the filtrate was concentrated under reduced pressure to a solid. Recrystallization from ethyl acetate-hexane gave 1.3 g, mp 45°-47°, (85% yield) to 4-[6-(2,3-dihydroxyphenyl)hexyloxy]benzoic acid ethyl ester.

Anal. Calcd. for $C_{21}H_{26}O_5$: C, 70.37; H, 7.31. Found: C, 70.31; H, 7.50.

EXAMPLE 157

4-[6-(2,3-Dihydroxyphenyl)hexyloxy]-2-hydroxybenzoic acid ethyl ester

A mixture of 1.0 g (2.9 mmole) of 4-[6-(2,3-dihydroxyphenyl)hexyloxy]-2-hydroxybenzoic acid, 0.295 g (3.5 mmole) of sodium bicarbonate and 2.4 mL (29 mmole) of ethyl iodide in 10 ml of anhydrous dimethylformamide was stirred at 50° for 6 hours. The solvent was removed on the oil pump and the residue was treated with sodium bicarbonate solution. The product was extracted with ethyl acetate and the dried extract was concentrated at reduced pressure to a solid. Recrystallization from ether-hexane gave 0.8 g, mp 63°–68°, (74% yield) of 4-[6-(2,3-dihydroxyphenyl)hexyloxy]-2-hydroxybenzoic acid ethyl ester.

Anal. Calcd for $C_{21}H_{26}O_6$: C, 67.36; H, 7.00. Found: C, 67.41; H, 7.13.

EXAMPLE 158

4-[6-(3,4-Dihydroxy-2,5-dimethylphenyl)hexyloxy]-2-hydroxy-3-propolybenzoic acid ethyl ester A mixture of 0170 g (1.68 mmole) of 4-[6-(3,4-dihydroxy-2,5-dimethylphenyl)hexyloxy]-2-hydroxy-3-propylbenzoic acid, 0.157 g (1.87 mmole) of sodium bicarbonate and 1.4 mL (16.8 mmole) of ethyl iodide in 10 mL of dimethylformamide was stirred at 50° for 10 hours. Workup as in Example 160 gave an oil which was purified by chromatography on 20 g of silica gel. Elution with 25% ethyl acetate-hexane gave the product which was recrystallized from hexane to give 0.50 g, mp 61°–64°, (67% yield) of 4-[6-(3,4-dihydroxy-2,5-dimethylphenyl)hexyloxy]-2-hydroxy-3-propylbenzoic acid ethyl ester.

Anal. Calcd for $C_{26}H_{36}O_6$: C, 70.24; H, 8.16. Found: C, 70.21; H, 8.20.

EXAMPLE 159

TABLET FORMULATION (Wet Granulation)

| Item | Ingredient | mg/tablet 100 mg | mg/tablet 500 mg | mg/tablet 1000 mg |
|---|---|---|---|---|
| 1. | 4-[6-(2,3-dihydroxyphenyl)hexyloxy]-2-hydroxy-3-propyl-benzoic acid. | 100 | 500 | 1000 |
| 2. | Lactose | 132 | — | — |
| 3. | Pregelantinized Starch | 16 | 30 | 50 |
| 4. | Modified Starch | 30 | 40 | 50 |
| 5. | Magnesium Stearate | 2 | 6 | 8 |
| | TOTAL | 280 | 576 | 1108 |

Manufacturing Procedure:
1. Mix items 1, 2, 3 and 4 and granulate with water.
2. Dry the granulation at 50° C.
3. Pass the granulation through suitable milling equipment.
4. Add item 5 and mix for three minutes; compress on a suitable press.

EXAMPLE 160

CAPSULE FORMULATION

| | Ingredient | mg/capsule | | | |
|---|---|---|---|---|---|
| 1. | 4-[6-(2,3-dihydroxyphenyl)hexyloxy]-2-hydroxy-3-propyl-benzoic acid. | 25 | 50 | 100 | 500 |
| 2. | Lactose Hydrous | 143 | 168 | 148 | — |
| 3. | Corn Starch | 20 | 20 | 40 | 70 |
| 4. | Talc | 10 | 10 | 10 | 25 |
| 5. | Magnesium Stearate | 2 | 2 | 2 | 5 |
| | TOTAL | 200 | 250 | 300 | 600 |

Manufacturing Procedure:
1. Mix items 1, 2 and 3 in a suitable mixer for 30 minutes.
2. Add items 4 and 5 and mix for 3 minutes.
3. Fill into suitable capsules.

EXAMPLE 161

WET GRANULATION FORMULATION

| | Ingredient | mg/tablet | |
|---|---|---|---|
| 1. | 4-[6-(2,3-dihydroxyphenyl)hexyloxy]-2-hydroxy-3-propyl-benzoic acid. | 25 | 50 |
| 2. | Polyvinyl Pyrrolidone | 5 | 10 |
| 3. | Lactose Anhydrous DTG | 133 | 142 |
| 4. | Microcrystalline Cellulose | 25 | 30 |
| 5. | Modified Starch | 10 | 15 |
| 6. | Magnesium Stearate | 2 | 3 |
| | TOTAL | 200 | 250 |

Manufacturing Procedure:
1. Dissolve Item 2 in water.
2. Mix Items 1, 3, 4 and 5 in a suitable mixer and granulate with solution in Step 1.
3. Dry overnight at 45° C., screen through #20 mesh, and add Item 6 and mix. Compress on a suitable press.

EXAMPLE 162

CREAM 5%

The following is the quantitative composition of drug:

| | Ingredient | g/kg | Reasonable Variations |
|---|---|---|---|
| 1. | 4-[6-(2,3-dihydroxyphenyl)hexyloxy]-2-hydroxy-3-propyl-benzoic acid. | 51.50* | — |
| 2. | Glyceryl Monostearate S.E.[1] | 100.00 | 80–120 |
| 3. | Polysorbate 60[2] | 20.00 | 15–25 |
| 4. | Cetyl Alcohol | 50.00 | 40–60 |
| 5. | Petrolatum | 70.00 | 50–90 |
| 6. | Methylparaben | 1.50 | 1.25–1.75 |
| 7. | Propylparaben | 0.50 | 0.4–0.6 |
| 8. | Propylene Glycol | 200.00 | 150–250 |
| 9. | Purified Water | 521.70 | 475–575 |
| | Total | 1015.20 | |

*3% excess.
[1]Arlacel 165
[2]Tween 60

EXAMPLE 163

SOFT GELATIN CAPSULE FORMULATION

| | Ingredient | mg/capsule | |
|---|---|---|---|
| 1. | 4-[6-(2,3-dihydroxyphenyl)hexyloxy]-2-hydroxy-3-propyl-benzoic acid. | 50 | 150 |
| 2. | Polyethyleneglycol 400 | 325 | 550 |
| 3. | Med. Change Monoglycide | 100 | 150 |
| 4. | Polysorbate 80 | 25 | 50 |

-continued

| Ingredient | mg/capsule | |
|---|---|---|
| TOTAL | 500 | 1000 |

Manufacturing Procedure:
1. Dissolve Item 1 in Item 2.
2. Add Item 3 and mix well.
3. Add Item 4 and mix well until dissolved.
4. Fill in soft gelatin capsules.

EXAMPLE 164

BEADLET FORMULATION (ENTERIC) I

| Beadlets | mg/capsule | | |
|---|---|---|---|
| 1. 4-[6-(2,3-dihydroxyphenyl)hexyloxy]-2-hydroxy-3-propyl-benzoic acid. | 25 | 100 | 250 |
| 2. Microcrystalline cellulose | 100 | 200 | 250 |
| 3. Polyvinyl pyrrolidone K-90 | 10 | 20 | 30 |
| TOTAL | 135 | 320 | 530 |

Procedure:
1. Mix with microcrystalline cellulose and granulate with a solution of pVP K-90.
2. Pass the granulation through an extruder and marumarizer to obtain uniform beads.
3. Coat the beads with an enteric polymer such as Polyvinyl Acetate Phthlate, Hydroxypropyl Methylcellulose Phthlate, Cellulose Acetate phthlate, or an Acrylic Polymer.
4. Fill into capsules at the appropriate fill weight.

Beadlet Formulation (Enteric) II

Starting with non-pareil seeds, deposit on the seeds with an appropriate polymer, such as Polyvinyl Pyrrolidone, Hydroxypropyl Cellulose, Hydroxypropyl Methylcellulose or the like. Dry the seeds and apply an enteric membrane such as Polyvinyl Acetate Phthlate, Hydroxypropyl Methylcellulose Phthlate, Cellulose Acetate Phthlate and/or an Acrylic Polymer. Determine the concentration of the drug per gram of Beadlet and fill into capsules.

We claim:

1. A compound of the formula

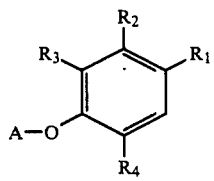

I wherein,
$R_1$ is

hydrogen, acetyl, hydroxy or alkanoyloxy,
$R_2$ is

hydroxy, hydrogen or alkanoyloxy,
wherein R is hydrogen, lower alkyl or —(CH$_2$)$_n$—N—(lower alkyl)$_2$,
$R_3$ is hydrogen, lower alkyl or amino,
$R_4$ is hydrogen, lower alkyl, halogen or amino, and
A is

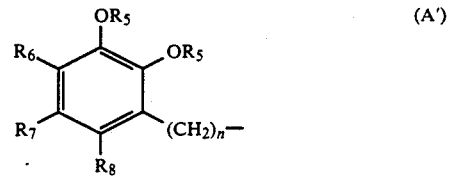

(A')

or

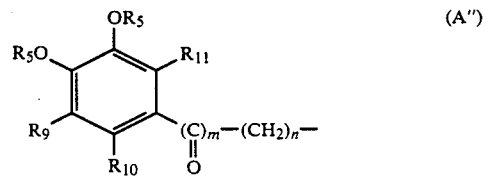

(A")

wherein, $R_5$ is hydrogen, benzoyl or alkanoyl of 1 to 7 carbon atoms, $R_6$ is hydrogen, halogen lower alkyl, cycloalkyl, phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$, independently, are hydrogen, lower alkyl or halogen, $R_9$ is hydrogen or lower alkyl, $R_{10}$ is lower alkyl, hydrogen or halogen $R_{11}$ is hydrogen, lower alkyl, cycloalkyl or halogen, m is 0 or 1, n is an integer of 2 to 10, provided, that no more than one of $R_1$ or $R_2$ can be hydroxy, alkanoyloxy or

or, when R is hydrogen, a salt thereof with a pharmaceutically acceptable base, or, when R is —(CH$_2$)$_n$—N—(lower alkyl)$_2$, an addition salt thereof with a pharmaceutically acceptable acid.

2. A compound, in accordance with claim 1, wherein A is

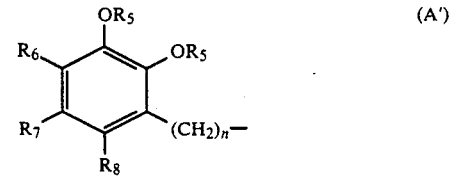

(A')

wherein $R_5$ is hydrogen, benzoyl or alkanoyl of 1 to 7 carbon atoms, $R_6$ is hydrogen, halogen, lower alkyl, cycloalkyl, phenyl or phenyl bearing one or two substituents independently selected from the group consisting of halogen, trifluoromethyl, lower alkyl, lower alkoxy, nitro, amino, lower alkylamino and di-lower alkylamino, $R_7$ and $R_8$, independently, are hydrogen, lower alkyl or halogen, and n is an integer of 2 to 10.

3. A compound, in accordance with claim 2, of the formula

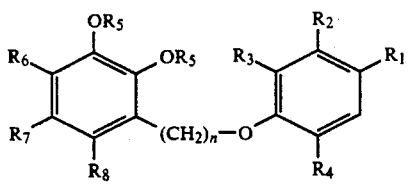 Ia

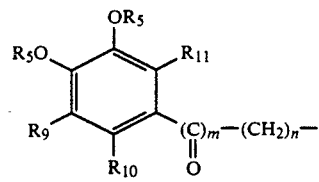 A'' wherein $R_1$ is carboxy or acetyl, $R_2$ is hydroxy, $R_3$ is hydrogen, propyl or amino, $R_4$ is hydrogen, chloro or amino, n is an integer from 2 to 10, $R_5$ is hydrogen or acetyl, $R_6$ is hydrogen, lower alkyl, phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$ are hydrogen.

4. A compound, in accordance with claim 3, wherein $R_1$ is carboxy or acetyl, $R_2$ is hydroxy, $R_3$ is hydrogen or propyl, $R_4$ is hydrogen or chloro, n is an integer from 4 to 8, $R_5$ is hydrogen or acetyl, $R_6$ is hydrogen or lower alkyl, and $R_7$ and $R_8$ are hydrogen.

5. A compound, in accordance with claim 4, wherein $R_1$ is carboxy, $R_2$ is hydroxy, $R_3$ is hydrogen or n-propyl, $R_4$ is hydrogen, n is an integer from 4 to 6, $R_5$ is hydrogen, $R_6$ is hydrogen or α-branched lower alkyl, and $R_7$ and $R_8$ are hydrogen.

6. A compound, in accordance with claim 1, 4-[4-(2,3-dihydroxyphenyl)butoxy]-2-hydroxy-3-propylbenzoic acid.

7. A compound in accordance with claim 1, 4-[6-(2,3-dihydroxyphenyl)hexyloxy]-2-hydroxy-3-propylbenzoic acid.

8. A compound in accordance with claim 1, 4-[8-(2,3-dihydroxyphenyl)octyloxy]-2-hydroxy-3-propylbenzoic acid.

9. A compound in accordance with claim 1, 4-[6-(2,3-dihydroxyphenyl)hexyloxy]2-hydroxy-3-propylbenzoic acid ethyl ester.

10. A compound in accordance with claim 1, 4-[6-(2,3-dihydroxyphenyl)hexyloxy]2-hydroxy-3-propylbenzoic acid [2-(diethylamino)ethyl]ester.

11. A compound in accordance with claim 1, 4-[6-[2,3-bis(acetyloxy)phenyl]hexyloxy]2-hydroxy-3-propylbenzoic acid.

12. A compound in accordance with claim 1, 4-[6-[2,3-dihydroxy-4-(1-methylethyl)phenyl]hexyloxy]-2-hydroxy-3-propyl benzoic acid.

13. A compound in accordance with claim 1, 1-[2-hydroxy-4-[4-(2,3-dihydroxyphenyl)butoxy]-3-propylphenyl]ethanone.

14. A compound in accordance with claim 1, 1-[2-hydroxy-4-[6-[2,3-dihydroxy-4-(1-methylethyl)phenyl]hexyloxy]-3-propylphenyl]ethanone.

15. A compound in accordance with claim 1, 5-chloro-4-[6-(2,3-dihydroxyphenyl)hexyloxy]-2-hydroxy-3-propylbenzoic acid.

16. A compound in accordance with claim 1, 4-[6-(2,3-dihydroxyphenyl)hexyloxy]-2-hydroxybenzoic acid.

17. A compound in accordance with claim 1, 4-[6-(2,3-dihydroxyphenyl)hexyloxy]benzoic acid.

18. A compound in accordance with claim 1, 4-[5-(2,3,4-trichloro-5,6-dihydroxyphenyl)pentyloxy]-2-hydroxy-3-propylbenzoic acid.

19. A compound, in accordance with claim 1, wherein A is wherein $R_5$ is hydrogen, benzoyl or alkanoyl of 1 to 7 carbon atoms, $R_9$ is hydrogen or lower alkyl, $R_{10}$ is hydrogen, lower alkyl or halogen, $R_{11}$ is hydrogen, lower alkyl, cycloalkyl or halogen, m is 0 or 1, n is an integer of 2 to 10.

20. A compound in accordance with claim 19, of the formula

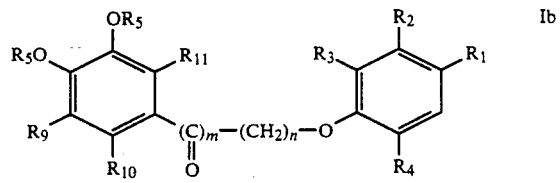 Ib wherein $R_1$ is carboxy or acetyl, $R_2$ is hydroxy, $R_3$ is hydrogen, propyl or amino, $R_4$ is hydrogen, chloro or amino, m is 0 or 1, n is an integer from 2 to 10, $R_5$ is hydrogen or acetyl, $R_9$ and $R_{10}$ are hydrogen, and $R_{11}$ is hydrogen or chloro.

21. A compound in accordance with claim 20, wherein $R_1$ is carboxy or acetyl, $R_2$ is hydroxy, $R_3$ is n-propyl, $R_4$ is hydrogen, m is 0, n is an integer from 4 to 6, $R_5$ is hydrogen or acetyl, $R_9$ and $R_{10}$ are hydrogen, and $R_{11}$ is hydrogen or chloro.

22. A compound, in accordance with claim 21, wherein $R_1$ is carboxy, $R_2$ is hydroxy, $R_3$ is n-propyl, $R_4$ is hydrogen, m is 0, n is an integer from 4 to 6, $R_5$, $R_9$, $R_{10}$ and $R_{11}$ are hydrogen.

23. A compound in accordance with claim 19, 4-[3-(3,4-dihydroxyphenyl)propoxy]-2-hydroxy-3-propylbenzoic acid.

24. A compound in accordance with claim 19, 4-[6-(3,4-dihydroxyphenyl)hexyloxy]-2-hydroxy-3-propylbenzoic acid.

25. A compound in accordance with claim 19, 4-[[6-(3,4-dihydroxyphenyl)-6-oxohexyl]oxy]-2-hydroxy-3-propylbenzoic acid.

26. A compound in accordance with claim 19, 1-[4-[5-(3,4-dihydroxyphenyl)pentyloxy]-2-hydroxy-3-propylphenyl]-1-ethanone.

27. A compound in accordance with claim 19, 4-[6-(3,4-dihydroxy-2,5-dimethylphenyl)hexyloxy]-2-hydroxy-3-propylbenzoic acid.

28. A lipoxygenase inhibiting pharmaceutical composition comprising an effective amount of a compound of the formula

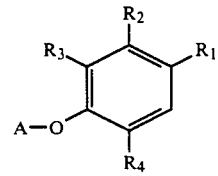 I wherein,
$R^1$ is

acetyl, hydrogen, hydroxy or alkanoyloxy,
$R_2$ is

hydroxy, hydrogen or alkanoyloxy,
wherein R is hydrogen, lower alkyl or $(CH_2)_n$—N—(lower alkyl)$_2$,
$R_3$ is hydrogen, lower alkyl or amino,
$R_4$ is hydrogen, lower alkyl, halogen or amino, and
A is

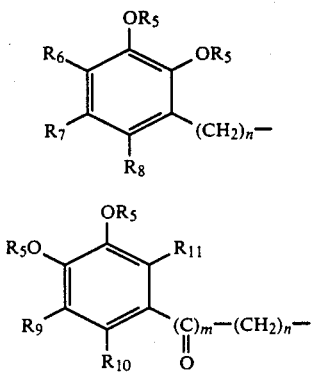

wherein, $R_5$ is hydrogen, benzoyl or alkanoyl of 1 to 7 carbon atoms, $R_6$ is hydrogen, halogen, lower alkyl, cycloalkyl, phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$, independently, are hydrogen, lower alkyl or halogen, or $R_9$ is hydrogen or lower alkyl, $R_{10}$ is hydrogen, lower alkyl or halogen, $R_{11}$ is hydrogen, lower alkyl, cycloalkyl or halogen, m is 0 or 1, n is an integer of 2 to 10, provided, that no more than one of $R_1$ or $R_2$ can be hydroxy, alkanoyloxy or

or, when R is hydrogen, a salt thereof with a pharmaceutically acceptable base, or when R is —(CH$_2$)$_n$—N—(lower alkyl)$_2$ an addition salt thereof with a pharmaceutically acceptable acid and an inert carrier material.

29. A lipoxygenase inhibiting pharmaceutical composition, in accordance with claim 28, wherein A is

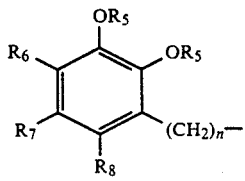

wherein $R_5$ is hydrogen, benzoyl or alkanoyl of 1 to 7 carbon atoms, $R_6$ is hydrogen, lower alkyl, cycloalkyl, phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$, independently, are hydrogen, lower alkyl or halogen, and n is an integer of 2 to 10.

30. A lipoxygenase inhibiting pharmaceutical composition in accordance with claim 29, wherein a compound of formula I is a compound of the formula

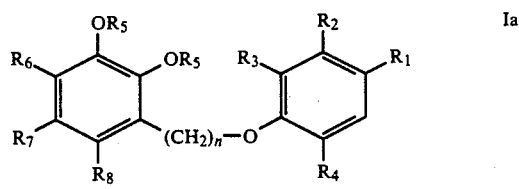

wherein $R_1$ is carboxy or acetyl, $R_2$ is hydroxy, $R_3$ is hydrogen or propyl, $R_4$ is hydrogen or chloro; n is an integer from 2 to 10, $R_5$ is hydrogen or acetyl, $R_6$ is hydrogen, halogen, lower alkyl, phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$ are hydrogen.

31. A pharmaceutical composition in accordance with claim 29, wherein $R_1$ is carboxy or acetyl, $R_2$ is hydroxy, $R_3$ is hydrogen or propyl, $R_4$ is hydrogen or chloro, n is an integer from 4 to 8, $R_5$ is hydrogen or acetyl, $R_6$ is hydrogen or lower alkyl and $R_7$ and $R_8$ are hydrogen.

32. A pharmaceutical composition, in accordance with claim 31, wherein $R_1$ is carboxy, $R_2$ is hydroxy, $R_3$ is hydrogen or n-propyl, $R_4$ is hydrogen, n is an integer from 4 to 6, $R_5$ is hydrogen, $R_6$ is hydrogen or α-branched lower alkyl, and $R_7$ and $R_8$ are hydrogen.

33. A pharmaceutical composition, in accordance with claim 28, wherein the compound of formula I is 4-[6-(2,3-dihydroxyphenyl)hexyloxy]-2-hydroxy-3-propylbenzoic acid.

34. A pharmaceutical composition, in accordance with claim 28, wherein the compound of formula I is 4-[6-(2,3-dihydroxyphenyl)hexyloxy]-2-hydroxybenzoic acid.

35. A lipoxygenase inhibiting pharmaceutical composition in accordance with claim 28, wherein A is

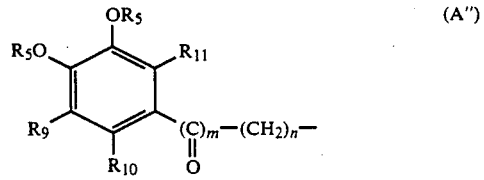

wherein $R_5$ is hydrogen, benzoyl or alkanoyl of 1 to 7 carbon atoms, $R_9$ is hydrogen or lower alkyl, $R_{10}$ is hydrogen, lower alkyl or halogen, $R_{11}$ is hydrogen, lower alkyl cycloalkyl or halogen, m is 0 or 1, n is an integer of 2-10.

36. A pharmaceutical composition in accordance with claim 35, wherein the compound of formula I is a compound of the formula

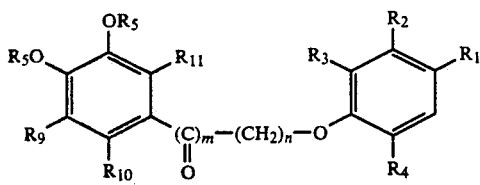

wherein $R_1$ is carboxy or acetyl, $R_2$ is hydroxy, $R_3$ is hydrogen or propyl, $R_4$ is hydrogen, m is 0 or 1, n is an integer from 2 to 10, $R_5$ is hydrogen, $R_9$ and $R_{10}$ are hydrogen, and $R_{11}$ is hydrogen or chloro.

37. A pharmaceutical composition in accordance with claim 35, wherein $R_1$ is carboxy or acetyl, $R_2$ is hydroxy, $R_3$ is n-propyl, $R_4$ is hydrogen, m is 0, n is an integer from 4 to 6, $R_5$ is hydrogen or acetyl, $R_9$ and $R_{10}$ are hydrogen, and $R_{11}$ is hydrogen or chloro.

38. A pharmaceutical composition in accordance with claim 37, wherein $R_1$ is carboxy, $R_2$ is hydroxy, $R_3$ is n-propyl, $R_4$ is hydrogen, m is 0, n is an integer from 4 to 6, $R_5$, $R_9$, $R_{10}$ and $R_{11}$ are hydrogen.

39. A pharmaceutical composition, in accordance with claim 36, wherein the compound of formula I is 4-[3-(3,4-dihydroxyphenyl)propoxy]-2-hydroxy-3-propylbenzoic acid.

40. A pharmaceutical composition, in accordance with claim 36, wherein the compound of formula I is 4-[6-(3,4-dihydroxy-2,5-dimethylphenyl)hexyloxy]-2-hydroxy-3-propylbenzoic acid.

41. A method of inhibiting lipoxygenase in a host requiring such treatment which comprises administering an effective amount of a compound

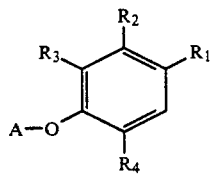

wherein,
$R^1$ is

acetyl, hydrogen, hydroxy or alkanoyloxy,
$R_2$ is

hydroxy, hydrogen or alkanoyloxy,
wherein R is hydrogen, lower alkyl or —(CH$_2$)$_n$—N—(lower alkyl)$_2$,
$R_3$ is hydrogen, lower alkyl or amino,
$R_4$ is hydrogen, lower alkyl, halogen or amino, and
A is

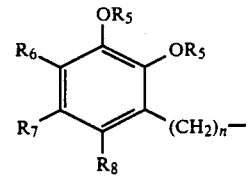

or

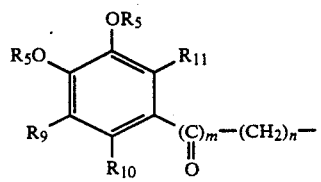

wherein, $R_5$ is hydrogen, benzoyl or alkanoyl of 1 to 7 carbon atoms, $R_6$ is hydrogen, halogen, lower alkyl, cycloalkyl, phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$, independently, are hydrogen, lower alkyl or halogen, or $R_9$ is hydrogen or lower alkyl, $R_{10}$ is hydrogen, lower alkyl or halogen, $R_{11}$ is hydrogen, lower alkyl, cycloalkyl or halogen, m is 0 or 1, n is an integer of 2 to 10, provided, that no more than one of $R_1$ or $R_2$ can be hydroxy, alkanoyloxy, or

or a salt thereof with a pharmaceutically acceptable base when R is hydrogen or when R is —(CH$_2$)$_n$—N—(lower alkyl)$_2$, an addition salt thereof with a pharmaceutically acceptable acid.

42. A method in accordance with claim 41, wherein A is

43. A method, in accordance with claim 42, wherein a compound of formula I is a compound of the formula

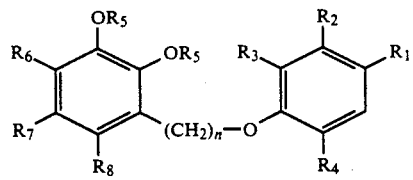

wherein $R_1$ is carboxy or acetyl, $R_2$ is hydroxy, $R_3$ is hydrogen or propyl, $R_4$ is hydrogen or chloro, n is an integer from 2 to 10, $R_5$ is hydrogen or acetyl, $R_6$ is hydrogen, halogen, lower alkyl, phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$ are hydrogen.

44. A method, in accordance with claim 43, wherein $R_1$ is carboxy or acetyl, $R_2$ is hydroxy, $R_3$ is hydrogen or propyl, $R_4$ is hydrogen or chloro, n is an integer from 4 to 8, $R_5$ is hydrogen or acetyl, $R_6$ is hydrogen or lower alkyl, $R_7$ and $R_8$ are hydrogen.

45. A method, in accordance with claim 44, wherein $R_1$ is carboxy, $R_2$ is hydroxy, $R_3$ is hydrogen or n-propyl, $R_4$ is hydrogen, n is an integer from 4 to 6, $R_5$ is hydrogen, $R_6$ is hydrogen or α-branched lower alkyl, and $R_7$ and $R_8$ are hydrogen.

46. A method, in accordance with claim 41, wherein the compound of formula I is 4-[6-(2,3-dihydroxyphenyl)hexyloxy]-2-hydroxy-3-propylbenzoic acid.

47. A method, in accordance with claim 41, wherein the compound of formula I is 4-[6-(2,3-dihydroxyphenyl)hexyloxy]-2-hydroxybenzoic acid.

48. A method, in accordance with claim 41, wherein A is

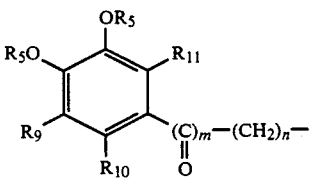
A''

49. A method, in accordance with claim 48, wherein a compound of formula I is

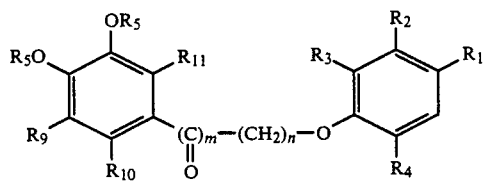
Ib wherein $R_1$ is carboxy or acetyl, $R_2$ is hydroxy, $R_3$ is hydrogen or propyl, $R_4$ is hydrogen, m is 0 or 1, n is an integer from 2 to 10, $R_5$ is hydrogen, $R_9$ and $R_{10}$ are hydrogen, and $R_{11}$ is hydrogen or chloro.

50. A method, in accordance with claim 49, wherein $R_1$ is carboxy or acetyl, $R_2$ is hydroxy, $R_3$ is n-propyl, $R_4$ is hydrogen, m is 0, n is an integer from 4 to 6, $R_5$ is hydrogen or acetyl, $R_9$ and $R_{10}$ are hydrogen, and $R_{11}$ is hydrogen or chloro.

51. A method, in accordance with claim 50, wherein $R_1$ is carboxy, $R_2$ is hydroxy, $R_3$ is n-propyl, $R_4$ is hydrogen, m is 0, n is an integer from 4 to 6, $R_5$, $R_9$, $R_{10}$ and $R_{11}$ are hydrogen.

52. A method, in accordance with claim 41, wherein the compound of formula I is 1-[4-[5-(3,4-dihydroxyphenyl)pentyloxy]-2-hydroxy-3-propylphenyl]-1-ethanone.

53. A method, in accordance with claim 41, wherein the compound of formula I is 4-[6-(3,4-dihydroxy-2,5-dimethylphenyl)hexyloxy]-2-hydroxy-3-propylbenzoic acid.

54. A compound in accordance with claim 1, 4-[5-(2,3-dihydroxyphenyl)pentyloxy]-2-hydroxy-3-propylbenzoic acid 55. A compound in accordance with claim 1, 2-hydroxy-4-[6-[2,3-bis[4-methylbenzoyl)oxy]phenyl]-hexyloxy]-3-propyl benzoic acid.

56. A pharmaceutical composition useful for the treatment of inflammatory bowel disease which comprises a compound of the formula

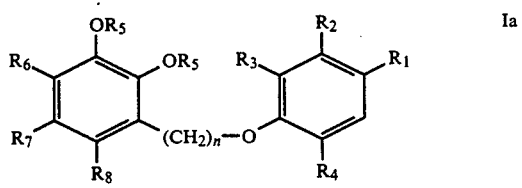
Ia wherein $R_1$ is carboxy or acetyl, $R_2$ is hydroxy, $R_3$ is hydrogen or propyl, $R_4$ is hydrogen or chloro, n is an integer from 2 to 10, $R_5$ is hydrogen or acetyl, $R_6$ is hydrogen, lower alkyl, phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$ are hydrogen, and an inert carrier material.

57. A pharmaceutical composition, in accordance with claim 56, wherein the compound is 4-[5-(2,3-dihydroxyphenyl)pentyloxy]-2-hydroxy-3-propylbenzoic acid.

58. A method for the treatment of inflammatory bowel disease in a host requiring such treatment which comprises administering an effect amount of a compound of the formula

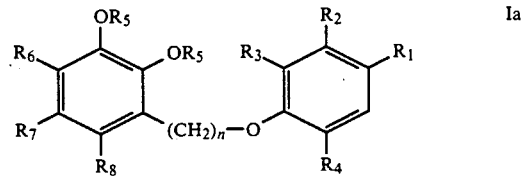
Ia wherein $R_1$ is carboxy or acetyl, $R_2$ is hydroxy, $R_3$ is hydrogen or propyl, $R_4$ is hydrogen or chloro, n is an integer from 2 to 10, $R_5$ is hydrogen or acetyl, $R_6$ is hydrogen, halogen, lower alkyl phenyl or phenyl bearing one or two substituents independently selected from the group consisting of halogen, trifluoromethyl, lower alkyl, lower alkoxy, nitro, amino, lower alkylamino and di-lower alkylamino, and $R_7$ and $R_8$ are hydrogen.

59. A method, in accordance with claim 58, wherein the compound is 4-[5-(2,3-dihydroxyphenyl)pentyloxy]-2-hydroxy-3-propylbenzoic acid.

* * * * *

UNITED STATES PATENT AND TRADEMARK OFFICE
CERTIFICATE OF CORRECTION

PATENT NO. : 5,025,036

DATED : June 18, 1991

INVENTOR(S) : Matthew Carson, Ru-Jen Lee Han, Ronald Andrew LeMahieu

It is certified that error appears in the above-identified patent and that said Letters Patent is hereby corrected as shown below:

Claim 42, Column 78, Line 45

" 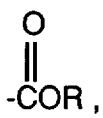 "  should be  ---- 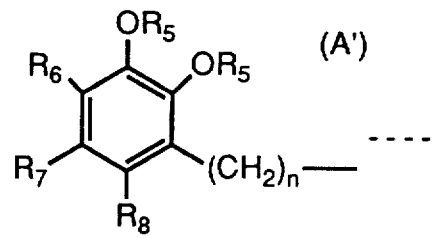 ----

Signed and Sealed this

Thirtieth Day of March, 1993

Attest:

STEPHEN G. KUNIN

*Attesting Officer*      *Acting Commissioner of Patents and Trademarks*